US012281126B2

(12) United States Patent
Gray et al.

(10) Patent No.: US 12,281,126 B2
(45) **Date of Patent: *Apr. 22, 2025**

(54) INHIBITORS OF CYCLIN-DEPENDENT KINASE 7 AND USES THEREOF

(71) Applicant: Dana-Farber Cancer Institute, Inc., Boston, MA (US)

(72) Inventors: Nathanael S. Gray, Boston, MA (US); Tinghu Zhang, Brookline, MA (US); Nicholas Paul Kwiatkowski, Brookline, MA (US); Jie Jiang, Brookline, MA (US); Mingfeng Hao, Hefei (CN); Zhixiang He, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 944 days.

This patent is subject to a terminal disclaimer.

(21) Appl. No.: 17/418,353

(22) PCT Filed: Dec. 27, 2019

(86) PCT No.: PCT/US2019/068835

§ 371 (c)(1),
(2) Date: Jun. 25, 2021

(87) PCT Pub. No.: WO2020/140098

PCT Pub. Date: Jul. 2, 2020

(65) Prior Publication Data

US 2022/0089611 A1 Mar. 24, 2022

Related U.S. Application Data

(60) Provisional application No. 62/786,328, filed on Dec. 28, 2018.

(51) Int. Cl.

| | |
|---|---|
| ***C07D 519/00*** | (2006.01) |
| ***A61K 31/4162*** | (2006.01) |
| ***C07D 487/04*** | (2006.01) |

(52) U.S. Cl.

CPC ........ *C07D 519/00* (2013.01); *A61K 31/4162* (2013.01); *C07D 487/04* (2013.01)

(58) Field of Classification Search

None

See application file for complete search history.

(56) References Cited

U.S. PATENT DOCUMENTS

| | | | |
|---|---|---|---|
| 4,231,938 | A | 11/1980 | Monaghan et al. |
| 4,270,537 | A | 6/1981 | Romaine et al. |
| 4,596,556 | A | 6/1986 | Morrow et al. |
| 4,782,084 | A | 11/1988 | Vyas et al. |
| 4,790,824 | A | 12/1988 | Morrow et al. |
| 4,885,314 | A | 12/1989 | Vyas et al. |
| 4,886,499 | A | 12/1989 | Cirelli et al. |
| 4,940,460 | A | 7/1990 | Casey et al. |
| 4,941,880 | A | 7/1990 | Burns et al. |
| 5,015,235 | A | 5/1991 | Crossman et al. |
| 5,064,413 | A | 11/1991 | McKinnon et al. |
| 5,141,496 | A | 8/1992 | Dalto et al. |
| 5,190,521 | A | 3/1993 | Hubbard et al. |
| 5,312,335 | A | 5/1994 | McKinnon et al. |
| 5,328,483 | A | 7/1994 | Jacoby et al. |
| 5,334,144 | A | 8/1994 | Alchas et al. |
| 5,339,163 | A | 8/1994 | Homma et al. |
| 5,383,851 | A | 1/1995 | McKinnon et al. |
| 5,417,662 | A | 5/1995 | Hjertman et al. |
| 5,420,245 | A | 5/1995 | Brown et al. |
| 5,466,220 | A | 11/1995 | Brenneman et al. |
| 5,480,381 | A | 1/1996 | Weston et al. |
| 5,484,596 | A | 1/1996 | Hanna et al. |
| 5,503,627 | A | 4/1996 | McKinnon et al. |
| 5,510,510 | A | 4/1996 | Patel et al. |
| 5,520,639 | A | 5/1996 | Peterson et al. |
| 5,523,430 | A | 6/1996 | Patel et al. |

(Continued)

FOREIGN PATENT DOCUMENTS

| | | |
|---|---|---|
| CA | 2486101 A1 | 11/2003 |
| CA | 2503646 A1 | 5/2004 |

(Continued)

OTHER PUBLICATIONS

U.S. Appl. No. 17/034,822, filed Sep. 28, 2020, Gray et al.
U.S. Appl. No. 18/181,463, filed Mar. 9, 2023, Gray et al.
U.S. Appl. No. 17/715,874, filed Apr. 7, 2022, Gray et al.
U.S. Appl. No. 17/255,647, filed Dec. 23, 2020, Gray et al.
U.S. Appl. No. 17/628,794, filed Jan. 20, 2022, Zhang et al.
U.S. Appl. No. 17/789,047, filed Jun. 24, 2022, Gray et al.
PCT/US2013/065708, Feb. 14, 2014, International Search Report and Written Opinion.
PCT/US2013/065708, Apr. 30, 2015, International Preliminary Report on Patentability.

(Continued)

*Primary Examiner* — Bong-Sook Baek

(74) *Attorney, Agent, or Firm* — Nielsen IP Law LLC

(57) ABSTRACT

The present disclosure provides compounds of Formula (I), and pharmaceutically acceptable salts, solvates, hydrates, polymorphs, co-crystals, tautomers, stereoisomers, isotopically labeled derivatives, and prodrugs thereof. The compounds of the present disclosure are inhibitors of kinases (e.g., a cyclin-dependent kinase (CDK) (e.g., CDK7)). The compounds may be selective for inhibiting the activity of a kinase (e.g., CDK7) over certain other kinases (e.g., CDK2, CDK9, CDK12). Also provided are pharmaceutical compositions, kits, methods of use, and uses that involve the compounds. The compounds may be useful in inhibiting the activity of a kinase, down-regulating the transcription of MYC or MCL-1, inhibiting the growth of a cell, inducing apoptosis of a cell, treating a disease, and/or preventing a disease (e.g., proliferative disease, cystic fibrosis).

15 Claims, 3 Drawing Sheets

(56) References Cited

U.S. PATENT DOCUMENTS 5,527,288 A 6/1996 Gross et al.
5,532,359 A 7/1996 Marsters et al.
5,569,189 A 10/1996 Parsons et al.
5,571,792 A 11/1996 Bolton et al.
5,589,485 A 12/1996 Hocolowski et al.
5,599,302 A 2/1997 Lilley et al.
5,602,098 A 2/1997 Sebti et al.
5,643,958 A 7/1997 Iwasawa et al.
5,649,912 A 7/1997 Peterson et al.
5,661,152 A 8/1997 Bishop et al.
5,704,911 A 1/1998 Parsons et al.
5,750,567 A 5/1998 Baudoin et al.
5,856,439 A 1/1999 Clerc et al.
5,889,053 A 3/1999 Baudoin et al.
5,893,397 A 4/1999 Peterson et al.
5,925,641 A 7/1999 Kanda et al.
5,936,097 A 8/1999 Commercon et al.
5,993,412 A 11/1999 Deily et al.
6,069,134 A 5/2000 Roth et al.
6,143,764 A 11/2000 Kubo et al.
6,214,852 B1 4/2001 Kim et al.
6,921,763 B2 7/2005 Hirst et al.
6,939,874 B2 9/2005 Harmange et al.
7,115,617 B2 10/2006 Buchanan et al.
7,312,225 B2 12/2007 Luecking et al.
7,728,131 B2 6/2010 Asaki et al.
7,884,117 B2 2/2011 Zhang et al.
7,928,140 B2 4/2011 Booker et al.
8,273,765 B2 9/2012 Fancelli et al.
8,394,818 B2 3/2013 Gray et al.
8,765,747 B2 7/2014 Choi et al.
8,877,761 B2 11/2014 Li
8,889,706 B2 11/2014 Gray et al.
8,987,275 B2 3/2015 Gray et al.
9,180,127 B2 11/2015 Gray et al.
9,358,231 B2 6/2016 Gray et al.
9,382,239 B2 7/2016 Gray et al.
9,505,784 B2 11/2016 Choi et al.
9,670,165 B2 6/2017 Cohen et al.
9,758,522 B2 9/2017 Gray et al.
9,814,709 B2 11/2017 Liu et al.
9,862,688 B2 1/2018 Gray et al.
9,879,003 B2 1/2018 Gray et al.
10,000,483 B2 6/2018 Gray et al.
10,017,477 B2 7/2018 Gray et al.
10,047,070 B2 8/2018 Gray et al.
10,112,927 B2 10/2018 Gray et al.
10,144,730 B2 12/2018 Gray et al.
10,336,760 B2 7/2019 Marineau et al.
10,342,798 B2 7/2019 Gray et al.
10,550,121 B2 2/2020 Gray et al.
10,695,346 B2 6/2020 Gray et al.
10,702,527 B2 7/2020 Hammerman et al.
RE48,175 E 8/2020 Gray et al.
10,787,436 B2 9/2020 Gray et al.
10,870,651 B2 12/2020 Gray et al.
10,969,394 B2 4/2021 Marto et al.
11,142,507 B2 10/2021 Gray et al.
11,306,070 B2 4/2022 Gray et al.
11,325,910 B2 5/2022 Gray et al.
11,932,625 B2 3/2024 Gray et al.
2003/0139416 A1 7/2003 Buchanan et al.
2004/0106634 A1 6/2004 Satoh et al.
2004/0126359 A1 7/2004 Lamb et al.
2004/0209878 A1 10/2004 Guzi et al.
2005/0026914 A1 2/2005 Buchanan et al.
2005/0197338 A1 9/2005 Huang et al.
2005/0228031 A1 10/2005 Bilodeau et al.
2005/0250837 A1 11/2005 D'Mello et al.
2006/0106083 A1 5/2006 Martina et al.
2006/0189627 A1 8/2006 Laird et al.
2006/0252748 A1 11/2006 Lindenthal et al.
2007/0004705 A1 1/2007 Brasca et al.
2007/0060546 A1 3/2007 Ruat et al.
2007/0093537 A1 4/2007 Hynes et al.
2007/0155746 A1 7/2007 Lang et al.
2007/0185171 A1 8/2007 Germain et al.
2007/0225286 A1 9/2007 Ren et al.
2007/0275963 A1 11/2007 Guzi et al.
2007/0281907 A1 12/2007 Watkins
2008/0039629 A1 2/2008 Ramesh et al.
2008/0090849 A1 4/2008 Bordon-Pallier et al.
2008/0103167 A1 5/2008 Bebernitz et al.
2008/0214501 A1 9/2008 Pan et al.
2008/0249079 A1 10/2008 Chen et al.
2008/0300267 A1 12/2008 Okram et al.
2009/0054392 A1 2/2009 Pelletier et al.
2009/0054405 A1 2/2009 Booker et al.
2009/0082346 A1 3/2009 Brasca et al.
2009/0105250 A1 4/2009 Sim et al.
2009/0156582 A1 6/2009 Tsukamoto et al.
2009/0221632 A1 9/2009 Fancelli et al.
2009/0318440 A1* 12/2009 Zhang .................... A61P 35/00 544/405
2010/0029638 A1 2/2010 Melvin, Jr. et al.
2010/0056524 A1 3/2010 Mciver et al.
2010/0197688 A1 8/2010 Nantermet et al.
2010/0254905 A1 10/2010 Honigberg et al.
2011/0039873 A1 2/2011 Gaeta et al.
2011/0086858 A1 4/2011 Wang et al.
2011/0098280 A1 4/2011 Garcia-Echeverria et al.
2011/0178070 A1 7/2011 Gong et al.
2011/0207711 A1 8/2011 Katz et al.
2011/0212053 A1 9/2011 Qian et al.
2012/0088766 A1 4/2012 Choi et al.
2012/0094999 A1 4/2012 Gray et al.
2012/0165309 A1 6/2012 Takahashi et al.
2012/0196865 A1 8/2012 Ruat et al.
2012/0202809 A1 8/2012 Li et al.
2012/0277248 A1 11/2012 Caruso et al.
2012/0329771 A1 12/2012 Treu et al.
2013/0040949 A1 2/2013 Gray et al.
2013/0184264 A1 7/2013 Bradner et al.
2013/0184287 A1 7/2013 Gray et al.
2014/0187772 A1 7/2014 Bebbington et al.
2014/0303112 A1 10/2014 Chen et al.
2014/0309249 A1 10/2014 Gray et al.
2015/0094315 A1 4/2015 Choi et al.
2015/0157629 A1 6/2015 Gray et al.
2015/0166532 A1 6/2015 Gray et al.
2015/0203502 A1 7/2015 Cheng et al.
2015/0246913 A1 9/2015 Gray et al.
2015/0274728 A1 10/2015 Gray et al.
2015/0322528 A1 11/2015 Caponigro et al.
2016/0046636 A1 2/2016 Gray et al.
2016/0122323 A1 5/2016 Gray et al.
2016/0264551 A1 9/2016 Ciblat et al.
2016/0264554 A1 9/2016 Gray et al.
2016/0368910 A1 12/2016 Gray et al.
2017/0044111 A1 2/2017 Gray et al.
2017/0044112 A1 2/2017 Gray et al.
2017/0204096 A1 7/2017 Gelin et al.
2018/0093990 A1 4/2018 Gray et al.
2018/0169097 A1 6/2018 Hammerman et al.
2018/0319801 A1 11/2018 Gray et al.
2018/0344733 A9 12/2018 Gray et al.
2018/0362483 A1 12/2018 Gray et al.
2018/0369243 A9 12/2018 Gray et al.
2019/0015411 A9 1/2019 Hammerman et al.
2019/0031642 A1 1/2019 Gray et al.
2019/0055248 A1 2/2019 Gray et al.
2019/0241541 A1 8/2019 Ciblat et al.
2019/0248778 A1 8/2019 Gray et al.
2019/0315747 A9 10/2019 Gray et al.
2020/0017475 A9 1/2020 Gray et al.
2020/0024271 A9 1/2020 Gray et al.
2020/0277292 A1 9/2020 Gray et al.
2021/0115051 A1 4/2021 Gray et al.
2021/0292299 A1 9/2021 Gray et al.
2021/0317105 A9 9/2021 Gray et al.
2021/0300911 A1 10/2021 Gray et al.
2021/0315894 A9 10/2021 Gray et al.
2022/0024929 A9 1/2022 Gray et al.
2022/0055998 A1 2/2022 Gray et al.

(56) References Cited

U.S. PATENT DOCUMENTS

2022/0073512 A1 3/2022 Gray et al.
2022/0169631 A9 6/2022 Gray et al.
2022/0213067 A1 7/2022 Gray et al.
2022/0242865 A1 8/2022 Gray et al.
2022/0281874 A1 9/2022 Zhang et al.
2023/0114207 A1 4/2023 Gray et al.

FOREIGN PATENT DOCUMENTS

CA 2526430 A1 12/2004
CA 2550128 A1 6/2005
CA 2563212 A1 10/2005
CA 2805827 A1 2/2012
CA 2940488 A1 9/2015
CA 2954298 A1 1/2016
CA 2988461 A1 12/2016
CA 2895239 C 10/2020
CA 3134221 A1 11/2020
CA 2927917 C 8/2022
CN 1701073 11/2005
CN 1726217 A 1/2006
CN 1735614 2/2006
CN 100482665 5/2006
CN 1784410 6/2006
CN 102406644 A 4/2012
CN 102406646 A 4/2012
CN 102408408 A 4/2012
CN 103242341 A 8/2013
CN 104177363 A 12/2014
CN 104487594 A 4/2015
CN 107235906 A 10/2017
CN 107427521 A 12/2017
CN 107686477 A 2/2018
EP 0604181 A1 12/1993
EP 0618221 A2 3/1994
EP 0675112 A1 3/1995
EP 0696593 A2 8/1995
EP 1847531 A1 10/2007
EP 1 935 890 A1 6/2008
EP 2 311 842 A2 4/2011
EP 3214086 A1 9/2017
EP 3 273 966 A2 1/2018
GB 796524 A 6/1958
JP 2003-503351 A 1/2003
JP 2003-503481 A 1/2003
JP 2004-505977 2/2004
JP 2004-529140 A 9/2004
JP 2005-501860 A 1/2005
JP 2005-505535 A 2/2005
JP 2005-530711 A 10/2005
JP 2005-534635 A 11/2005
JP 2005-538100 A 12/2005
JP 2006-514026 4/2006
JP 2006-521394 A 9/2006
JP 2006-528163 A 12/2006
JP 2007-500226 A 1/2007
JP 2007-500725 A 1/2007
JP 2007-516201 A 6/2007
JP 2008-500320 A 1/2008
JP 2008-501669 A 1/2008
JP 2008-502610 A 1/2008
JP 2008-528465 A 7/2008
JP 2008-528467 A 7/2008
JP 2009-510110 A 3/2009
JP 2009-520805 5/2009
JP 2010-505905 2/2010
JP 2010-511655 A 4/2010
JP 2010-518069 5/2010
JP 2010-521487 A 6/2010
JP 2010-523643 7/2010
JP 2010-536869 A 12/2010
JP 2011-515371 A 5/2011
JP 2011-516533 A 5/2011
JP 2011-526594 A 10/2011
JP 2012-511021 A 5/2012
JP 2012-530071 A 11/2012
JP 2014-526549 A 10/2014
JP 2015-503625 A 2/2015
JP 2016-512534 A 4/2016
JP 2016-533379 A 10/2016
JP 2017-504651 A 2/2017
JP 2018-506531 A 3/2018
KR 10-2009-0053593 A 5/2009
WO WO 84/02131 A1 6/1984
WO WO 94/19357 A1 9/1994
WO WO 95/08542 A1 3/1995
WO WO 95/10514 A1 4/1995
WO WO 95/10515 A1 4/1995
WO WO 95/10516 A1 4/1995
WO WO 95/11917 A1 5/1995
WO WO 95/12572 A1 5/1995
WO WO 95/12612 A1 5/1995
WO WO 95/25086 A1 9/1995
WO WO 95/34535 A1 12/1995
WO WO 96/00736 A1 1/1996
WO WO 96/05168 A1 2/1996
WO WO 96/05169 A1 2/1996
WO WO 96/17861 A1 6/1996
WO WO 96/21456 A1 7/1996
WO WO 96/22278 A1 7/1996
WO WO 96/24611 A1 8/1996
WO WO 96/30017 A1 10/1996
WO WO 96/30018 A1 10/1996
WO WO 96/30343 A1 10/1996
WO WO 96/30362 A1 10/1996
WO WO 96/30363 A1 10/1996
WO WO 96/31111 A1 10/1996
WO WO 96/31477 A1 10/1996
WO WO 96/31478 A1 10/1996
WO WO 96/31501 A1 10/1996
WO WO 96/33159 A1 10/1996
WO WO 96/34850 A1 11/1996
WO WO 96/34851 A1 11/1996
WO WO 97/00252 A1 1/1997
WO WO 97/03047 A1 1/1997
WO WO 97/03050 A1 1/1997
WO WO 97/04785 A1 2/1997
WO WO 97/17070 A1 5/1997
WO WO 97/18813 A1 5/1997
WO WO 97/21701 A1 6/1997
WO WO 97/23478 A1 7/1997
WO WO 97/26246 A1 7/1997
WO WO 97/30053 A1 8/1997
WO WO 97/38665 A2 10/1997
WO WO 97/44350 A1 11/1997
WO WO 98/02436 A1 1/1998
WO WO 98/28980 A1 7/1998
WO WO 98/29119 A1 7/1998
WO WO 2000/050032 A1 8/2000
WO WO 2000/061186 A1 10/2000
WO WO 2001/002369 A2 1/2001
WO WO 2001/019829 A2 3/2001
WO WO 02/12242 A2 2/2002
WO WO 2002/076986 A1 10/2002
WO WO 2002/079197 A1 10/2002
WO WO 2002/080926 A1 10/2002
WO WO 2002/083653 A1 10/2002
WO WO 2002/096905 A1 12/2002
WO WO 2002/102800 A1 12/2002
WO WO 2003/018021 A1 3/2003
WO WO 2003/018022 A1 3/2003
WO WO 2003/026664 A1 4/2003
WO WO 2003/051847 A1 6/2003
WO WO 2003/078403 A2 9/2003
WO WO 2003/097610 A1 11/2003
WO WO 2004/005283 A1 1/2004
WO WO 2004/009601 A1 1/2004
WO WO 2004/010995 A1 2/2004
WO WO 2004/039796 A1 5/2004
WO WO 2004/078757 A2 9/2004
WO WO 2004/087699 A2 10/2004
WO WO 2004/100868 A2 11/2004
WO WO 2004/113303 A1 12/2004
WO WO 2004/113304 A1 12/2004

(56) References Cited

FOREIGN PATENT DOCUMENTS

WO WO 2005/002576 A2 1/2005
WO WO 2005/011597 A2 2/2005
WO WO 2005/058891 A1 6/2005
WO WO 2005/063709 A1 7/2005
WO WO 2005/097790 A1 10/2005
WO WO 2005/108397 A1 11/2005
WO WO 2005/116025 A2 12/2005
WO WO 2006/003276 A1 1/2006
WO WO 2006/024834 A1 3/2006
WO WO 2006/031806 A2 3/2006
WO WO 2006/072831 A1 7/2006
WO WO 2006/077414 7/2006
WO WO 2006/085685 A1 8/2006
WO WO 2007/002325 A1 1/2007
WO WO 2007/002433 A1 1/2007
WO WO 2007/024680 A1 3/2007
WO WO 2007/035428 A1 3/2007
WO WO 2007/042786 A2 4/2007
WO WO 2007/072153 A2 6/2007
WO WO 2007/075869 A2 7/2007
WO WO 2007/129195 A2 11/2007
WO WO 2007/138277 A1 12/2007
WO WO 2008/009954 A1 1/2008
WO WO 2008/063888 A2 5/2008
WO WO 2008/068171 A1 6/2008
WO WO 2008/074749 A1 6/2008
WO WO 2008/079460 A2 7/2008
WO WO 2008/080015 A2 7/2008
WO WO 2008/112913 A1 9/2008
WO WO 2008/124393 A1 10/2008
WO WO 2008/144253 A1 11/2008
WO WO 2008/151183 A1 12/2008
WO WO 2008/151304 A1 12/2008
WO WO 2008/157575 A2 12/2008
WO WO 2009/017822 A2 2/2009
WO WO 2009/028655 A1 3/2009
WO WO 2009/032694 A1 3/2009
WO WO 2009/115572 A2 9/2009
WO WO 2009/145360 A1 12/2009
WO WO 2009/152027 A1 12/2009
WO WO 2009/155017 A2 12/2009
WO WO 2010/008847 A2 1/2010
WO WO 2010/051781 A1 5/2010
WO WO 2010/065893 A1 6/2010
WO WO 2010/075542 A1 7/2010
WO WO 2010/092962 A1 8/2010
WO WO 2010/125799 A1 11/2010
WO WO 2010/144909 A1 12/2010
WO WO 2011/115725 A2 9/2011
WO WO 2013/014162 A1 1/2013
WO WO 2013/040436 A2 3/2013
WO WO 2013/049279 A2 4/2013
WO WO 2013/074986 A1 5/2013
WO WO 2013/154778 A1 10/2013
WO WO 2014/011398 A1 1/2014
WO WO 2014/063061 A1 4/2014
WO WO 2014/063068 A1 4/2014
WO WO 2014/165065 A1 10/2014
WO WO 2015/006754 A2 1/2015
WO WO 2015/013635 A2 1/2015
WO WO 2015/058126 A1 4/2015
WO WO 2015/058140 A1 4/2015
WO WO 2015/089479 A1 6/2015
WO WO 2015/117087 A1 8/2015
WO WO 2015/154022 A1 10/2015
WO WO 2015/154038 A1 10/2015
WO WO 2015/164604 A1 10/2015
WO WO 2015/164614 A1 10/2015
WO WO 2016/014542 A1 1/2016
WO WO 2016/014551 A1 1/2016
WO WO 2016/068287 A1 5/2016
WO WO 2016/105528 A2 6/2016
WO WO 2016/160617 A2 10/2016
WO WO 2016/193939 A1 12/2016
WO WO-2016201370 A1 * 12/2016 ......... A61K 31/4162
WO WO 2017/160717 A2 9/2017
WO WO 2020/100944 A1 5/2020
WO WO 2020/140098 A1 7/2020
WO WO 2021/016388 A1 1/2021
WO WO 2021/026109 A1 2/2021

OTHER PUBLICATIONS

PCT/US2014/061232, Dec. 23, 2014, International Search Report and Written Opinion.

PCT/US2015/027312, Jul. 10, 2015, International Search Report and Written Opinion.

PCT/US2015/027312, Nov. 3, 2016, International Preliminary Report on Patentability.

15873803.9, Apr. 12, 2018, Extended European Search Report.

PCT/US2015/000297, Mar. 4, 2016, International Search Report and Written Opinion.

PCT/US2015/000297, Jul. 6, 2017, International Preliminary Report on Patentability.

International Search Report and Written Opinion for PCT/US2019/068835, mailed May 27, 2020.

Invitation to Pay Additional Fees for PCT/US2019/068835, mailed Mar. 5, 2020.

International Preliminary Report on Patentability for PCT/US2019/068835, mailed Jul. 8, 2021.

Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.

Bai et al., Design, synthesis and anticancer activity of 1-acyl-3-amino-1,4,5,6-Tetrahydropyrrolo[3,4-c]pyrazole derivatives. Bioorg Med Chem Lett. Nov. 15, 2012;22(22):6947-51.Suppl. Info, 46 pages. doi: 10.1016/j.bmcl.2012.08.117. Epub Sep. 8, 2012.

Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.

Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.

Beeler et al., Role of the JNK-interacting protein 1/islet brain 1 in cell degeneration in Alzheimer disease and diabetes. Brain Res Bull. Oct. 28, 2009;80(4-5):274-81. doi: 10.1016/j.brainresbull.2009.07.006. Epub Jul. 16, 2009.

Bell et al., Integrated genomic analyses of ovarian carcinoma. Nature. Jun. 29, 2011;474(7353):609-15. doi: 10.1038/nature10166.

Ben-Av et al., Induction of vascular endothelial growth factor expression in synovial fibroblasts by prostaglandin E and interleukin-1: a potential mechanism for inflammatory angiogenesis. FEBS Letters 1995;372:83-7.

Benezra et al., In vivo angiogenic activity of interleukins. Archives of Opthamology 1990;108:573.

Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.

Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.

Bloom et al., The requirement for Phr1 in CNS axon tract formation reveals the corticostriatal boundary as a choice point for cortical axons. Genes Dev. Oct. 15, 2007;21(20):2593-606. Epub Sep. 27, 2007.

Bosken et al., The structure and substrate specificity of human Cdk12/Cyclin K. Nat Commun. Mar. 24, 2014;5:3505. doi: 10.1038/ncomms4505.

Brasca et al., 6-Substituted pyrrolo[3,4-c]pyrazoles: an improved class of CDK2 inhibitors. ChemMedChem. Jun. 2007;2(6):841-52.

Brunton et al., eds., Chemotherapy of Neoplastic Diseases. In Goodman & Gilman's The Pharmacological Basis of Therapeutics. 2008; 11th edition:853-908.

(56) References Cited

OTHER PUBLICATIONS

Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Cappuzzo et al., Increased MET gene copy No. negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Carvajal et al., KIT as a therapeutic target in metastatic melanoma. JAMA. Jun. 8, 2011;305(22):2327-34. doi: 10.1001/jama.2011.746.
CAS Registry No. 1334419-59-8, STN Entry Date Dec. 30, 2013.
CAS Registry No. 769961-59-3, STN Entry Date Oct. 27, 2004.
CAS Registry No. 916173-61-0, STN Entry Date Dec. 21, 2006.
CAS Registry No. 769961-42-4, STN Entry Date Oct. 27, 2004.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.
Chen et al., Antiapoptotic and trophic effects of dominant-negative forms of dual leucine zipper kinase in dopamine neurons of the substantia nigra in vivo. J Neurosci. Jan. 16, 2008;28(3):672-80. doi: 10.1523/JNEUROSCI.2132-07.2008.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Chiarugi et al., Cox-2, iNOS and p53 as play-makers of tumor angiogenesis. International Journal of Molecular Medicine 1998;2:715-9.
Choi et al., Development of ‘DFG-out’ inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials.
Chong et al., Positive and negative regulation of Raf kinase activity and function by phosphorylation Embo J. Jul. 16, 2001;20(14):3716-27.
Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.
Christensen et al., Targeting transcriptional addictions in small cell lung cancer with a covalent CDK7 inhibitor. Cancer Cell. Dec. 8, 2014;26(6):909-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Database Registry [Online] Retrieved from STN, 2011年12月4日, search date :Oct. 7, 2019; RN 1350102-23-6, 1349782-05-3, 1349471-31-3, 1349357-86-3, 1349106- 33-7, 1348397-56-7, 1348192-23-3, 1348088-42-5.
Davies et al., Mutations of the BRAF gene in human cancer Nature. Jun. 27, 2002;417(6892):949-54. Epub Jun. 9, 2002.
Davis et al., Comprehensive analysis of kinase inhibitor selectivity. Nat Biotechnol. Oct. 30, 2011;29(11):1046-51. doi: 10.1038/nbt.1990.
Desai et al., Effects of phosphorylation by CAK on cyclin binding by CDC2 and CDK2. Mol Cell Biol. Jan. 1995;15(1):345-50.
Diaz-Flores et al., Intense vascular sprouting from rat femoral vein induced by prostaglandins E1 and E2. Anatomical Record 1994;238:68-76.
Downward, Targeting RAS signalling pathways in cancer therapy Nat Rev Cancer. Jan. 2003;3(1):11-22.
Drapkin et al., Human cyclin-dependent kinase-activating kinase exists in three distinct complexes. Proc Natl Acad Sci U S A. Jun. 25, 1996;93(13):6488-93.
Ercan et al., Reactivation of ERK signaling causes resistance to EGFR kinase inhibitors. Cancer Discov. Oct. 2012;2(10):934-47.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fan et al., Dual leucine zipper-bearing kinase (DLK) activates p46SAPK and p38mapk but not ERK2. J Biol Chem. Oct. 4, 1996;271(40):24788-93.
Fancelli et al., Potent and selective Aurora inhibitors identified by the expansion of a novel scaffold for protein kinase inhibition. J Med Chem. Apr. 21, 2005;48(8):3080-4.
Fernandes et al., JNK2 and JNK3 are major regulators of axonal injury-induced retinal ganglion cell death. Neurobiol Dis. May 2012;46(2):393-401. doi: 10.1016/j.nbd.2012.02.003. Epub Feb. 14, 2012.
Fernandez et al., Neovascularization produced by angiotensin I.Journal of Laboratory and Clinical Medicine 1985;105(2):141-5.
Filippakopoulos et al., Selective inhibition of BET bromodomains. Nature. Dec. 23, 2010;468(7327):1067-73.
Finn et al., Dasatinib, an orally active small molecule inhibitor of both the src and abl kinases, selectively inhibits growth of basal-type/“triple-negative” breast cancer cell lines growing in vitro. Breast Cancer Res Treat. Nov. 2007;105(3):319-26. Epub Feb. 1, 2007.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-38.
Garnett et al., Guilty as charged: B-RAF is a human oncogene Cancer Cell. Oct. 2004;6(4):313-9.
GenBank Accession No. M80629. Lapidot-Lifson et al., Dec. 31, 1994. 2 pages.
GenBank Accession No. NP_001790. Yang et al., Oct. 6, 2016. 4 pages.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hirai et al., The c-Jun N-terminal kinase activator dual leucine zipper kinase regulates axon growth and neuronal migration in the developing cerebral cortex. J Neurosci. Nov. 15, 2006;26(46): 11992-2002.
Hla et al., Human cyclooxygenase-2 cDNA. Proceedings of the National Academy of Sciences 1992;89(16):7384-8.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.

(56) References Cited

OTHER PUBLICATIONS

Itoh et al., Impaired regenerative response of primary sensory neurons in ZPK/DLK gene-trap mice. Biochem Biophys Res Commun. May 29, 2009;383(2):258-62. doi: 10.1016/j.bbrc.2009.04.009. Epub Apr. 7, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kaldis et al., Analysis of CAK activities from human cells. Eur J Biochem. Jul. 2000;267(13):4213-21.
Kanakaraj et al., Interleukin (IL)-1 receptor-associated kinase (IRAK) requirement for optimal induction of multiple IL-1 signaling pathways and IL-6 production. J Exp Med. Jun. 15, 1998;187(12):2073-9.
Kantarjian et al., Dasatinib versus imatinib in newly diagnosed chronic-phase chronic myeloid leukemia. N Engl J Med. Jun. 17, 2010;362(24):2260-70.
Kauraniemi et al., New amplified and highly expressed genes discovered in the ERBB2 amplicon in breast cancer by cDNA microarrays. Cancer Res. Nov. 15, 2001;61(22):8235-40.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Larochelle et al., Requirements for Cdk7 in the assembly of Cdk1/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3): 142-55. doi: 10.1021/cb700248m.
Lee et al., BRAF mutations in non-Hodgkin's lymphoma. Br J Cancer. Nov. 17, 2003;89(10):1958-60.
Li et al., Identification of novel pyrrolopyrazoles as protein kinase C β II inhibitors. Bioorg Med Chem Lett. Jan. 1, 2011;21(1):584-7. doi: 10.1016/j.bmcl.2010.10.032. Epub Oct. 13, 2010.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Lorenzo et al., Expression of proto-oncogene c-kit in high risk prostate cancer. Eur J Surg Oncol. Nov. 2004;30(9):987-92.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
March, Advanced Organic Chemistry Reactions, Mechanisms and Structure. 4th ed. 1992:383-386.
Marelli et al., Tumor targeting via integrin ligands. Front. Oncol., Aug. 30, 2013. https://doi.org/10.3389/fonc.2013.00222.
Marques et al., A new subfamily of high molecular mass CDC2-related kinases with PITAI/VRE motifs. Biochem Biophys Res Commun. Dec. 29, 2000;279(3):832-7.
Matsuyama et al., Activation of Discoidin Domain Receptor 1 Isoform b with Collagen Up-Regulates Chemokine Production in Human Macrophages: Role of p38 Mitogen-Activated Protein Kinase and NF-κb. J Immunol Feb. 15, 2004, 172 (4) 2332-2340; DOI: https://doi.org/10.4049/jimmunol.172.4.2332.
Mukaiyama et al., The unexpected and the unpredictable in organic synthesis. Tetrahedron Jul. 1999;55(29):8609-70.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Obenauf et al., Therapy-induced tumour secretomes promote resistance and tumour progression. Nature. Apr. 16, 2015;520(7547):368-72. doi: 10.1038/nature14336. Epub Mar. 25, 2015.
Ochiana et al., The human Aurora kinase inhibitor danusertib is a lead compound for anti-trypanosomal drug discovery via target repurposing. Eur J Med Chem. Apr. 2013;62:777-84. doi: 10.1016/j.ejmech.2012.07.038. Epub Jul. 31, 2012.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Peifer et al., Small-molecule inhibitors of PDK1. ChemMedChem. Dec. 2008;3(12):1810-38. doi: 10.1002/cmdc.200800195.
Pevarello et al., 3-Amino-1,4,5,6-tetrahydropyrrolo[3,4-c]pyrazoles: A new class of CDK2 inhibitors. Bioorg Med Chem Lett. Feb. 15, 2006;16(4):1084-90.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.

(56) References Cited

OTHER PUBLICATIONS

PubChem-CID-68365059. Available at https://pubchem.ncbi.nlm.nih.gov/compound/68365059. Accessed Jun. 17, 2016.
Roberts et al., Antiangiogenic and antitumor activity of a selective PDGFR tyrosine kinase inhibitor, CP-673,451. Cancer Res. Feb. 1, 2005;65(3):957-66.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Rubin et al., KIT activation is a ubiquitous feature of gastrointestinal stromal tumors. Cancer Res. Nov. 15, 2001;61(22):8118-21.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Seed et al., The Inhibition of colon-26 Adenocarcinoma Development and Angiogenesis by Topical Diclofenac in 2.5% Hyaluronan. Cancer Research 1997;57:1625-9.
Sengupta et al., DLK induces developmental neuronal degeneration via selective regulation of proapoptotic JNK activity. Journal of Cell Biology 2011;194(5):751-764. DOI https://doi.org/10.1083/jcb.201103153.
Serizawa et al., Association of Cdk-activating kinase subunits with transcription factor TFIIH. Nature. Mar. 15, 1995;374(6519):280-2.
Sharma et al., A chromatin-mediated reversible drug-tolerant state in cancer cell subpopulations. Cell. Apr. 2, 2010;141(1):69-80.
Shiekhattar et al., Cdk-activating kinase complex is a component of human transcription factor TFIIH. Nature. Mar. 16, 1995;374(6519):283-7.
Shin et al., Dual leucine zipper kinase is required for retrograde injury signaling and axonal regeneration. Neuron. Jun. 21, 2012;74(6):1015-22. doi: 10.1016/j.neuron.2012.04.028.
Smith et al., Recent advances in the research and development of RAF kinase inhibitors. Curr. Top Med. Chem. 2006; 6(11):1071-89.
Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.
Srivastava et al., Augmentation of therapeutic responses in melanoma by inhibition of IRAK-1,-4. Cancer Res. Dec. 1, 2012;72(23):6209-16. doi: 10.1158/0008-5472.CAN-12-0337. Epub Oct. 4, 2012.
Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.
Sun et al. Inhibition of the transcriptional kinase CDK7 overcomes therapeutic resistance in HER2-positive breast cancers. Oncogene. 2020;39(1):50-63. doi:10.1038/s41388-019-0953-9.
Takemori et al., Inactivation of HDAC5 by SIK1 in AICAR-treated C2C12 myoblasts. Endocr J. 2009;56(1):121-30. Epub Oct. 22, 2008.
Terai et al., Activation of the FGF2-FGFR1 autocrine pathway: a novel mechanism of acquired resistance to gefitinib in NSCLC. Mol Cancer Res. Jul. 2013;11(7):759-67.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsujii et al., Cyclooxygenase regulates angiogenesis induced by colon cancer cells. Cell. May 29, 1998;93(5):705-16.
Uniprot No. Q9NYV4. Last modified Mar. 15, 2017. 14 pages.
Wang et al., IRAK-4 inhibitors for inflammation. Curr Top Med Chem. 2009;9(8):724-37.
Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.
Wellbrock et al., The RAF proteins take centre stage Nat Rev Mol Cell Biol. Nov. 2004;5(11):875-85.
Wietek et al., IRAK-4: a new drug target in inflammation, sepsis, and autoimmunity. Mol Interv. Jul. 2002;2(4):212-5.
Williamson et al., Structure-guided design of pyrazolo[1,5-a]pyrimidines as inhibitors of human cyclin-dependent kinase 2. Bioorg Med Chem Lett. Feb. 15, 2005;15(4):863-7.
Xin et al., Peroxisome proliferator-activated receptor gamma ligands are potent inhibitors of angiogenesis in vitro and in vivo. Journal of Biological Chemistry 1996;274(13):9116-21.
Yalpani, Cholesterol Lowering Drugs. Chemistry and Industry Feb. 1996;3:85-89.
Yasuda et al., The stem cell factor/c-kit receptor pathway enhances proliferation and invasion of pancreatic cancer cells. Mol Cancer. Oct. 18, 2006;5:46.
Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
Zarei et al. Tumors with TSC mutations are sensitive to CDK7 inhibition through NRF2 and glutathione depletion. J Exp Med. 2019;216(11):2635-2652. doi:10.1084/jem.20190251.
Zebisch et al., Back to the roots: the remarkable RAF oncogene story Cell Mol Life Sci. Jun. 2006;63(11):1314-30.
Zeng et al. Targeting MYC dependency in ovarian cancer through inhibition of CDK7 and CDK12/13. Elife. 2018;7:e39030. Published Nov. 13, 2018. doi: 10.7554/eLife.39030.
Zhang et al.CDK7 Inhibition Potentiates Genome Instability Triggering Anti-tumor Immunity in Small Cell Lung Cancer. Cancer Cell. 2020;37(1):37-54.e9. doi:10.1016/j.ccell.2019.11.003.
Zhang et al., Discovery of potent and selective covalent inhibitors of JNK. Chem Biol. Jan. 27, 2012;19(1):140-54. doi: 10.1016/j.chembiol.2011.11.010.
Zhou et al., Novel mutant-selective EGFR kinase inhibitors against EGFR T790M. Nature. Dec. 24, 2009;462(7276):1070-4.
Ziche et al., Role of prostaglandin E1 and copper in angiogenesis. Journal of the National Cancer Institute 1982;69(2):475.
International Search Report and Written Opinion for PCT/US2013/065708, mailed Feb. 4, 2014.
International Preliminary Report on Patentability for PCT/US2013/065708, mailed Apr. 30, 2015.
International Search Report and Written Opinion for PCT/US2014/061232, mailed Dec. 23, 2014.
International Search Report and Written Opinion for PCT/US2015/027312, mailed Jul. 10, 2015.
International Preliminary Report on Patentability for PCT/US2015/027312, mailed Nov. 3, 2016.
Extended European Search Report for EP 15873803.9 mailed on Apr. 12, 2018.
International Search Report and Written Opinion for PCT/US2015/000297, mailed Mar. 4, 2016.
International Preliminary Report on Patentability PCT/US2015/000297, mailed Jul. 6, 2017.
Partial Supplementary Search Report for EP 16808476.2, mailed on Mar. 7, 2019.
Extended European Search Report for EP 16808476.2, mailed on Jun. 14, 2019.
International Search Report and Written Opinion for PCT/US2016/037086, mailed Sep. 2, 2016.
International Preliminary Report on Patentability for PCT/US/2016/037086, mailed Dec. 21, 2017.
Partial European Search Report for EP 16773870.7, dated Jul. 12, 2018.
Extended European Search Report for EP 16773870.7, mailed on Oct. 17, 2018.
Invitation to Pay Additional Fees for PCT/US2016/024345, mailed Aug. 9, 2016.

(56) References Cited

OTHER PUBLICATIONS

International Search Report and Written Opinion for PCT/US2016/024345, mailed Oct. 6, 2016.
International Preliminary Report on Patentability for PCT/US2016/024345, mailed Oct. 12, 2017.
Extended European Search Report for EP 16815401.1, mailed on Jan. 17, 2019.
International Search Report and Written Opinion for PCT/US2016/39312, mailed Sep. 27, 2016.
International Preliminary Report on Patentability for PCT/US2016/39312, mailed Jan. 4, 2018.
Extended European Search Report for EP 16815397.1, mailed on Nov. 22, 2018.
International Search Report and Written Opinion for PCT/US16/39302, mailed Sep. 27, 2016.
International Preliminary Report on Patentability for PCT/US2016/39302, mailed Jan. 4, 2018.
Extended European Search Report for EP 16845194.6, mailed on Mar. 19, 2019.
Extended European Search Report for EP 21193645.5, mailed on May 11, 2022.
Invitation to Pay Additional Fees for PCT/US2016/051118, mailed Dec. 1, 2016.
International Search Report and Written Opinion for PCT/US2016/051118, mailed Mar. 13, 2017.
International Preliminary Report on Patentability for PCT/US2016/051118, mailed Mar. 22, 2018.
Extended European Search Report for EP 19826764.3 mailed on May 23, 2022.
Invitation to Pay Additional Fees for PCT/US2019/038677, mailed Aug. 13, 2019.
International Search Report and Written Opinion for PCT/US2019/038677, mailed Oct. 2, 2019.
International Preliminary Report on Patentability PCT/US2019/038677, mailed Jan. 7, 2021.
Extended European Search Report for EP 19903185.7 mailed on Aug. 5, 2022.
Extended European Search Report for EP 20843441.5 mailed on Dec. 12, 2023.
Invitation to Pay Additional Fees for PCT/US2020/043132, mailed Sep. 17, 2020.
International Search Report and Written Opinion for PCT/US2020/043132, mailed Dec. 10, 2020.
International Preliminary Report on Patentability for PCT/US2020/043132, mailed Feb. 3, 2022.
Extended European Search Report for EP 20908219.7 mailed on Dec. 12, 2023.
International Search Report and Written Opinion for PCT/US2020/065267, mailed Mar. 26, 2021.
International Preliminary Report on Patentability for PCT/US2020/065267, mailed Jul. 7, 2022.
[No Author Listed], CAS Registry No. 1347879-84-8. Entered STN: Dec. 4, 2011. 1 page.
[No Author Listed], CAS Registry No. 1349030-04-1. Entered STN: Dec. 5, 2011. 1 page.
[No Author Listed], GenBank: M80629.1. Human cdc2-related protein kinase (CHED) mRNA, complete cds. Entered Dec. 13, 1994.
[No Author Listed], NCBI Reference Sequence: NP_001790.1. cyclin-dependent kinase 7 isoform 1 [*Homo sapiens*]. Entered Apr. 1, 2018.
[No Author Listed], Uniprot No. Q9NYV4. Cyclin-dependent kinase 12. Gene CDK12. *Homo sapiens* (Human). Entered Dec. 1, 2000.
Barf et al., Irreversible protein kinase inhibitors: balancing the benefits and risks. J Med Chem. Jul. 26, 2012;55(14):6243-62. doi: 10.1021/jm3003203. Epub Jun. 8, 2012.
Brasca et al., Optimization of 6,6-dimethyl pyrrolo[3,4-c]pyrazoles: Identification of PHA-793887, a potent CDK inhibitor suitable for intravenous dosing. Bioorg Med Chem. Mar. 1, 2010;18(5):1844-53. doi: 10.1016/j.bmc.2010.01.042. Epub Jan. 25, 2010. PMID: 20153204.
Camilli et al., Phosphoinositides as regulators in membrane traffic. Science. Mar. 16, 1996;271(5255):1533-9.
Carmi et al., Novel irreversible epidermal growth factor receptor inhibitors by chemical modulation of the cysteine-trap portion. J Med Chem. Mar. 11, 2010;53(5):2038-50. doi: 10.1021/jm901558p.
CAS Registry No. 1025964-63-9 Entered STN: Jun. 6, 2008.
CAS Registry No. 1026531-51-0 Entered STN: Jun. 8, 2008.
CAS Registry No. 1026878-26-1 Entered STN: Jun. 10, 2008.
CAS Registry No. 1026975-11-0 Entered STN: Jun. 10, 2008.
CAS Registry No. 1027155-85-6 Entered STN: Jun. 11, 2008.
CAS Registry No. 1028288-20-1 Entered STN: Jun. 15, 2008.
CAS Registry No. 1347533-63-4 Entered STN: Dec. 2, 2011.
CAS Registry No. 1347548-09-7 Entered STN: Dec. 2, 2011.
CAS Registry No. 1609787-73-6 Entered STN: Jun. 6, 2014.
CAS Registry No. 1702381-29-0 Entered STN: May 13, 2015.
CAS Registry No. 1702381-42-7 Entered STN: May 13, 2015.
CAS Registry No. 1702381-64-3 Entered STN: May 13, 2015.
CAS Registry No. 1702381-71-2 Entered STN: May 13, 2015.
CAS Registry No. 1702381-78-9 Entered STN: May 13, 2015.
CAS Registry No. 1702809-46-8 Entered STN: May 13, 2015.
CAS Registry No. 1703051-55-1 Entered STN: May 13, 2015.
CAS Registry No. 1703051-60-8 Entered STN: May 13, 2015.
CAS Registry No. 1703051-61-9 Entered STN: May 13, 2015.
CAS Registry No. 1703051-63-1 Entered STN: May 13, 2015.
CAS Registry No. 1998741-41-5 Entered STN: Sep. 23, 2016.
CAS Registry No. 1998741-43-7 Entered STN: Sep. 23, 2016.
CAS Registry No. 956025-12-0 Entered STN: Nov. 27, 2007.
Choong et al., A diaminocyclohexyl analog of SNS-032 with improved permeability and bioavailability properties. Bioorg Med Chem Lett. Nov. 1, 2008;18(21):5763-5. doi: 10.1016/j.bmcl.2008.09.073. Epub Sep. 24, 2008. PMID: 18842409.
Database Registry Chemical Abstracts Service, Columbus, Ohio. Accession No. RN 1025874-73-0. Entered STN on Jun. 5, 2008.
Database Registry Chemical Abstracts Service, Columbus, Ohio. Accession No. RN 1205276-48-7, 1205371-13-6. Entered STN on Feb. 10, 2010.
Devegowda et al., Novel 6-N-arylcarboxamidopyrazolo[4,3-d]pyrimidin-7-one derivatives as potential anti-cancer agents. Bioorg Med Chem Lett. Mar. 1, 2010;20(5):1630-3. doi: 10.1016/j.bmcl.2010.01.029. Epub Jan. 20, 2010.
Dorée et al., The cyclin-dependent protein kinases and the control of cell division. FASEB J. Nov. 1994;8(14):1114-21. doi: 10.1096/fasebj.8.14.7958616.
Emerling et al., Depletion of a putatively druggable class of phosphatidylinositol kinases inhibits growth of p53-null tumors. Cell. Nov. 7, 2013;155(4):844-57. doi: 10.1016/j.cell.2013.09.057.
Ferguson et al., Synthesis and structure activity relationships of a series of 4-amino-1H-pyrazoles as covalent inhibitors of CDK14. Bioorg Med Chem Lett. Aug. 1, 2019;29(15):1985- 1993. doi: 10.1016/j.bmcl.2019.05.024. Epub May 23, 2019.
Fruman et al., Phosphoinositide Kinases. Annual Review of Biochemistry 1998;67(1):481-507.
Gu et al., Upregulated PFTK1 promotes tumor cell proliferation, migration, and invasion in breast cancer. Med Oncol. Jul. 2015;32(7):195. doi: 10.1007/s12032-015-0641-8. Epub Jun. 2, 2015.
Hazlitt et al., Development of Second-Generation CDK2 Inhibitors for the Prevention of Cisplatin-Induced Hearing Loss. J Med Chem. Sep. 13, 2018;61(17):7700-7709. doi: 10.1021/acs.jmedchem.8b00669. Epub Aug. 24, 2018. PMID: 30091915; PMCID: PMC6443376.
Hellvard et al., Inhibition of CDK9 as a therapeutic strategy for inflammatory arthritis. Sci Rep. Aug. 11, 2016;6:31441. doi: 10.1038/srep31441.
Leung et al., A novel interplay between oncogenic PFTK1 protein kinase and tumor suppressor TAGLN2 in the control of liver cancer cell motility. Oncogene. Nov. 3, 2011;30(44):4464-75. doi: 10.1038/onc.2011.161. Epub May 16, 2011.

(56) References Cited

OTHER PUBLICATIONS

Liu et al., Cyclin Y regulates the proliferation, migration, and invasion of ovarian cancer cells via Wnt signaling pathway. Tumour Biol. Aug. 2016;37(8):10161-75. doi: 10.1007/s13277-016- 4818-3. Epub Jan. 29, 2016.

Liu et al., Targeting the phosphoinositide 3-kinase pathway in cancer. Nat Rev Drug Discov. Aug. 2009;8(8):627-44. doi: 10.1038/nrd2926.

Malumbres et al., CDK inhibitors in cancer therapy: what is next? Trends Pharmacol Sci. Jan. 2008;29(1):16-21. doi: 10.1016/j.tips.2007.10.012. Epub Dec. 4, 2007.

Martin, Phosphoinositide lipids as signaling molecules: common themes for signal transduction, cytoskeletal regulation, and membrane trafficking. Annu Rev Cell Dev Biol. 1998;14:231-64.

McMahon, VEGF receptor signaling in tumor angiogenesis. Oncologist. 2000;5 Suppl 1:3-10. doi: 10.1634/theoncologist.5-suppl_1-3.

Mikhail et al., Cyclin-dependent kinase inhibitors and the treatment of gastrointestinal cancers. Am J Pathol. May 2015;185(5):1185-97. doi: 10.1016/j.ajpath.2015.01.008. Epub Mar. 5, 2015.

Olson et al. Development of a Selective CDK7 Covalent Inhibitor Reveals Predominant Cell-Cycle Phenotype. Cell Chem Biol. Jun. 20, 2019;26(6):792-803.e10. doi: 10.1016/j.chembiol.2019.02.012. Epub Mar. 21, 2019. PMID: 30905681.

Ou-Yang et al., Cyclin-Dependent Kinase 14 Promotes Cell Proliferation, Migration and Invasion in Ovarian Cancer by Inhibiting Wnt Signaling Pathway. Gynecol Obstet Invest. 2017;82(3):230-239. doi: 10.1159/000447632. Epub Aug. 10, 2016.

Pang et al., Identification of PFTAIRE protein kinase 1, a novel cell division cycle-2 related gene, in the motile phenotype of hepatocellular carcinoma cells. Hepatology. Aug. 2007;46(2):436-45. doi: 10.1002/hep.21691.

Patricelli et al., Functional interrogation of the kinome using nucleotide acyl phosphates. Biochemistry. Jan. 16, 2007;46(2):350-8. doi: 10.1021/bi062142x.

Pinedo et al., Introduction: translational research: the role of VEGF in tumor angiogenesis. The Oncologist. Apr. 1, 2000;5(S1):1-2.

Rameh et al., A new pathway for synthesis of phosphatidylinositol-4,5-bisphosphate. Nature. Nov. 13, 1997;390(6656):192-6.

Schramp et al., Phosphoinositides I: Enzymes of Synthesis and Degradation, 2012, Chapter 2, PIP Kinases from the Cell Membrane to the Nucleus, p. 25.

Sun et al., PFTK1 interacts with cyclin Y to activate non-canonical Wnt signaling in hepatocellular carcinoma. Biochem Biophys Res Commun. Jun. 20, 2014;449(1):163-8. doi: 10.1016/j.bbrc.2014.05.002. Epub May 10, 2014.

Taneera et al., Expression profiling of cell cycle genes in human pancreatic islets with and without type 2 diabetes. Mol Cell Endocrinol. Aug. 15, 2013;375(1-2):35-42. doi: 10.1016/j.mce.2013.05.003. Epub May 22, 2013.

Urich et al., The design and synthesis of potent and selective inhibitors of Trypanosoma brucei glycogen synthase kinase 3 for the treatment of human african trypanosomiasis. J Med Chem. Sep. 25, 2014;57(18):7536-49. doi: 10.1021/jm500239b. Epub Sep. 8, 2014. Supplemental information included. 18 total pages.

Voss et al., Discovery and pharmacological characterization of a novel small molecule inhibitor of phosphatidylinositol-5-phosphate 4-kinase, type II, beta. Biochem Biophys Res Commun. Jul. 4, 2014;449(3):327-31. doi: 10.1016/j.bbrc.2014.05.024.

Zhang et al., PFTK1 regulates cell proliferation, migration and invasion in epithelial ovarian cancer. Int J Biol Macromol. Apr. 2016;85:405-16. doi: 10.1016/j.ijbiomac.2016.01.009. Epub Jan. 6, 2016.

* cited by examiner

INHIBITORS OF CYCLIN-DEPENDENT KINASE 7 AND USES THEREOF

RELATED APPLICATIONS

The present application is a national stage filing under 35 U.S.C. § 371 of International PCT Application PCT/US2019/068835, filed Dec. 27, 2019, which claims priority under 35 U.S.C. § 119 (e) to U.S. provisional application, U.S. Ser. No. 62/786,328, filed Dec. 28, 2018, each of which is incorporated herein by reference.

GOVERNMENT SUPPORT

This invention was made with government support under grant number W81XWH-16-1-0252 awarded by the Department of Defense. The government has certain rights in the invention.

BACKGROUND OF THE PRESENT DISCLOSURE

The members of the cyclin-dependent kinase (CDK) family play critical regulatory roles in cell proliferation. There are 20 known mammalian CDKs. CDK7 to CDK13 have been linked to transcription. CDK1, 2, 4, and 6 show association with the cell cycle. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression (Desai et al., "Effects of phosphorylation by CAK on cyclin binding by CDC2 and CDK2." *Mol. Cell Biol.* 15, 345-350 (1995); Kaldis et al., "Analysis of CAK activities from human cells." *Eur. J. Biochem.* 267, 4213-4221 (2000); Larochelle et al., "Requirements for CDK7 in the assembly of CDK1/cyclin B and activation of CDK2 revealed by chemical genetics in human cells." *Mol. Cell,* 25, 839-850 (2007)). In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation (Serizawa. et al., "Association of CDK-activating kinase subunits with transcription factor TFIIH." *Nature,* 374, 280-282 (1995); Shiekhattar et al., "CDK-activating kinase complex is a component of human transcription factor TFIIH." *Nature,* 374, 283-287 (1995); Drapkin et al., "Human cyclin-dependent kinase-activating kinase exists in three distinct complexes." *Proc. Natl. Acad. Sci. U.S.A.,* 93, 6488-6493 (1996); Liu. et al., "Two cyclin-dependent kinases promote RNA polymerase II transcription and formation of the scaffold complex." *Mol. Cell Biol.,* 24, 1721-1735 (2004); Akhtar et al., "TFIIH kinase places bivalent marks on the carboxy-terminal domain of RNA polymerase II." *Mol. Cell,* 34, 387-393 (2009); Glover-Cutter et al., "TFIIH-associated CDK7 kinase functions in phosphorylation of C-terminal domain Ser7 residues, promoter-proximal pausing, and termination by RNA polymerase II." *Mol. Cell Biol.,* 29, 5455-5464 (2009)). Together, the two functions of CDK7, i.e., CAK and CTD phosphorylation, may support critical facets of cellular proliferation, cell cycling, and transcription.

Disruption of RNAP II CTD phosphorylation has been shown to preferentially affect proteins with short half-lives, including those of the anti-apoptotic BCL-2 family (Konig et al., "The novel cyclin-dependent kinase inhibitor flavopiridol downregulates Bcl-2 and induces growth arrest and apoptosis in chronic B-cell leukemia lines." *Blood,* 1, 4307-4312 (1997); Gojo et al., "The cyclin-dependent kinase inhibitor flavopiridol induces apoptosis in multiple myeloma cells through transcriptional repression and down-regulation of Mcl-1." *Clin. Cancer Res.,* 8, 3527-3538 (2002)). Cancer cells have demonstrated the ability to circumvent pro-cell death signaling through up-regulation of BCL-2 family members (Llambi et al., "Apoptosis and oncogenesis: give and take in the BCL-2 family." *Curr. Opin. Genet. Dev.,* 21, 12-20 (2011)). Therefore, inhibition of human CDK7 kinase activity is likely to result in anti-proliferative activity, and pharmacological inhibition is thought to be useful in treating proliferative disorders, including cancer. Flavopiridol, a non-selective pan-CDK inhibitor that targets CTD kinases, has demonstrated efficacy for the treatment of chronic lymphocytic leukemia (CLL) but suffers from a poor toxicity profile (Lin et al., "Phase II study of flavopiridol in relapsed chronic lymphocytic leukemia demonstrating high response rates in genetically high-risk disease." *J. Clin. Oncol.,* 27, 6012-6018 (2009); Christian et al., "Flavopiridol in chronic lymphocytic leukemia: a concise review." *Clin. Lymphoma Myeloma,* 9 Suppl. 3, S179-S185 (2009)). There remains a need for the treatment of CLL and other cancers with CDK inhibitors.

SUMMARY OF THE PRESENT DISCLOSURE

The present disclosure provides, in one aspect, compounds of Formula (I):

(I)

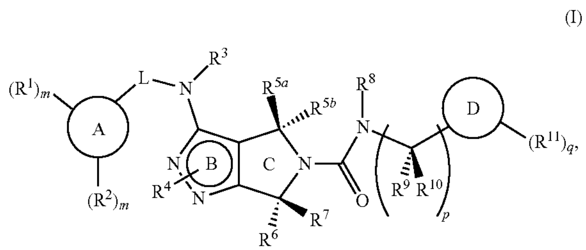

and pharmaceutically acceptable salts, solvates, hydrates, polymorphs, co-crystals, tautomers, stereoisomers, isotopically labeled derivatives, or prodrugs thereof, wherein $R^1$, m, $R^2$, n, Ring A, L, $R^3$, Ring B, $R^4$, $R^{5a}$, $R^{5b}$, $R^6$, $R^7$, $R^8$, $R^9$, $R^{10}$, p, Ring D, $R^{11}$, and q are as defined herein. The compounds of the present disclosure may inhibit the activity of kinases. In certain embodiments, the kinase is a cyclin-dependent kinase (CDK) (e.g., CDK7). The compounds of the present disclosure may be useful in inhibiting the activity of the kinases, inhibiting the growth of a cell, and/or inducing apoptosis of a cell. In certain embodiments, the cell (e.g., the cell affected by the compound or contacted with the compound) is a malignant cell or premalignant cell. In certain embodiments, the cell is in vivo or in vitro. Kinases are implicated in a range of diseases (e.g., proliferative diseases, cystic fibrosis) in subjects. The compounds of the present disclosure may also be useful in treating and/or preventing diseases in subjects in need thereof.

The compounds of the present disclosure may be selective for inhibiting the activity of a CDK (e.g., CDK7) over other kinases (e.g., kinases other than CDKs, kinases other than CDK7). In certain embodiments, the compounds of the present disclosure are selective for inhibiting the activity of CDK7 over CDK2, CDK9, and/or CDK12. The compounds of the present disclosure may be advantageous over non-selective or less selective kinase inhibitors in treating and/or preventing a disease in a subject in need thereof. The compounds of the present disclosure may be more selective for inhibiting the activity of a CDK (e.g., CDK7) over other kinases (e.g., kinases other than CDKs, kinases other than CDK7) than other compounds (e.g., non-selective kinase inhibitors, less selective kinase inhibitors). Compared to other compounds, the compounds of the present disclosure may also be more potent, more efficacious, and/or less toxic, and/or may decrease the frequency of side effects, decrease the severity of side effects, increase subject compliance, and/or decrease resistance, when used in treating and/or preventing a disease in a subject in need thereof. Moreover, the compounds of the present disclosure may be more soluble, more permeable, more microsomally stable, and/or more bioavailable, and/or may show improved pharmacokinetic properties compared to other compounds. The compounds of the present disclosure include carbocyclyl or heterocyclyl as Ring D. Without wishing to be bound by any particular theory, Ring D may contribute to one or more of the above advantages of the compounds of the present disclosure over certain other compounds. Moreover, certain compounds of the present disclosure may be able to covalently modify the cysteine residue Cys312 of CDK7. Cys312 of CDK7 is unique as compared to other CDKs and certain other kinases. Without wishing to be bound by any particular theory, the ability of certain compounds to covalently modify Cys312 of CDK7 may contribute to one or more of the above advantages of these compounds over certain other compounds.

Exemplary compounds of the present disclosure include:

-continued

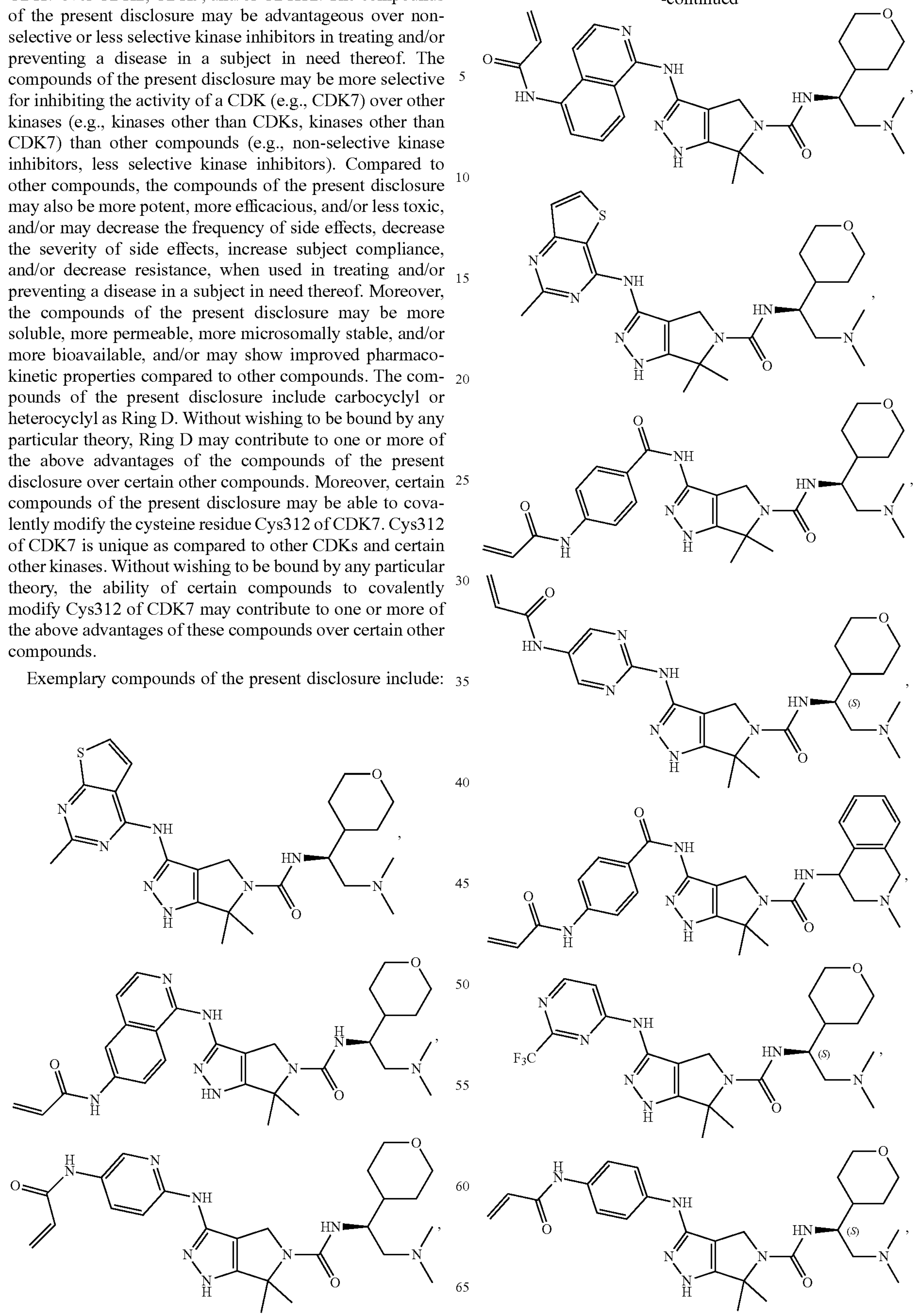

-continued

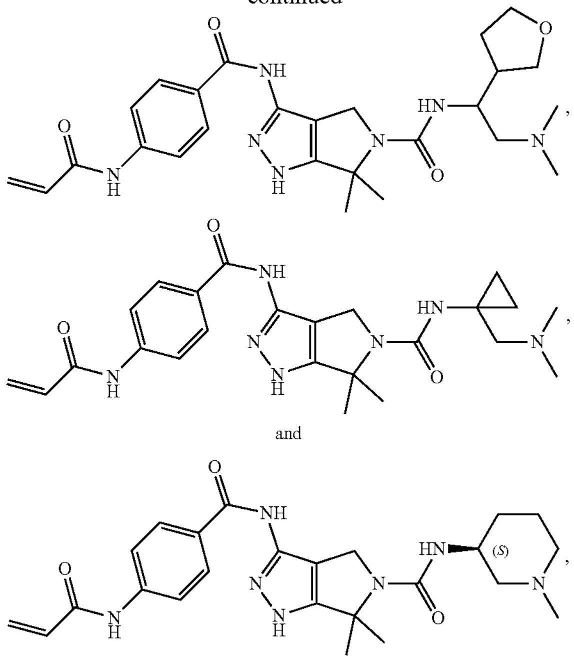

and pharmaceutically acceptable salts, solvates, hydrates, polymorphs, co-crystals, tautomers, stereoisomers, isotopically labeled derivatives, and prodrugs thereof.

In another aspect, the present disclosure provides pharmaceutical compositions including a compound of the present disclosure, and optionally a pharmaceutically acceptable excipient. In certain embodiments, the pharmaceutical compositions include an effective amount of the compound. In certain embodiments, the pharmaceutical compositions include an additional pharmaceutical agent.

In another aspect, the present disclosure provides kits comprising a compound or pharmaceutical composition of the present disclosure; and instructions for using the compound or pharmaceutical composition. In certain embodiments, the instructions comprise prescribing information.

In another aspect, the present disclosure provides methods of treating a disease in a subject in need thereof, the methods comprising administering to the subject in need thereof an effective amount of a compound or pharmaceutical composition of the present disclosure.

In another aspect, the present disclosure provides methods of preventing a disease in a subject in need thereof, the methods comprising administering to the subject in need thereof an effective amount of a compound or pharmaceutical composition of the present disclosure.

In certain embodiments, the disease (e.g., disease treated and/or prevented by a method of the present disclosure) is a proliferative disease (e.g., cancer, benign neoplasm, a disease associated with angiogenesis, inflammatory disease, autoinflammatory disease, autoimmune disease).

In another aspect, the present disclosure provides methods of inhibiting the activity of a kinase in a subject, biological sample, tissue, or cell, the method comprising administering to the subject or contacting the biological sample, tissue, or cell with an effective amount of a compound or pharmaceutical composition of the present disclosure. In certain embodiments, the kinase (e.g., kinase whose activity is inhibited by the compound and pharmaceutical composition) is a CDK (e.g., CDK7).

In another aspect, the present disclosure provides methods of inhibiting the growth of a cell, the method comprising contacting the cell with an effective amount of a compound or pharmaceutical composition of the present disclosure.

In another aspect, the present disclosure provides methods of inducing apoptosis of a cell, the method comprising contacting the cell with an effective amount of a compound or pharmaceutical composition of the present disclosure.

In another aspect, the present disclosure provides methods of down-regulating the transcription of MYC or MCL-1 in a subject, biological sample, tissue, or cell, the methods comprising administering to the subject or contacting the biological sample, tissue, or cell with an effective amount of a compound or pharmaceutical composition of the present disclosure.

In certain embodiments, the cell is an abnormally proliferative cell (e.g., malignant cell or premalignant cell).

In another aspect, the present disclosure provides uses (e.g., uses in the methods of the present disclosure) of the compounds and pharmaceutical compositions of the present disclosure.

The details of one or more embodiments of the present disclosure are set forth herein. Other features, objects, and advantages of the present disclosure will be apparent from the Detailed Description, the Examples, the Figures, and the Claims.

Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987. The disclosure is not intended to be limited in any manner by the exemplary listing of substituents described herein.

Compounds of the present disclosure can comprise one or more asymmetric centers, and thus can exist in various isomeric forms, e.g., enantiomers and/or diastereomers. For example, the compounds of the present disclosure can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 196; and Wilen, *Tables of Resolving Agents and Optical Resolutions* p. 268 (E. L. Eliel, Ed., Univ. of Notre Dame Press, Notre Dame, IN 197. The disclosure additionally encompasses compounds of the present disclosure as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, CM, $C_{1-3}$, $C_{1-2}$, $C_{2-6}$, $C_{2-5}$, CM, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$— cyclopentyl, n-hexyl, sec-hexyl, cyclohexyl, —$CH_2$-cyclohexyl moieties and the like, which again, may bear one or more substituents. Alkenyl groups include for example, ethenyl, propenyl, butenyl, l-methyl-2-buten-1-yl, and the like. Representative alkynyl groups include ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl (C, propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$). In certain embodiments, the alkyl group is a substituted $C_{1-10}$ alkyl (such as substituted $C_{1-6}$ alkyl, e.g., —$CF_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl (C, 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C═C double bond for which the stereochemistry is not specified (e.g., —CH═$CHCH_3$ or

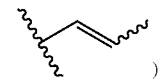

) may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl (C, 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered, non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups, wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered, monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent linking groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —C(═O)$R^{aa}$, —$CO_2H$, —CHO, —$C(OR^{cc})_2$, —$CO_2R^{aa}$, —OC(═O)$R^{aa}$, —$OCO_2R^{aa}$, —C(═O)$N(R^{bb})_2$, —OC(═O)$N(R^{bb})_2$, —$NR^{bb}$C(═O)$R^{aa}$, —$NR^{bb}CO_2R^{aa}$, —$NR^{bb}$C(═O)$N(R^{bb})_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)$N(R^{bb})_2$, —OC(═$NR^{bb}$)$N(R^{bb})_2$, —$NR^{bb}$C(═$NR^{bb}$)$N(R^{bb})_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —$Si(R^{aa})_3$, —$OSi(R^{aa})_3$—C(═S)$N(R^{bb})_2$, —C(═O)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$_2R^{aa}$, —OP(═O)$_2R^{aa}$, —P(═O)$(R^{aa})_2$, —OP(═O)$(R^{aa})_2$, —OP(═O)$(OR^{cc})_2$, —P(═O)$_2N(R^{bb})_2$, —OP(═O)$_2N(R^{bb})_2$, —P(═O)$(NR^{bb})_2$, —OP(═O)$(NR^{bb})_2$, —$NR^{bb}$P(═O)$(OR^{cc})_2$, —$NR^{bb}$P(═O)$(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group ═O, ═S, ═$NN(R^{bb})_2$, ═$NNR^{bb}$C(═O)$R^{aa}$, ═$NNR^{bb}$C(═O)$OR^{aa}$, ═$NNR^{bb}$S(═O)$_2R^{aa}$, ═$NR^{bb}$, or ═$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$_2R^{aa}$, —P(═O)$(R^{aa})_2$, —P(═O)$_2N(R^{cc})_2$, —P(═O)$(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+R^{ee}$, —$N(OR^{ee})R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}$C(═$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$_2$R$^{ee}$, —P(═O)(R$^{ee}$)$_2$, —OP(═O)(R$^{ee}$)$_2$, —OP(═O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form ═O or ═S;

each instance of R$^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —$NO_2$, —$N_3$, —$SO_2H$, —$SO_3H$, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)$^+X^-$, —$NH_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(═O)($C_{1-6}$ alkyl), —$CO_2H$, —$CO_2$($C_{1-6}$ alkyl), —OC(═O)($C_{1-6}$ alkyl), —O$CO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —NH$CO_2$($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)O$C_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(═NH)$NH_2$, —NH$SO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2$O$C_{1-6}$ alkyl, —O$SO_2C_{1-6}$ alkyl, —S$OC_{1-6}$ alkyl, —Si($C_{1-6}$ alkyl)$_3$, —OSi($C_{1-6}$ alkyl)$_3$-C(═S)N($C_{1-6}$ alkyl)$_2$, C(═S)NH($C_{1-6}$ alkyl), C(═S)$NH_2$, —C(═O)S($C_{1-6}$ alkyl), —C(═S)S$C_{1-6}$ alkyl, —SC(═S)S$C_{1-6}$ alkyl, —P(═O)$_2$($C_{1-6}$ alkyl), —P(═O)($C_{1-6}$ alkyl)$_2$, —OP(═O)($C_{1-6}$ alkyl)$_2$, —OP(═O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form ═O or ═S; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(═O)R$^{aa}$, —CHO, —$CO_2$R$^{aa}$, —C(═O)N(R$^{bb}$)$_2$, —C(═NR$^{bb}$)R$^{aa}$, —C(═NR$^{bb}$)OR$^{aa}$, —C(═NR$^{bb}$)N(R$^{bb}$)$_2$, —C(═O)NR$^{bb}$$SO_2$R$^{aa}$, —C(═S)N(R$^{bb}$)$_2$, —C(═O)SR$^{aa}$, or —C(═S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include hydrogen, —OH, —OR$^{aa}$, —N(R$^{cc}$)$_2$, —CN, —C(═O)R$^{aa}$, —C(═O)N(R$^{cc}$)$_2$, —$CO_2$R$^{aa}$, —$SO_2$R$^{aa}$, —C(═NR$^{bb}$)R$^{aa}$, —C(═NR$^{cc}$)OR$^{aa}$, —C(═NR$^{cc}$)N(R$^{cc}$)$_2$, —$SO_2$N(R$^{cc}$)$_2$, —$SO_2$R$^{cc}$, —$SO_2$OR$^{cc}$, —SOR$^{aa}$, —C(═S)N(R$^{cc}$)$_2$, —C(═O)SR$^{cc}$, —C(═S)SR$^{cc}$, —P(═O)$_2$R$^{aa}$, —P(═O)(R$^{aa}$)$_2$, —P(═O)$_2$N(R$^{cc}$)$_2$, —P(═O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include —OH, —OR$^{aa}$, —N(R$^{cc}$)$_2$, —C(═O)R$^{aa}$, —C(═O)N(R$^{cc}$)$_2$, —$CO_2$R$^{aa}$, —$SO_2$R$^{aa}$, —C(═NR$^{cc}$)R$^{aa}$, —C(═NR$^{cc}$)OR$^{aa}$, —C(═NR$^{cc}$)N(R$^{cc}$)$_2$, —$SO_2$N(R$^{cc}$)$_2$, —$SO_2$R$^{cc}$, —$SO_2$OR$^{cc}$, —SOR$^{aa}$, —C(═S)N(R$^{cc}$)$_2$, —C(═O)SR$^{cc}$, —C(═S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(═O)R$^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(═O)OR$^{aa}$) include methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidiny 1 carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, 5-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(═O)$_2$R$^{aa}$) include p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-5-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenyl methyl amine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N,N-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexanyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include —R$^{aa}$, —C(═O)SR$^{aa}$, —C(═O)R$^{aa}$, —CO$_2$R$^{aa}$, —C(═O)N(R$^{bb}$)$_2$, —C(═NR$^{bb}$)R$^{aa}$, —C(═NR$^{bb}$)OR$^{aa}$, —C(═NR$^{bb}$)N(R$^{bb}$)$_2$, —S(═O)R$^{aa}$, —SO$_2$R$^{aa}$, —Si(R$^{aa}$)$_3$, —P(R$^{cc}$)$_2$, —P(R$^{cc}$)$_3$, —P(═O)$_2$R$^{aa}$, —P(═O)(R$^{aa}$)$_2$, —P(═O)(OR$^{cc}$)$_2$, —P(═O)$_2$N(R$^{bb}$)$_2$, and —P(═O)(NR$^{bb}$)$_2$, wherein R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include methyl, t-butyloxycarbonyl (BOC or Boc), methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkylp-nitrobenzyl carbonate, alkyl 5-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include-$R^{aa}$, —C(=O)S$R^{aa}$, —C(=O)$R^{aa}$, —$CO_2R^{aa}$, —C(=O)N$(R^{bb})_2$, —C(=N$R^{bb}$)$R^{aa}$, —C(=N$R^{bb}$)O$R^{aa}$, —C(=N$R^{bb}$)N$(R^{bb})_2$, —S(=O)$R^{aa}$, —$SO_2R^{aa}$, —Si$(R^{aa})_3$, —P$(R^{cc})_2$, —P$(R^{cc})_3$, —P$(=O)_2R^{aa}$, —P(=O)$(R^{aa})_2$, —P(=O)$(OR^{cc})_2$, —P$(=O)_2$N$(R^{bb})_2$, and —P(=O)$(NR^{bb})_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

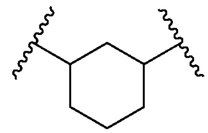 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_4$—). A hydrocarbon chain may also be unsaturated and include one or more C=C and/or C≡C bonds anywhere in the hydrocarbon chain. For instance, —CH=CH—$(CH_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

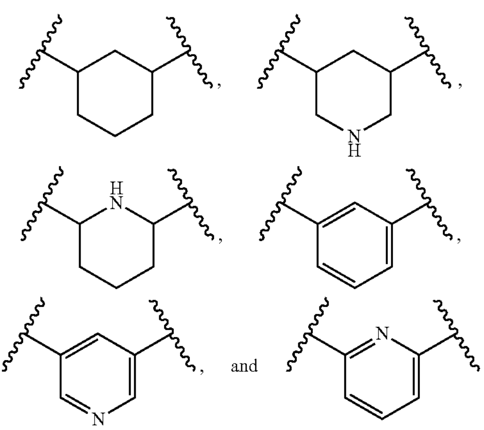

are all examples of a hydrocarbon chain. In contrast, in certain embodiments,

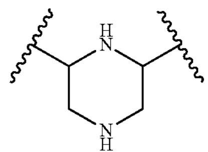

and

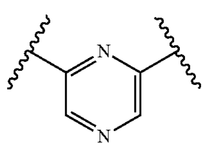

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

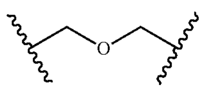 [SMILES: *COC*]

is a $C_3$ hydrocarbon chain wherein one chain atom is replaced with an oxygen atom.

The term "leaving group" is given its ordinary meaning in the art of synthetic organic chemistry and refers to an atom or a group capable of being displaced by a nucleophile. Examples of suitable leaving groups include halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), $—OS(=O)_2(CF_3CF_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R\cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R\cdot 0.5\ H_2O$)), and polyhydrates (x is a number greater than 1, e.g., dihydrates ($R\cdot 2\ H_2O$) and hexahydrates ($R\cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers".

When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal may contain a compound of the present disclosure and one or more other component, including atoms, ions, molecules, or solvent molecules. In certain embodiments, a co-crystal may contain a compound of the present disclosure and one or more components related to said compound, including an isomer, tautomer, salt, solvate, hydrate, synthetic precursor, synthetic derivative, fragment or impurity of said compound.

The term "isotopically labeled derivative" or "isotopically labeled" refers to a compound wherein one or more atoms in the compound (or in an associated ion or molecule of a salt, hydrate, or solvate) has been replaced with an isotope of the same element. For the given element or position in the molecule the isotope will be enriched, or present in a higher percentage of all atoms of the element or of all atoms at the position in the molecule in a sample, relative to an unlabeled variant. In certain embodiments, the enriched isotope will be a stable isotope. In certain embodiments, the enriched isotope will be an unstable or radioactive isotope (e.g., a radionuclide). In certain embodiments, the enriched isotope may be detected by a measurement technique, including to nuclear magnetic resonance, mass spectrometry, infrared spectroscopy, or a technique that measures radioactive decay.

The term "prodrugs" refers to compounds that have cleavable groups and become by solvolysis or under physiological conditions the compounds described herein, which are pharmaceutically active in vivo. Such examples include choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in an mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_6$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce, slow, halt or prevent activity of a particular biological process (e.g., activity of a cyclin-dependent kinase) in a cell relative to vehicle.

When a compound, pharmaceutical composition, method, use, or kit is referred to as "selectively," "specifically," or "competitively" binding a first protein or a first chromatin, the compound, pharmaceutical composition, method, use, or kit binds the first protein or the first chromatin with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or second chromatin that is different from the first protein and the first chromatin. When a compound, pharmaceutical composition, method, use, or kit is referred to as "selectively," "specifically," or "competitively" modulating (e.g., increasing or inhibiting) the activity of a cyclin-dependent kinase, the compound, pharmaceutical composition, method, use, or kit modulates the activity of the cyclin-dependent kinase to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the cyclin-dependent kinase.

The term "aberrant activity" refers to activity deviating from normal activity, that is, abnormal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from another biological sample.

The terms "administer," "administering," or "administration" refers to implanting, absorbing, ingesting, injecting, inhaling, or otherwise introducing a compound described herein, or a composition thereof, into, in, or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated as in the growth of normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include hematological malignancies. Additional exemplary cancers include acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC)); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "hematological malignancy" refers to tumors that affect blood, bone marrow, and/or lymph nodes. Exemplary hematological malignancies include leukemia, such as acute lymphoblastic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt's lymphoma, Waldenstrom's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hay fever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an aberrant immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases includeglomerulonephritis, Goodpasture's syndrome, necrotizing vasculitis, lymphadenitis, periarteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barre syndrome, Hashimoto's thyroiditis, and cardiomyopathy.

The term "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. Exemplary human protein kinases include AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK 10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK100, SgK196, SGK2, SgK223, SgK269, SgK288, SGK3, SgK307, SgK384ps, SgK396, SgK424, SgK493, SgK494, SgK495, SgK496, SIK (e.g., SIK1, SIK, skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The term "Src family kinase" refers to a family of non-receptor tyrosine protein kinases that includes nine members: SrcA subfamily that includes c-Src (proto-oncogene tyrosine-protein kinase Src), YES (proto-oncogene tyrosine-protein kinase Yes), FYN (proto-oncogene tyrosine-protein kinase FYN), and FGR (Gardner-Rasheed feline sarcoma viral (v-FGR) oncogene homolog); SrcB subfamily that includes LCK (lymphocyte-specific protein tyrosine kinase), HCK (tyrosine-protein kinase HCK, hemopoietic cell kinase), BLK (tyrosine-protein kinase BLK), and LYN (tyrosine-protein kinase LYN); and FRK (Fyn-related kinase).

The term "CDK" refers to a cyclin-dependent kinase. A CDK binds a cyclin (e.g., Cyclin H), which is a regulatory protein. CDKs phosphorylate their substrates at serines and threonines. CDKs include CDK1, CDK2, CDK3, CDK4, CDK5, CDK6, CDK7, CDK8, CDK9, CDK10, CDK11, CDK12, CDK13, CDK14, CDK15, CDK16, CDK17, CDK18, CDK19, and CDK20.

"CDK7" or "cyclin-dependent kinase 7" is a CDK, wherein the substrate is Cyclin H, MATI (e.g., MNAT1), or Cyclin H and MATE CDK7 is alternatively referred to as CAK1, HCAK, MO15, STK1, CDKN7, and p39MO15. Non-limiting examples of the nucleotide and protein sequences for human CDK7 are described in GenBank Accession Number NP_001790, incorporated herein by reference.

BRIEF DESCRIPTION OF THE DRAWINGS

The accompanying drawing, which are incorporated in and constitute a part of this specification, illustrate several embodiments of the present disclosure and together with the description, serve to explain the principles of the present disclosure.

DETAILED DESCRIPTION OF CERTAIN EMBODIMENTS OF THE PRESENT DISCLOSURE

Figure 1:
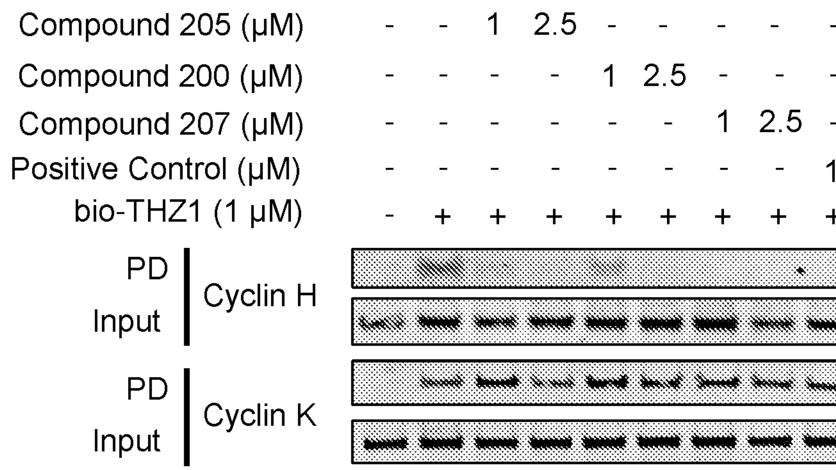
FIG. 1 shows exemplary results of a pull down assay of compounds 205, 200, and 207 at 1 and 2.5 μM. Experimental details are described elsewhere. Western blotting with cyclin H identifies CDK7-cyclin H complexes (CDK7), while western blotting with cyclin K identifies CDK12-cyclin K and CDK13-cyclin K complexes
Figure 2:
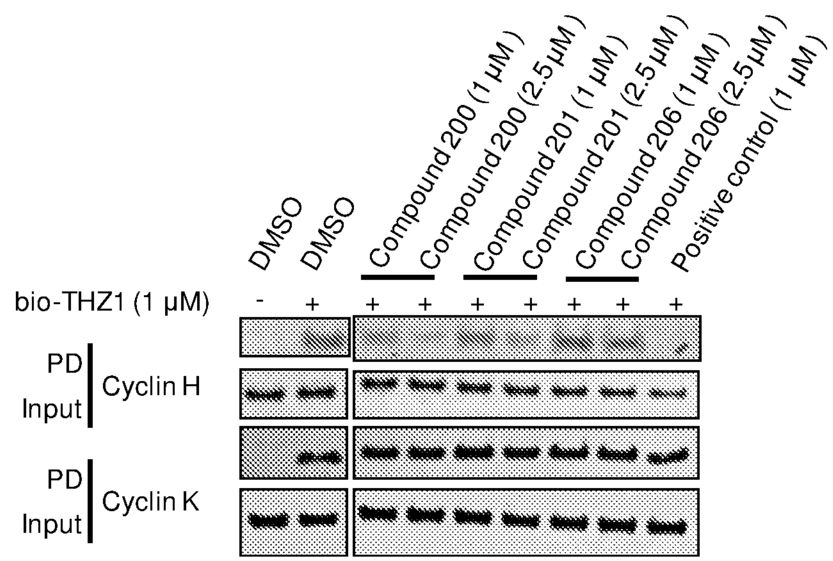
FIG. 2 shows exemplary results of a pull down assay of compounds 200, 201, and 206, at 1 and 2.5 μM. Experimental details are described elsewhere. Western blotting with cyclin H identifies CDK7-cyclin H complexes (CDK7), while western blotting with cyclin K identifies CDK12-cyclin K and CDK13-cyclin K complexes.
Figure 3:
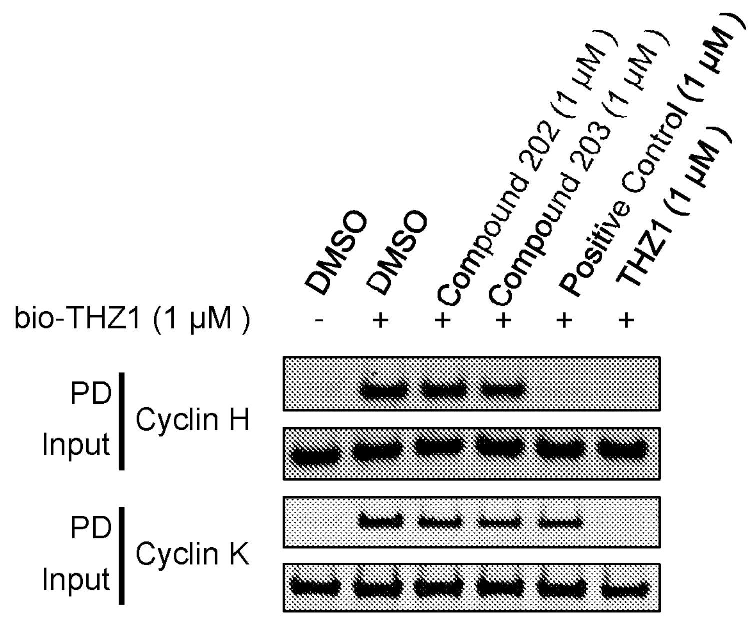
FIG. 3 shows exemplary results of a pull down assay of compounds 202 and 203 at 1 μM. Experimental details are described elsewhere. Western blotting with cyclin H identifies CDK7-cyclin H complexes (CDK7), while western blotting with cyclin K identifies CDK12-cyclin K and CDK13-cyclin K complexes.
Figure 4:
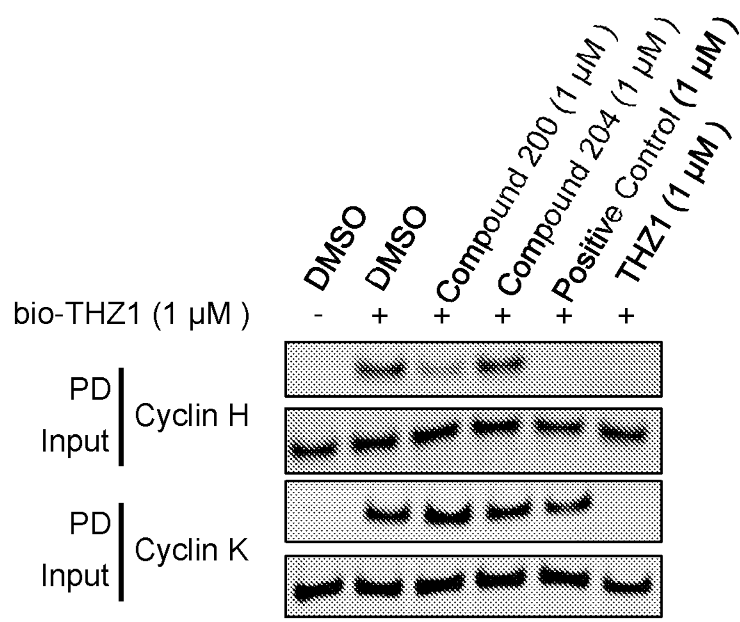
FIG. 4 shows exemplary results of a pull down assay of compounds 200 and 204 at 1 μM. Experimental details are described elsewhere. Western blotting with cyclin H identifies CDK7-cyclin H complexes (CDK7), while western blotting with cyclin K identifies CDK12-cyclin K and CDK13-cyclin K complexes
Figure 5:
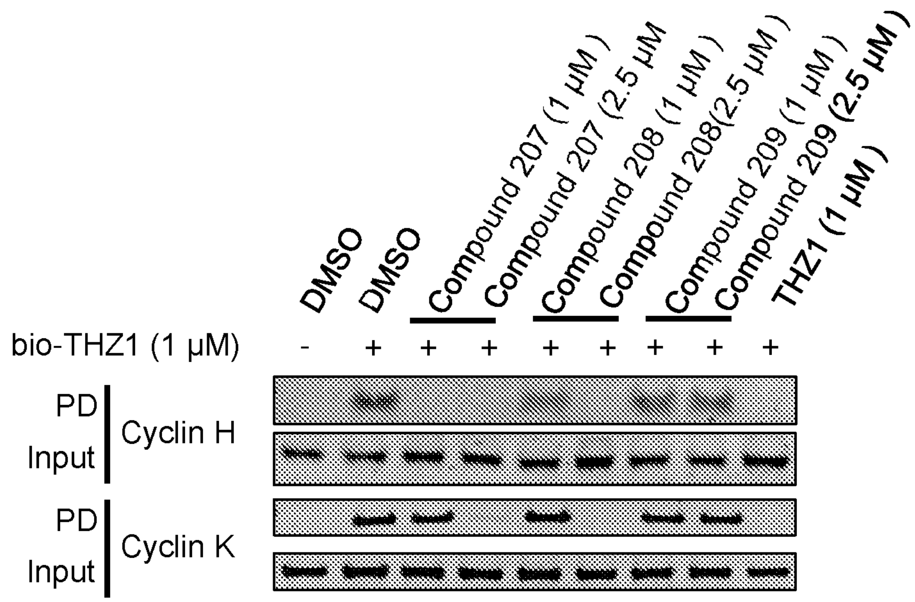
FIG. 5 shows exemplary results of a pull down assay of compounds 207, 208, and 209 at 1 and 2.5 μM. Experimental details are described elsewhere. Western blotting with cyclin H identifies CDK7-cyclin H complexes (CDK7), while western blotting with cyclin K identifies CDK12-cyclin K and CDK13-cyclin K complexes.

Kinases are implicated in a range of diseases. In particular, CDKs are key regulators of the cell cycle. Their successive activation and inactivation drives the cycle forward. The activity of CDKs is regulated by multiple mechanisms such as positive and negative phosphorylation, binding of regulatory proteins like cyclins, and CDK inhibitors. CDK7 plays a critical role in the regulation of RNA polymerase II-mediated transcription of protein-encoding genes. Disruption of CDK7 signaling may cause defects in transcription. The absence of selective inhibitors of CDK7 has hindered investigation of the transcriptional and functional consequences of acute and long-term inhibition of the activity of CDK7 under normal and pathological conditions.

The present disclosure provides, in one aspect, compounds of Formula (I), and pharmaceutically acceptable salts, solvates, hydrates, polymorphs, co-crystals, tautomers, stereoisomers, isotopically labeled derivatives, or prodrugs thereof. The compounds of the present disclosure may inhibit the activity of kinases. In certain embodiments, the kinase is a CDK. In certain embodiments, the kinase is CDK7. In certain embodiments, the kinase is CDK2, CDK9, or CDK12. The compounds of the present disclosure may be selective for inhibiting the activity of a kinase (e.g., CDK7) over certain other kinases (e.g., CDK2, CDK9, CDK12). Also provided are pharmaceutical compositions, kits, methods of use, and uses that involve the compounds of the present disclosure. The compounds, pharmaceutical compositions, kits, methods of use, and uses of the present disclosure may be useful in inhibiting the activity of a kinase, inhibiting the growth of a cell, and/or inducing apoptosis of a cell. The compounds, pharmaceutical compositions, kits, methods of use, and uses of the present disclosure may also be useful in treating diseases and/or preventing diseases. In certain embodiments, the disease is a proliferative disease (e.g., cancer, benign neoplasm, pathological angiogenesis, inflammatory disease, autoinflammatory disease, autoimmune disease) or cystic fibrosis.

Compounds

In one aspect, the present disclosure provides compounds of Formula (I):

(I)

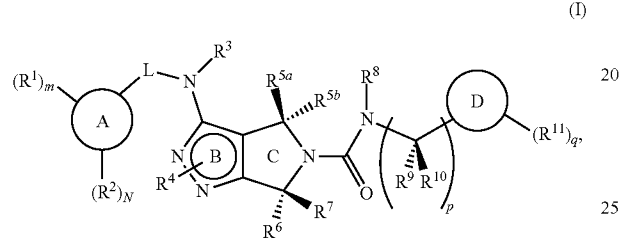

or a pharmaceutically acceptable salt, solvate, hydrate, polymorph, co-crystal, tautomer, stereoisomer, isotopically labeled derivative, or prodrug thereof, wherein:

Ring A is carbocyclyl, heterocyclyl, aryl, or heteroaryl;

$R^1$ is of the formula:

(i-1), (i-2), (i-3), (i-4)

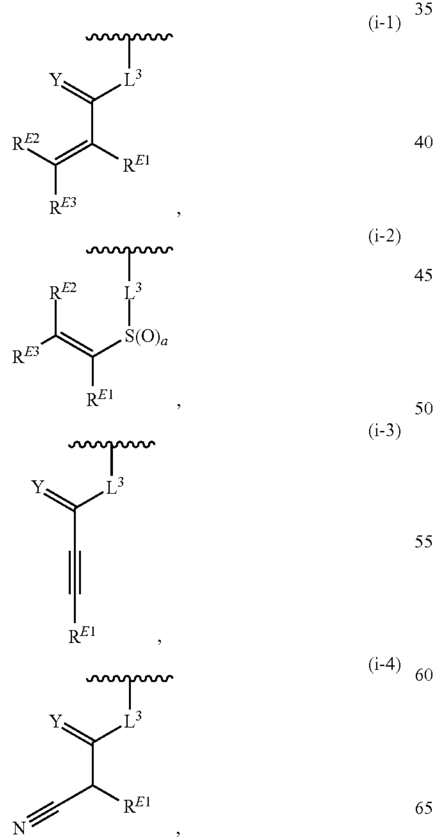

-continued (i-5)

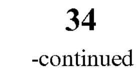

(i-6)

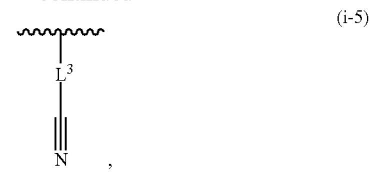

(i-7)

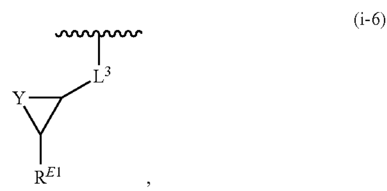

(i-8)

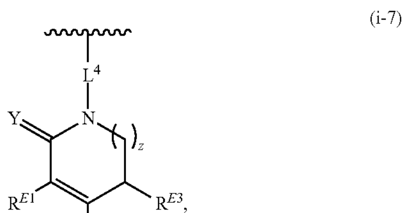

(i-9)

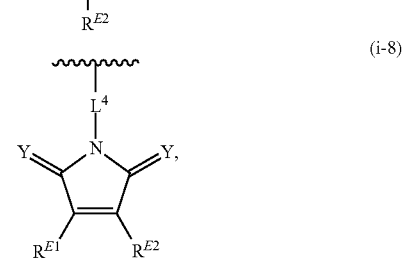

(i-10)

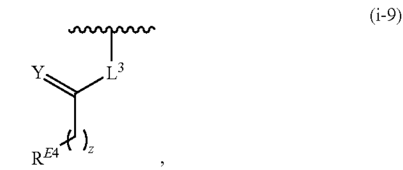

(i-11)

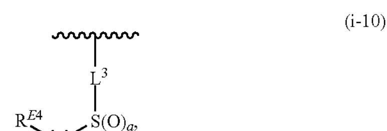

(i-12)

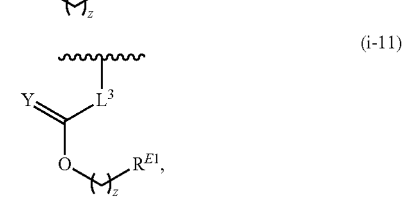

(i-13)

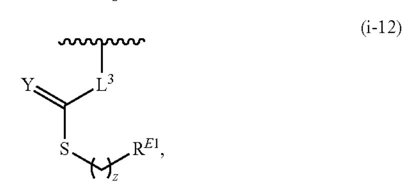

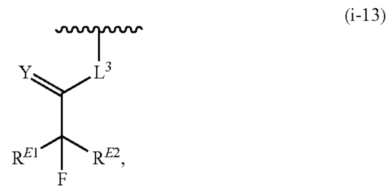

-continued
(i-14)
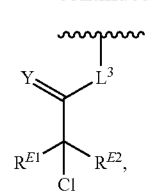
(i-15)
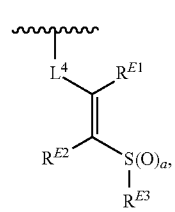
(i-16)
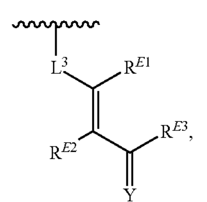
(i-17)
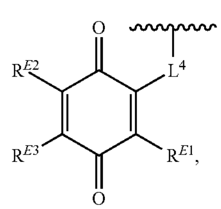
(i-18)
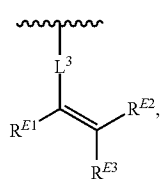
(i-19)
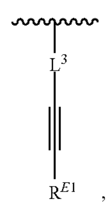
(i-20)
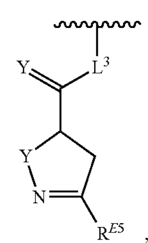
-continued
(i-21)
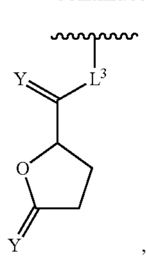
(i-22)
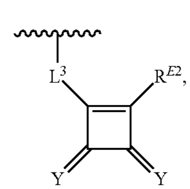
(i-23)
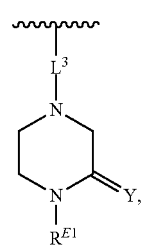
(i-24)
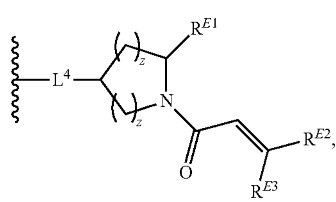
(i-25)
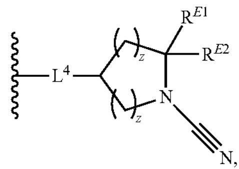
(i-26)
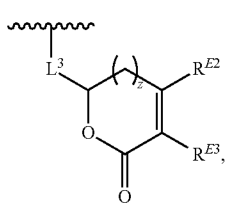
(i-27)
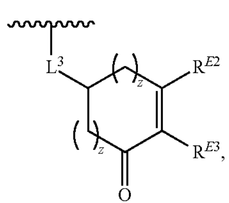

-continued

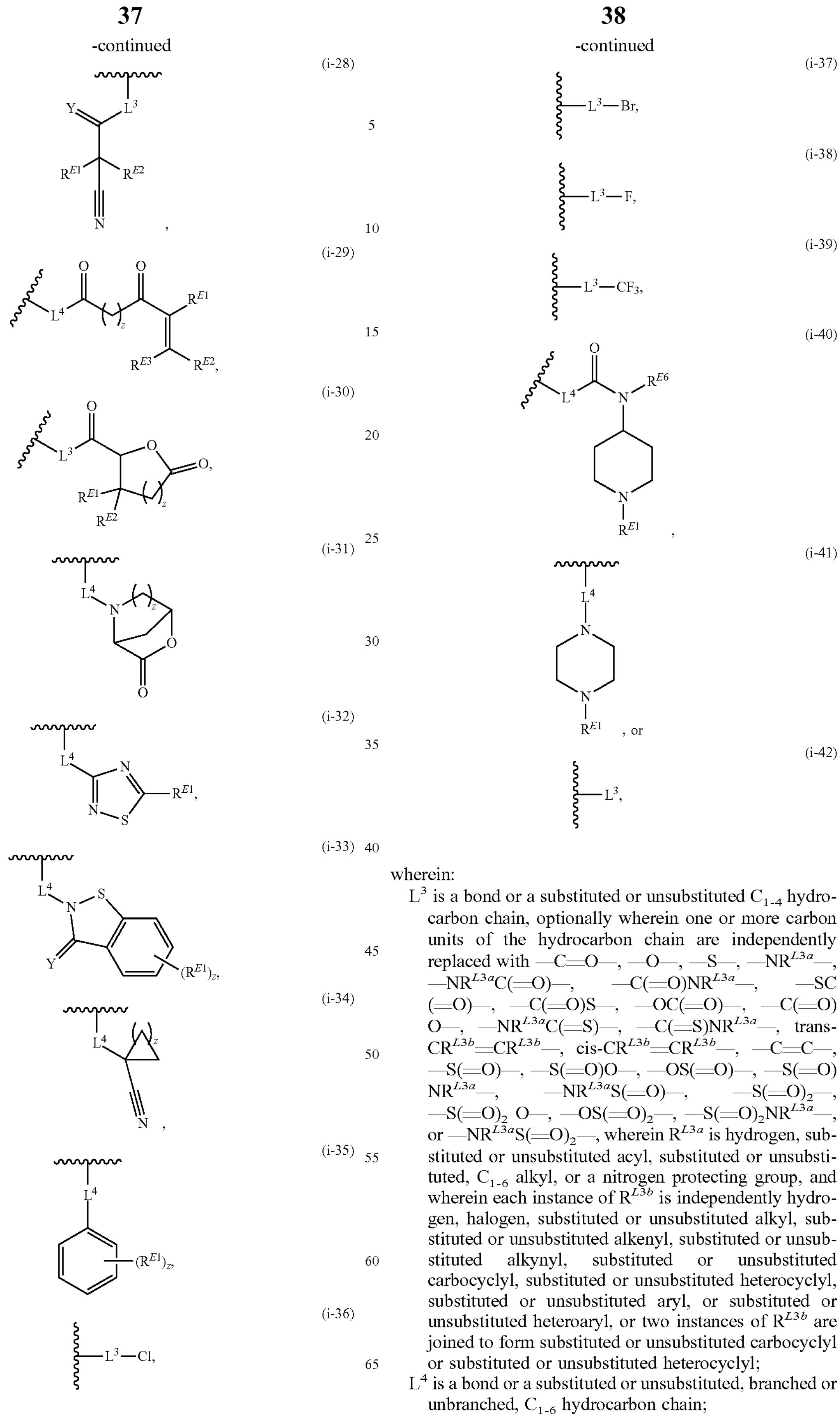

wherein:

$L^3$ is a bond or a substituted or unsubstituted $C_{1-4}$ hydrocarbon chain, optionally wherein one or more carbon units of the hydrocarbon chain are independently replaced with —C═O—, —O—, —S—, —$NR^{L3a}$—, —$NR^{L3a}$C(═O)—, —C(═O)$NR^{L3a}$—, —SC(═O)—, —C(═O)S—, —OC(═O)—, —C(═O)O—, —$NR^{L3a}$C(═S)—, —C(═S)$NR^{L3a}$—, trans-$CR^{L3b}$═$CR^{L3b}$—, cis-$CR^{L3b}$═$CR^{L3b}$—, —C≡C—, —S(═O)—, —S(═O)O—, —OS(═O)—, —S(═O)$NR^{L3a}$—, —$NR^{L3a}$S(═O)—, —S(═O)$_2$—, —S(═O)$_2$ O—, —OS(═O)$_2$—, —S(═O)$_2NR^{L3a}$—, or —$NR^{L3a}$S(═O)$_2$—, wherein $R^{L3a}$ is hydrogen, substituted or unsubstituted acyl, substituted or unsubstituted, $C_{1-6}$ alkyl, or a nitrogen protecting group, and wherein each instance of $R^{L3b}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two instances of $R^{L3b}$ are joined to form substituted or unsubstituted carbocyclyl or substituted or unsubstituted heterocyclyl;

$L^4$ is a bond or a substituted or unsubstituted, branched or unbranched, $C_{1-6}$ hydrocarbon chain;

each of $R^{E1}$, $R^{E2}$, and $R^{E3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —$CH_2OR^{EE}$, —$CH_2N(R^{EE})_2$, —$CH_2SR^{EE}$, —$OR^{EE}$, —$N(R^{EE})_2$, —$Si(R^{EE})_3$, or —$SR^{EE}$, wherein each instance of $R^{EE}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two instances of $R^{EE}$ are joined to form substituted or unsubstituted heterocyclyl;

or $R^{E1}$ and $R^{E3}$, or $R^{E2}$ and $R^{E3}$, or $R^{E1}$ and $R^{E2}$ are joined to form substituted or unsubstituted carbocyclyl or substituted or unsubstituted heterocyclyl;

$R^{E4}$ is a leaving group;

$R^{E5}$ is halogen;

$R^{E6}$ is hydrogen, substituted or unsubstituted, $C_{1-6}$ alkyl, or a nitrogen protecting group;

each instance of Y is independently O, S, or $NR^{E7}$, wherein $R^{E7}$ is hydrogen, substituted or unsubstituted, $C_{1-6}$ alkyl, or a nitrogen protecting group;

a is 1 or 2; and each instance of z is independently 0, 1, 2, 3, 4, 5, or 6, as valency permits;

m is 0 or 1;

each instance of $R^2$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

n is 0, 1, 2, 3, 4, 5, 6, 7, 8, 9, 10, or 11, as valency permits;

L is a single bond or —C(=O)—;

$R^3$ is hydrogen, substituted or unsubstituted acyl, substituted or unsubstituted alkyl, or a nitrogen protecting group;

$R^4$ is hydrogen, substituted or unsubstituted acyl, substituted or unsubstituted alkyl, or a nitrogen protecting group;

each of $R^{5a}$ and $R^{5b}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$, or $R^{5a}$ and $R^{5b}$ are joined to form substituted or unsubstituted carbocyclyl or substituted or unsubstituted heterocyclyl;

each instance of $R^6$ and $R^7$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$, or $R^6$ and $R^7$ are joined to form substituted or unsubstituted carbocyclyl or substituted or unsubstituted heterocyclyl;

$R^8$ is hydrogen, substituted or unsubstituted acyl, substituted or unsubstituted alkyl, or a nitrogen protecting group;

each instance of $R^9$ and $R^{10}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$, or $R^9$ and $R^{10}$ are joined to form substituted or unsubstituted carbocyclyl or substituted or unsubstituted heterocyclyl;

p is 0, 1, 2, 3, or 4;

Ring D is carbocyclyl or heterocyclyl;

each instance of $R^{11}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, —$OC(=O)N(R^a)_2$, or a nitrogen protecting group when attached to a nitrogen atom;

q is 0, 1, 2, 3, 4, 5, 6, 7, 8, 9, 10, or 11, as valency permits; and each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form substituted or unsubstituted heterocyclyl or substituted or unsubstituted heteroaryl;

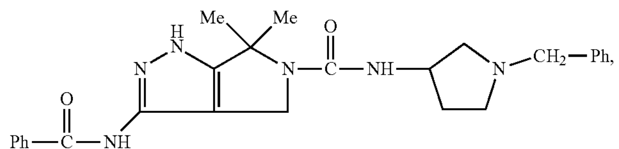

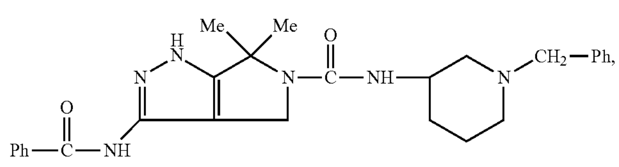

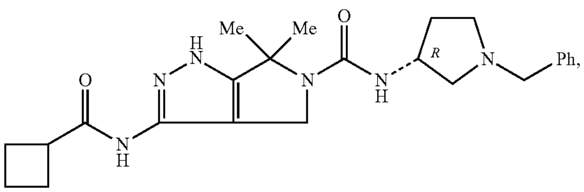

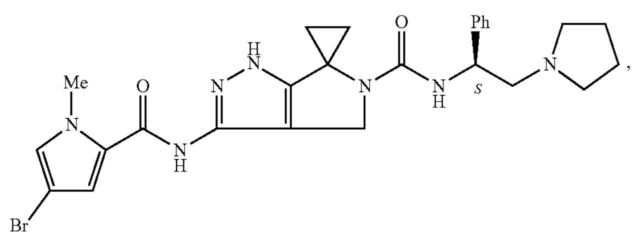

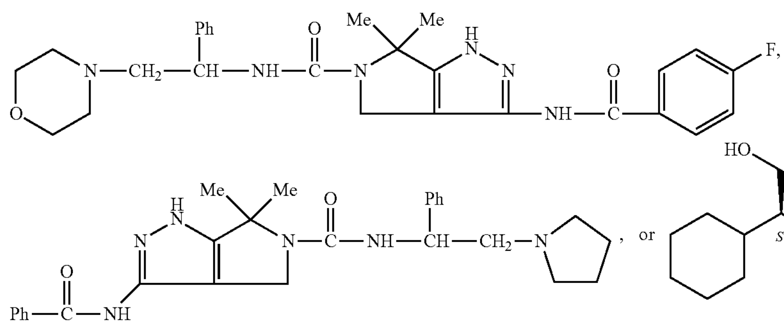

Formula (I) includes Ring A

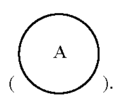

In certain embodiments, Ring A is carbocyclyl. In certain embodiments, Ring A is monocyclic, 3- to 7-membered carbocyclyl comprising 0, 1, or 2 double bonds in the carbocyclic ring system, as valency permits. In certain embodiments, Ring A is bicyclic, 5- to 13-membered carbocyclyl comprising 0, 1, 2, or 3 double bonds in the carbocyclic ring system, as valency permits. In certain embodiments, Ring A is cyclopropyl, cyclopentyl, cyclohexyl, or cycloheptyl. In certain embodiments, Ring A is cyclobutyl. In certain embodiments, Ring A is not cyclobutyl.

In certain embodiments, Ring A is heterocyclyl. In certain embodiments, Ring A is 3- to 7-membered, monocyclic heterocyclyl. In certain embodiments, Ring A is oxetanyl, tetrahydrofuranyl, tetrahydropyranyl, azetidinyl, pyrrolidinyl, piperidinyl, morpholinyl, or piperazinyl. In certain embodiments, Ring A is 5- to 13-membered, bicyclic heterocyclyl. In certain embodiments, Ring A is heterocyclyl, wherein the heteroatoms in the heterocyclic ring system are oxygen and/or nitrogen. In certain embodiments, Ring A is heterocyclyl, wherein the heteroatoms in the heterocyclic ring system are oxygen. In certain embodiments, Ring A is heterocyclyl, wherein the heteroatoms in the heterocyclic ring system are nitrogen.

In certain embodiments, Ring A is aryl. In certain embodiments, Ring A is phenyl. In certain embodiments, Ring A is naphthyl.

In certain embodiments, Ring A is heteroaryl. In certain embodiments, Ring A is monocyclic, 5- or 6-membered heteroaryl. In certain embodiments, Ring A is furanyl, thienyl, pyrrolyl, imidazolyl, oxazolyl, isoxazolyl, thiazolyl, or isothiazolyl. In certain embodiments, Ring A is pyridinyl. In certain embodiments, Ring A is

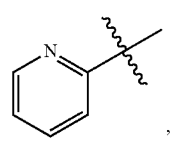 [SMILES: *c1ccccn1]

wherein the attachment point is attached to L. In certain embodiments, Ring A is

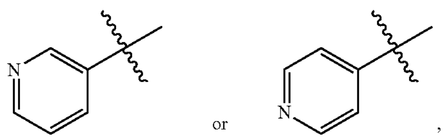 [SMILES: *c1cccnc1 ; *c1ccncc1]

wherein the attachment point is attached to L. In certain embodiments, Ring A is pyrimidinyl. In certain embodiments, Ring A is

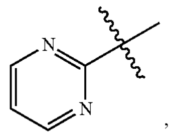 [SMILES: *c1ncccn1]

wherein the attachment point is attached to L. In certain embodiments, Ring A is

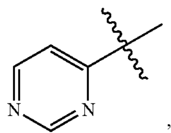 [SMILES: *c1ccncn1]

wherein the attachment point is attached to L.
In certain embodiments, Ring A is

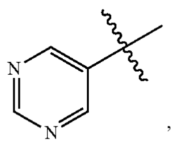 [SMILES: *c1cncnc1]

wherein the attachment point is attached to L. In certain embodiments, Ring A is pyrazinyl or pyridazinyl. In certain embodiments, Ring A is bicyclic, 9- or 10-membered (e.g., 5,6-fused, 6,5-fused, or 6,6-fused) heteroaryl. In certain embodiments, when Ring A is bicyclic, 9- or 10-membered heteroaryl, the monocyclic ring to which L is attached is monocyclic heteroaryl. In certain embodiments, when Ring A is bicyclic, 9- or 10-membered heteroaryl, the monocyclic ring to which L is attached is phenyl. In certain embodiments, Ring A is benzofuranyl, aza-benzofuranyl, diaza-benzofuranyl, benzothienyl, aza-benzothienyl, diaza-benzothienyl, indolyl, aza-indolyl, diaza-indolyl, isoindolyl, aza-isoindolyl, diaza-isoindolyl, benzoxazolyl, aza-benzoxazolyl, diaza-benzoxazolyl, benzothiazolyl, aza-benzothiazolyl, diaza-benzothiazolyl, benzimidazolyl, aza-benzimidazolyl, or diaza-benzimidazolyl. In certain embodiments, Ring A is thieno[2,3-d]pyrimidinyl or thieno[3,2-d]pyrimidinyl. In certain embodiments, Ring A is

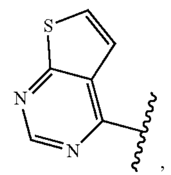 [SMILES: *c1ncnc2sccc12]

wherein the attachment point is attached to L. In certain embodiments, Ring A is

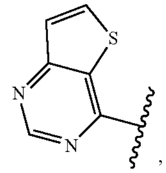 [SMILES: *c1ncnc2ccsc12]

wherein the attachment point is attached to L. In certain embodiments, Ring A is isoquinolinyl. In certain embodiments, Ring A is

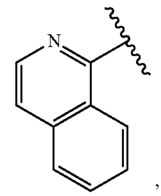 [SMILES: *c1nccc2ccccc12]

wherein the attachment point is attached to L. In certain embodiments, Ring A is aza-isoquinolinyl, diaza-isoquinolinyl, quinolinyl, aza-quinolinyl, or diaza-quinolinyl.

Ring A may include the substituent $R^1$. In certain embodiments,

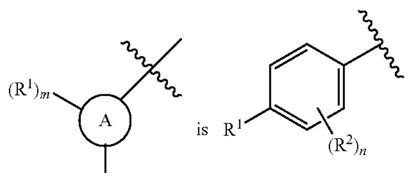

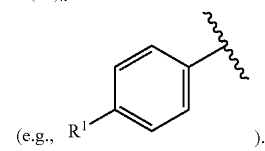

In certain embodiments,

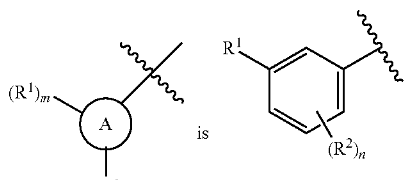

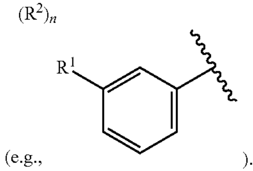

In certain embodiments,
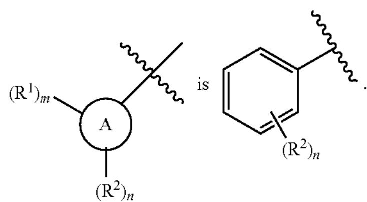
In certain embodiments,
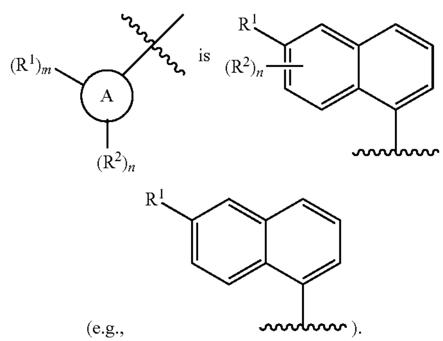
In certain embodiments,
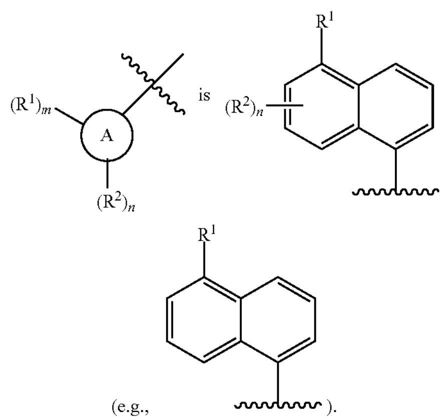
In certain embodiments,
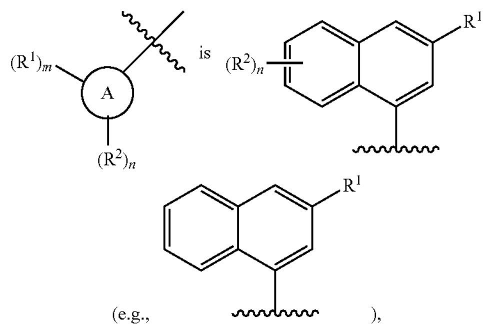
-continued
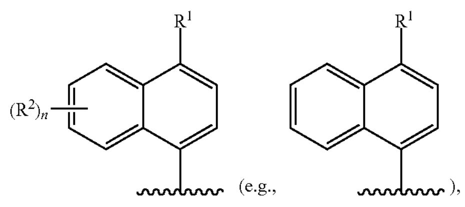
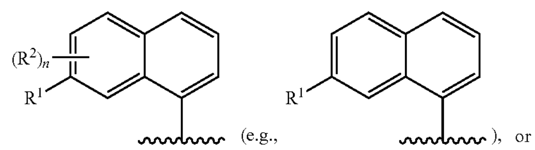
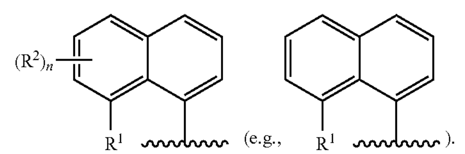
In certain embodiments,
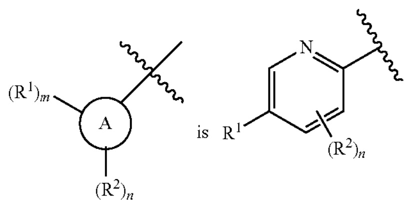
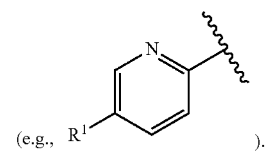
In certain embodiments,
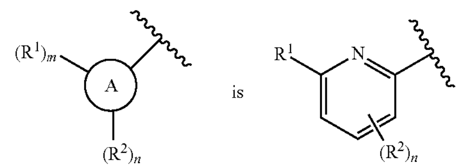
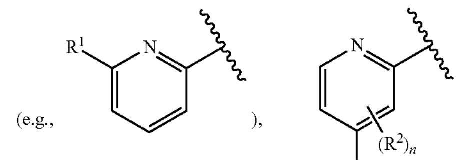
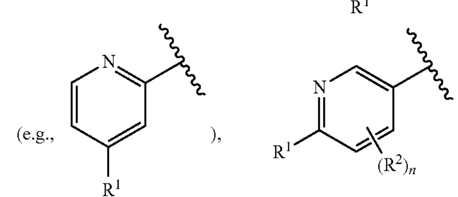

-continued
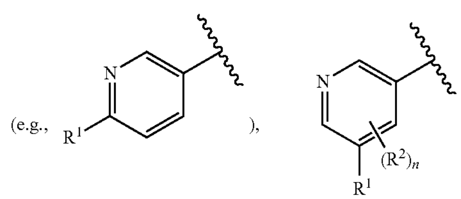
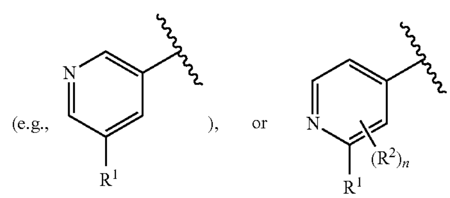
In certain embodiments,
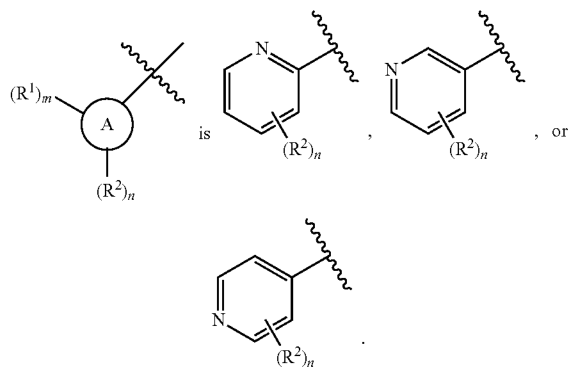
In certain embodiments,
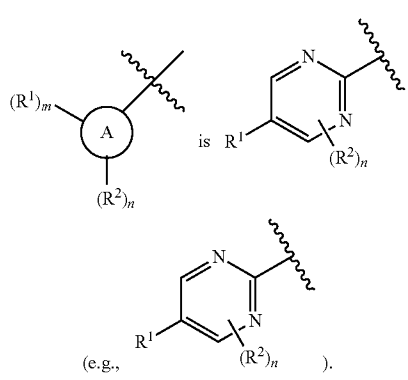
In certain embodiments,
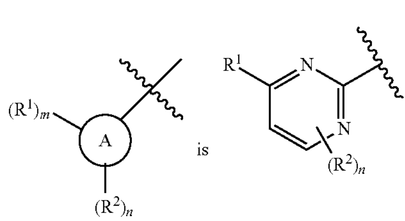
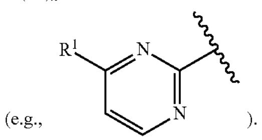
In certain embodiments,
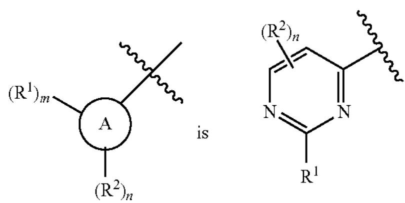
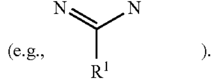
In certain embodiments,
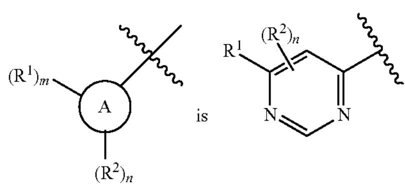
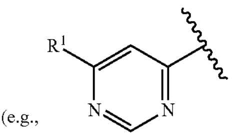
In certain embodiments,
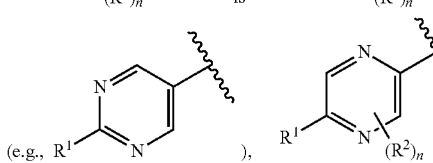

-continued
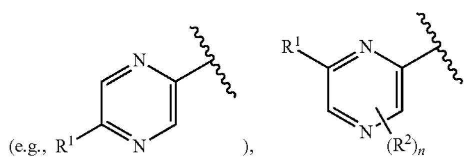
In certain embodiments,
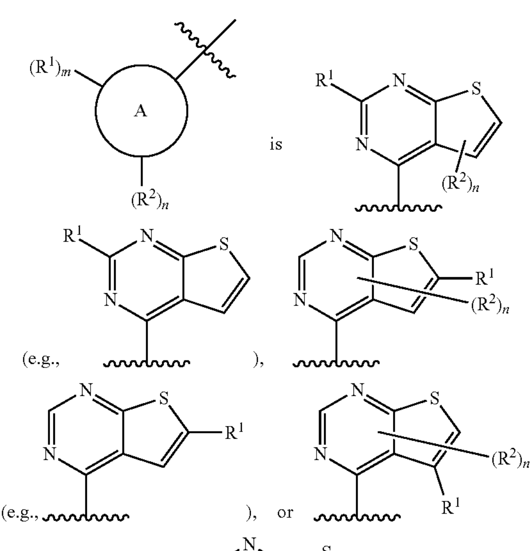
In certain embodiments,
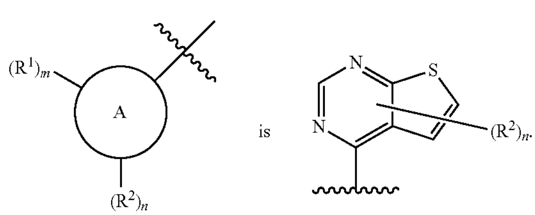
In certain embodiments,
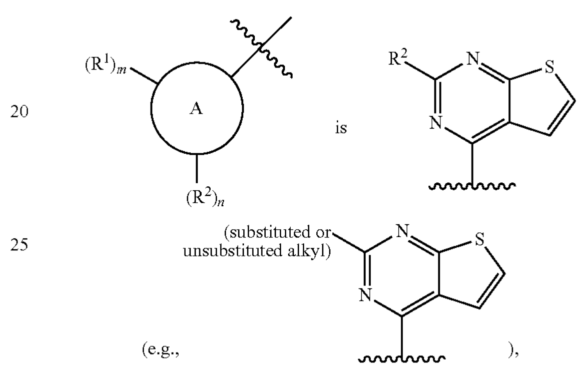
In certain embodiments,
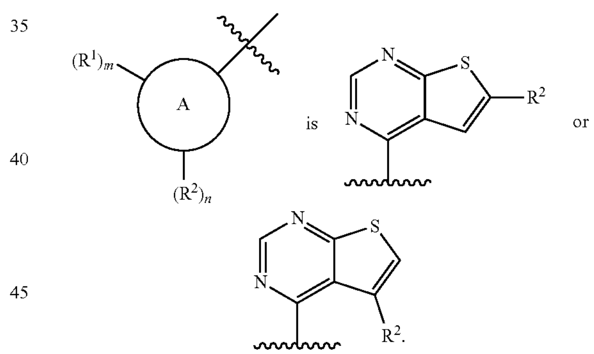
In certain embodiments,
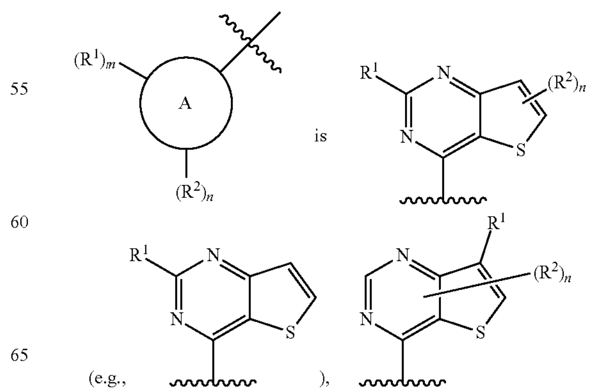

-continued
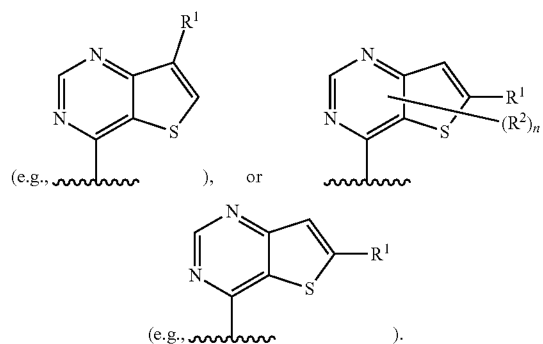
In certain embodiments,
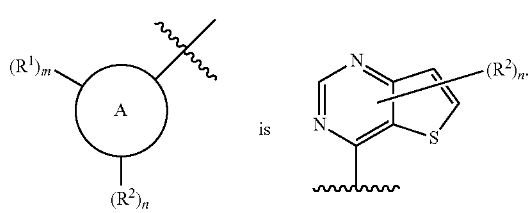
In certain embodiments,
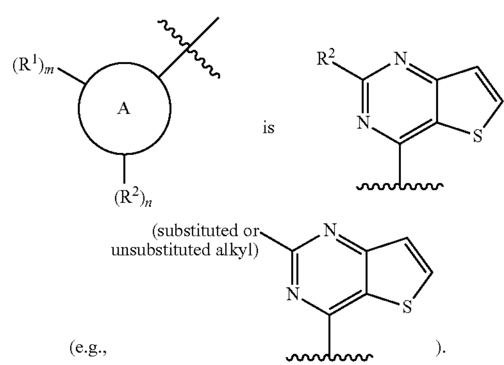
In certain embodiments,
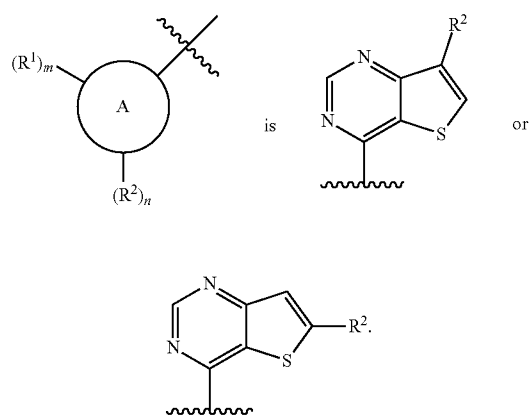
In certain embodiments,
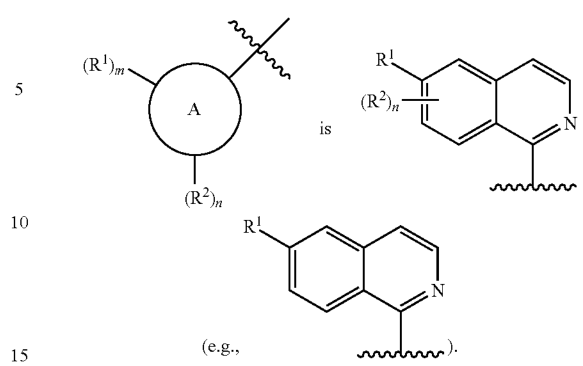
In certain
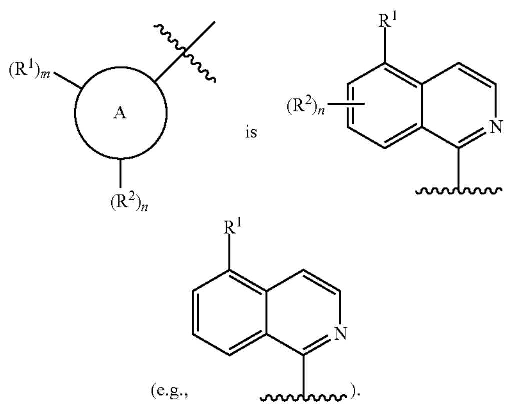
In certain embodiments,
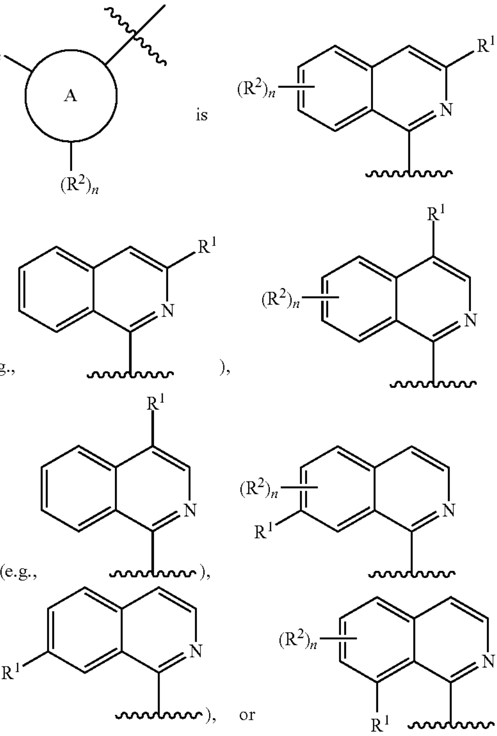

-continued

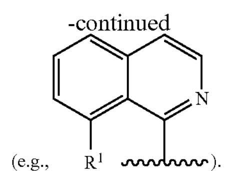

In certain embodiments, $R^1$ comprises an electrophilic moiety. In certain embodiments, $R^1$ comprises a Michael acceptor moiety. In certain embodiments, the electrophilic moiety or Michael acceptor moiety reacts with a cysteine residue of a kinase (e.g., CDK (e.g., CDK7)). In certain embodiments, the electrophilic moiety or Michael acceptor moiety may react with residue Cys312 of CDK7. In certain embodiments, the compound of the present disclosure is able to covalently or irreversibly attach to a kinase. In certain embodiments, the compound of the present disclosure is able to covalently or irreversibly attach to CDK7. In certain embodiments, the compound of the present disclosure is able to non-covalently or reversibly bind to a kinase. The non-covalent or reversible binding to the kinase may involve non-covalent interactions (e.g., electrostatic interactions, hydrophobic interactions, hydrogen bonding, van der Waals interactions, π-π stacking, or a combination thereof).

In certain embodiments, $R^1$ is of Formula (i-1):

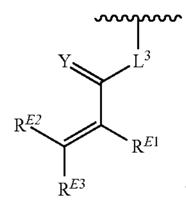

In certain embodiments, $R^1$ is of the formula:

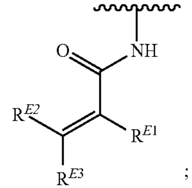

and m is 1. In certain embodiments, $R^1$ is of Formula (i-2):

(i-2)

In certain embodiments, $R^1$ is of Formula (i-3):

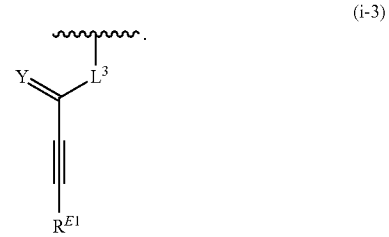

In certain embodiments, $R^1$ is of Formula (i-4):

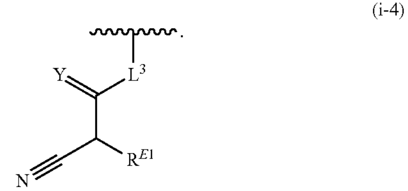

In certain embodiments, $R^1$ is of Formula (i-5):

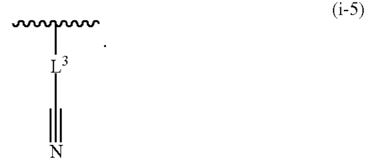

In certain embodiments, $R^1$ is of Formula (i-6):

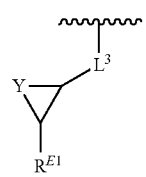

In certain embodiments, $R^1$ is of Formula (i-7):

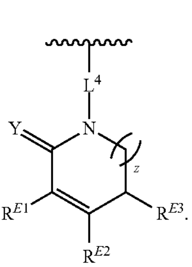

In certain embodiments, $R^1$ is of Formula (i-8):

(i-8)

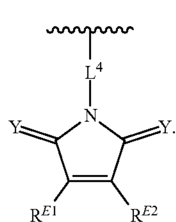

In certain embodiments, $R^1$ is of Formula (i-9):

(i-9)

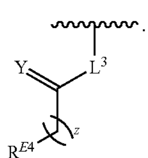

In certain embodiments, $R^1$ is of Formula (i-10):

(i-10)

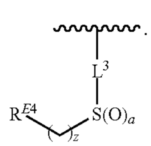

In certain embodiments, $R^1$ is of Formula (i-11):

(i-11)

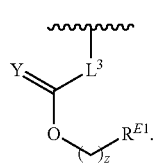

In certain embodiments, $R^1$ is of Formula (i-12):

(i-12)

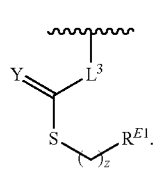

In certain embodiments, $R^1$ is of Formula (i-13):

(i-13)

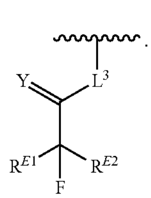

In certain embodiments, $R^1$ is of Formula (i-14):

(i-14)

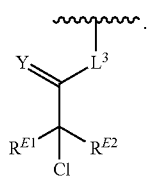

In certain embodiments, $R^1$ is of Formula (i-15):

(i-15)

In certain embodiments, $R^1$ is of Formula (i-16)

(i-16)

In certain embodiments, $R^1$ is of Formula (i-17):

(i-17)

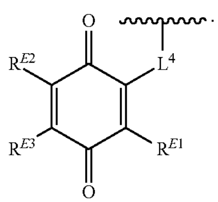

In certain embodiments, $R^1$ is of Formula (i-18):

(i-18)

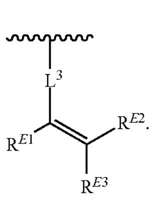

In certain embodiments, $R^1$ is of Formula (i-19):

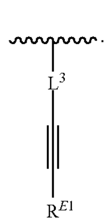

(i-19)

In certain embodiments, $R^1$ is of Formula (i-20):

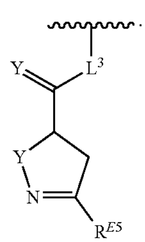

(i-20)

In certain embodiments, $R^1$ is of Formula (i-21):

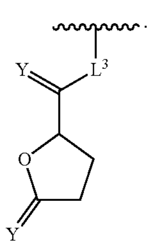

(i-21)

In certain embodiments, $R^1$ is of Formula (i-22):

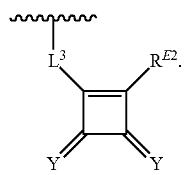

(i-22)

In certain embodiments, $R^1$ is of Formula (i-23):

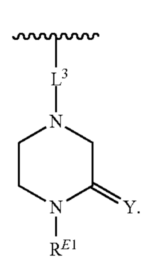

(i-23)

In certain embodiments, $R^1$ is of Formula (i-24):

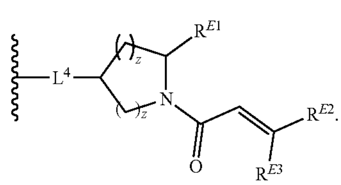

(i-24)

In certain embodiments, $R^1$ is of Formula (i-25):

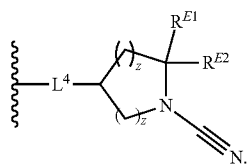

(i-25)

In certain embodiments, $R^1$ is of Formula (i-26):

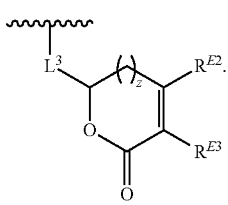

(i-26)

In certain embodiments, $R^1$ is of Formula (i-27):

(i-27)

In certain embodiments, $R^1$ is of Formula (i-28):

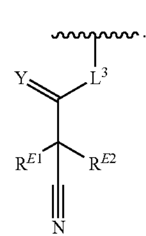

(i-28)

In certain embodiments, $R^1$ is of Formula (i-29):

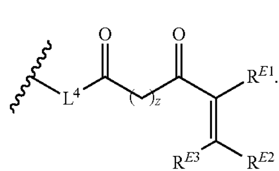

(i-29)

In certain embodiments, $R^1$ is of Formula (i-30):

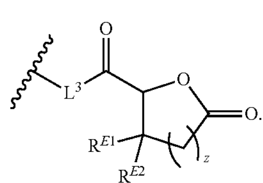

(i-30)

In certain embodiments, $R^1$ is of Formula (i-31):

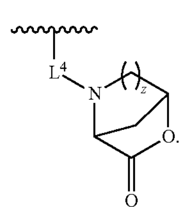

(i-31)

In certain embodiments, $R^1$ is of Formula (i-32):

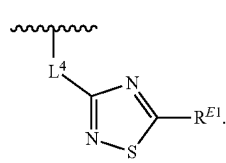

(i-32)

In certain embodiments, $R^1$ is of Formula (i-33):

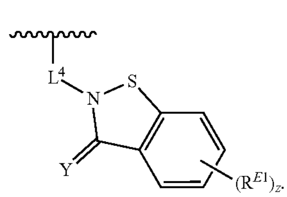

(i-33)

In certain embodiments, $R^1$ is of Formula (i-34):

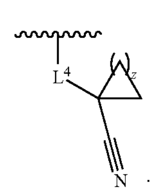

(i-34)

In certain embodiments, $R^1$ is of Formula (i-35):

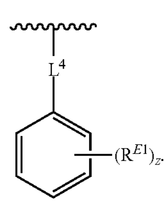

(i-35)

In certain embodiments, $R^1$ is of Formula (i-36):

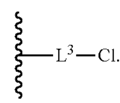

(i-36)

In certain embodiments, $R^1$ is of Formula (i-37):

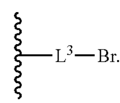

(i-37)

In certain embodiments, $R^1$ is of Formula (i-38):

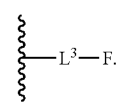

(i-38)

In certain embodiments, R is of Formula (i-39):

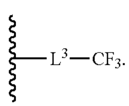

(i-39)

In certain embodiments, R is of Formula (i-40):

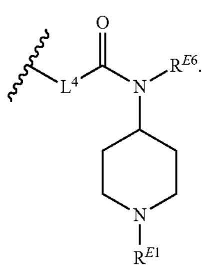

(i-40)

In certain embodiments, $R^1$ is of Formula (i-41):

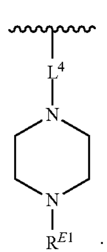

(i-41)

In certain embodiments, $R^1$ is of Formula (i-42):

(i-42)

In certain embodiments, $R^1$ is of Formula (i-1a):

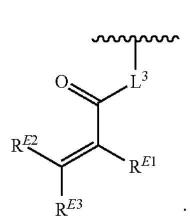

(i-1a)

In certain embodiments, $R^1$ is of Formula (i-1b):

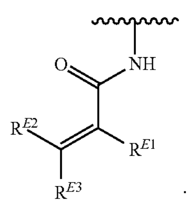

(i-1b)

In certain embodiments, $R^1$ is of Formula (i-1c):

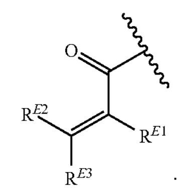

(i-1c)

In certain embodiments, $R^1$ is of Formula (i-1d):

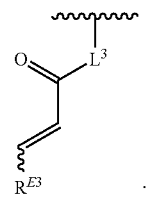

(i-1d)

In certain embodiments, $R^1$ is of Formula (i-1e):

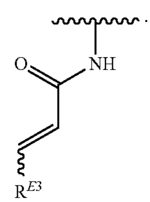

(i-1e)

In certain embodiments, $R^1$ is of Formula (i-1f):

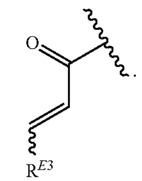

(i-1f)

In certain embodiments, $R^1$ is of Formula (i-1g):

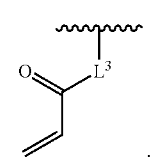

(i-1g)

In certain embodiments, $R^1$ is

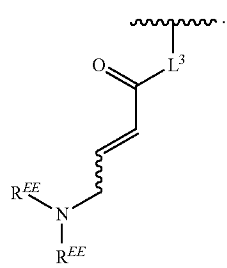

In certain embodiments, $R^1$ is
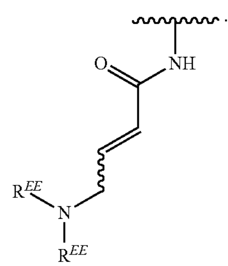
In certain embodiments, $R^1$ is
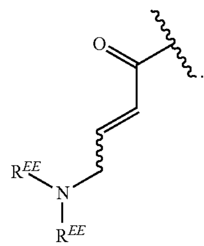
In certain embodiments, $R^1$ is of Formula (i-1g):
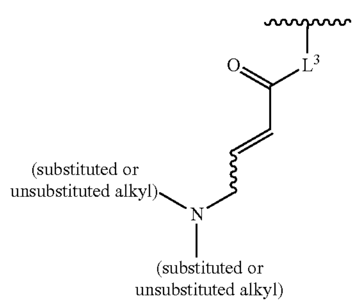
(i-1g)
(e.g., 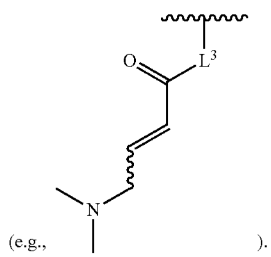
).
In certain embodiments, $R^1$ is
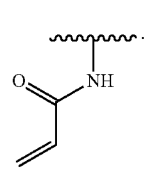 [SMILES: *NC(=O)C=C]
In certain embodiments, $R^1$ is
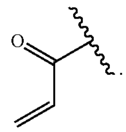
In certain embodiments, $R^1$ is
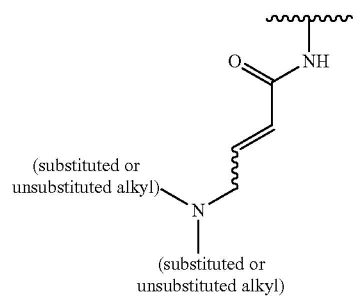
(e.g., 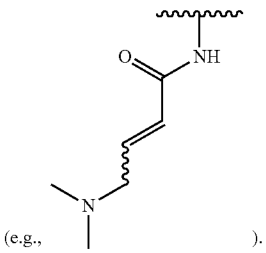
).
In certain embodiments, $R^1$ is
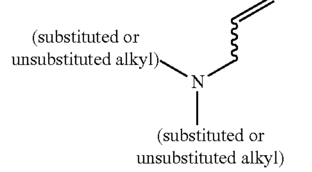
(e.g., 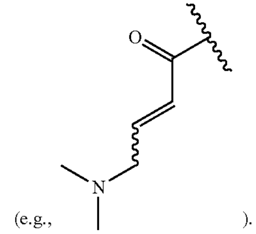
).

In certain embodiments, $R^1$ is of the formula:

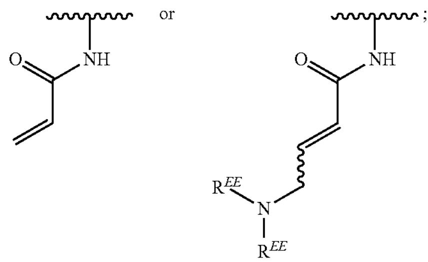

and m is 1. In certain embodiments, $R^1$ is of the formula:

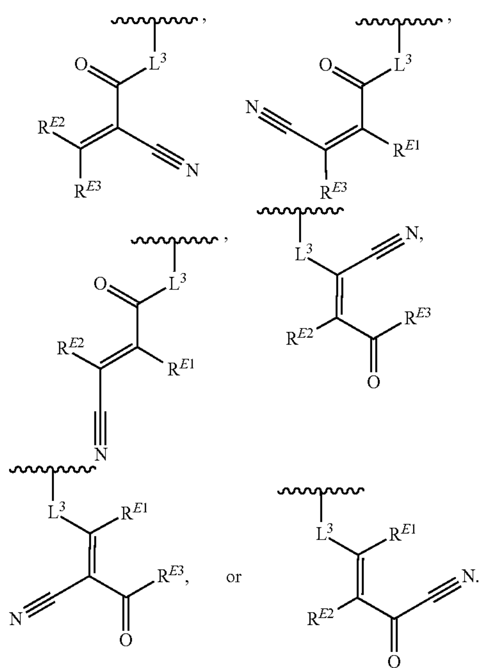

In certain embodiments, $R^1$ is of the formula:

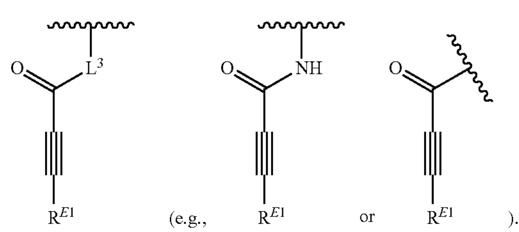

In certain embodiments, $R^1$ is of the formula:

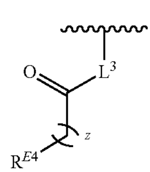

-continued

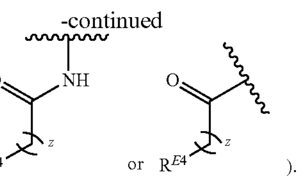

In certain embodiments, $R^1$ is of the formula:

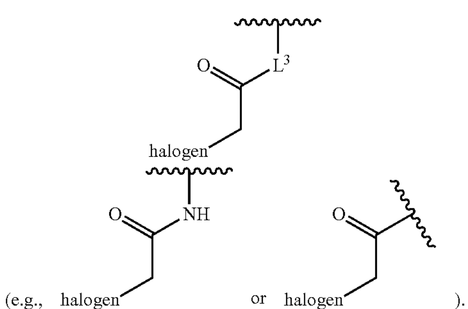

In certain embodiments, $R^1$ is not of any one of Formulae (i-35) to (i-42).

In certain embodiments, $L^3$ is a bond. $L^3$ is an optionally substituted $C_{1-4}$ hydrocarbon chain. In certain embodiments, $L^3$ is optionally substituted CM alkylene. In certain embodiments, $L^3$ is unsubstituted $C_{1-4}$alkylene (e.g., —$CH_2$—). In certain embodiments, $L^3$ is optionally substituted $C_{2-4}$ alkenylene (e.g., —CH═CH—). In certain embodiments, $L^3$ is optionally substituted $C_{2-4}$ alkynylene (e.g., —C≡C—). In certain embodiments, $L^3$ is an optionally substituted CM hydrocarbon chain, wherein one or more carbon units of the hydrocarbon chain are independently replaced with —C(═O)—, —O—, —S—, —$NR^{L3a}$—, —$NR^{L3a}$C(═O)—, —C(═O)$NR^{L3a}$—, —SC(═O)—, —C(═O)S—, —OC(═O)—, —C(═O)O—, —$NR^{L3a}$C(═S)—, —C(═S)$NR^{L3a}$—, trans-$CR^{L3b}$═$CR^{L3b}$—, cis-$CR^{L3b}$═$CR^{L3b}$—, —C≡C—, —S(═O)—, —S(═O)O—, —OS(═O)—, —S(═O)$NR^{L3a}$—, —$NR^{L3a}$S(═O)—, —S(═O)$_2$—, —S(═O)$_2$O—, —OS(═O)$_2$—, —S(═O)$_2$$NR^{L3a}$—, or —$NR^{L3a}$S(═O)$_2$—. In certain embodiments, $L^3$ is an optionally substituted $C_{1-4}$ hydrocarbon chain, wherein one carbon unit of the hydrocarbon chain is replaced with —$NR^{L3a}$— (e.g., —NH—). In certain embodiments, $L^3$ is of the formula: —$(CH_2)_{1-4}$—$NR^{L3a}$— (e.g., —$(CH_2)_{1-4}$—NH—) or —$NR^{L3a}$—$CH_2)_{1-4}$— (e.g., —NH—$CH_2)_{1-4}$—). In certain embodiments, $L^3$ is —$NR^{L3a}$—. In certain embodiments, $L^3$ is —$NR^{L3a}$(C═O)—. In certain embodiments, $L^3$ is —(C═O)$NR^{L3a}$—. In certain embodiments, $L^3$ is —NH—. In certain embodiments, $L^3$ is —(C═O)—. In certain embodiments, $L^3$ is —NH(C═O)—. In certain embodiments, $L^3$ is —(C═O)NH—. In certain embodiments, $L^3$ is —O—. In certain embodiments, $L^3$ is —S—.

In certain embodiments, $R^{L3a}$ is hydrogen. In certain embodiments, $R^{L3a}$ is substituted or unsubstituted acyl (e.g., —C(═O)$R^a$, —C(═O)O$R^a$, —C(═O)N$(R^a)_2$). In certain embodiments, $R^{L3a}$ is optionally substituted $C_{1-6}$ alkyl (e.g., Me). In certain embodiments, $R^{L3a}$ is a nitrogen protecting group (e.g., Bn, Boc, Cbz, Fmoc, trifluoroacetyl, triphenylmethyl, acetyl, Ts).

When Formula (I) includes two or more instances of a moiety, unless otherwise provided, any two instances of the moiety may be the same or different from each other.

In certain embodiments, at least one instance of $R^{L3b}$ is hydrogen. In certain embodiments, each instance of $R^{L3b}$ is hydrogen. In certain embodiments, at least one instance of $R^{L3b}$ is —Cl, —Br, or —I. In certain embodiments, each instance of $R^{L3b}$ is —Cl, —Br, or —I. In certain embodiments, at least one instance of $R^{L3b}$ is —F. In certain embodiments, each instance of $R^{L3b}$ is —F. In certain embodiments, at least one instance of $R^{L3b}$ is optionally substituted alkyl, optionally substituted alkenyl, or optionally substituted alkynyl. In certain embodiments, at least one instance of $R^{L3b}$ is optionally substituted carbocyclyl, optionally substituted heterocyclyl, optionally substituted aryl, or optionally substituted heteroaryl. In certain embodiments, two $R^{L3b}$ groups are joined to form an optionally substituted carbocyclic ring. In certain embodiments, two $R^{L3b}$ groups are joined to form an optionally substituted heterocyclic ring.

In certain embodiments, $L^4$ is a bond. In certain embodiments, $L^4$ is an optionally substituted $C_{1-6}$ hydrocarbon chain. In certain embodiments, $L^4$ is optionally substituted $C_{1-3}$ alkylene. In certain embodiments, $L^4$ is —$CH_2$—. In certain embodiments, $L^4$ is —$(CH_2)_2$—. In certain embodiments, $L^4$ is —$(CH_2)_3$—.

In certain embodiments, $R^m$ is hydrogen. In certain embodiments, $R^m$ is —Cl, —Br, or —I. In certain embodiments, $R^m$ is —F. In certain embodiments, $R^{E1}$ is optionally substituted alkyl (e.g., substituted or unsubstituted $C_{1-6}$ alkyl). In certain embodiments, $R^m$ is optionally substituted alkenyl or optionally substituted alkynyl. In certain embodiments, $R^m$ is optionally substituted carbocyclyl, optionally substituted heterocyclyl, optionally substituted aryl, or optionally substituted heteroaryl. In certain embodiments, $R^m$ is —CN, —$CH_2OR^{EE}$, —$CH_2N(R^{EE})_2$, —$CH_2SR^{EE}$, —$OR^{EE}$, —$N(R^{EE})_2$, —$Si(R^{EE})_3$, or —$SR^{EE}$ In certain embodiments, $R^{E1}$ is —$CH_2N(R^{EE})_2$. In certain embodiments, $R^{E1}$ is —$CH_2N$ (optionally substituted alkyl)$_2$ (e.g., —$CH_2N(CH_3)_2$). In certain embodiments, $R^{E1}$ is —CN. In certain embodiments, $R^{E1}$ is not —OH, —SH, —$NHR^{EE}$, or —$NH_2$.

In certain embodiments, $R^{E2}$ is hydrogen. In certain embodiments, $R^{E2}$ is —Cl, —Br, or —I. In certain embodiments, $R^{E2}$ is —F. In certain embodiments, $R^{E2}$ is optionally substituted alkyl (e.g., substituted or unsubstituted $C_{1-6}$ alkyl). In certain embodiments, $R^{E2}$ is optionally substituted alkenyl or optionally substituted alkynyl. In certain embodiments, $R^{E2}$ is optionally substituted carbocyclyl, optionally substituted heterocyclyl, optionally substituted aryl, or optionally substituted heteroaryl. In certain embodiments, $R^{E2}$ is —CN, —$CH_2OR^{EE}$, —$CH_2N(R^{EE})_2$, —$CH_2SR^{EE}$, —$OR^{EE}$, —$N(R^{EE})_2$, —$Si(R^{EE})_3$, or —$SR^{EE}$. In certain embodiments, $R^{E2}$ is —$CH_2N(R^{EE})_2$. In certain embodiments, $R^{E2}$ is —$CH_2N$ (optionally substituted alkyl)$_2$ (e.g., —$CH_2N(CH_3)_2$). In certain embodiments, $R^{E2}$ is —CN. In certain embodiments, $R^{E2}$ is not —OH, —SH, —$NHR^{EE}$, or —$NH_2$.

In certain embodiments, $R^{E3}$ is hydrogen. In certain embodiments, $R^{E3}$ is —Cl, —Br, or —I. In certain embodiments, $R^{E3}$ is —F. In certain embodiments, $R^{E3}$ is optionally substituted alkyl (e.g., substituted or unsubstituted $C_{1-6}$ alkyl). In certain embodiments, $R^{E3}$ is optionally substituted alkenyl or optionally substituted alkynyl. In certain embodiments, $R^{E3}$ is optionally substituted carbocyclyl, optionally substituted heterocyclyl, optionally substituted aryl, or optionally substituted heteroaryl. In certain embodiments, $R^{E3}$ is —CN, —$CH_2OR^{EE}$, —$CH_2N(R^{EE})_2$, —$CH_2SR^{EE}$, —$OR^{EE}$, —$N(R^{EE})_2$, —$Si(R^{EE})_3$, or —$SR^{EE}$. In certain embodiments, $R^{E3}$ is —$CH_2N(R^{EE})_2$. In certain embodiments, $R^{E3}$ is —$CH_2N$ (optionally substituted alkyl)$_2$ (e.g., —$CH_2N(CH_3)_2$). In certain embodiments, $R^{E3}$ is —CN. In certain embodiments, $R^{E3}$ is not —OH, —SH, —$NHR^{EE}$, or —$NH_2$.

In certain embodiments, $R^{E1}$ and $R^{E3}$ are joined to form an optionally substituted carbocyclic ring. In certain embodiments, $R^{E1}$ and $R^{E3}$ are joined to form an optionally substituted heterocyclic ring. In certain embodiments, $R^{E2}$ and $R^{E3}$ are joined to form an optionally substituted carbocyclic ring. In certain embodiments, $R^{E2}$ and $R^{E3}$ are joined to form an optionally substituted heterocyclic ring. In certain embodiments, $R^{E1}$ and $R^{E2}$ are joined to form an optionally substituted carbocyclic ring. In certain embodiments, $R^{E1}$ and $R^{E2}$ are joined to form an optionally substituted heterocyclic ring.

In certain embodiments, at least one instance of $R^{EE}$ is hydrogen. In certain embodiments, each instance of $R^{EE}$ is hydrogen. In certain embodiments, each instance of $R^{EE}$ is not hydrogen. In certain embodiments, at least one instance of $R^{EE}$ is optionally substituted alkyl (e.g., substituted or unsubstituted $C_{1-6}$ alkyl). In certain embodiments, at least one instance of $R^{EE}$ is unsubstituted $C_{1-3}$ alkyl (e.g., Me). In certain embodiments, each instance of $R^{EE}$ is optionally substituted alkyl. In certain embodiments, each instance of $R^{EE}$ is unsubstituted $C_{1-3}$ alkyl (e.g., Me). In certain embodiments, at least one instance of $R^{EE}$ is optionally substituted alkenyl or optionally substituted alkynyl. In certain embodiments, at least one instance of $R^{EE}$ is optionally substituted carbocyclyl, optionally substituted heterocyclyl, optionally substituted aryl, or optionally substituted heteroaryl. In certain embodiments, two instances of $R^{EE}$ are joined to form substituted or unsubstituted heterocyclyl (e.g., substituted or unsubstituted, 3- to 7-membered, monocyclic heterocyclyl). In certain embodiments, each instance of $R^{EE}$ is independently hydrogen or substituted or unsubstituted alkyl, or two instances of $R^{EE}$ are joined to form substituted or unsubstituted heterocyclyl; and m is 1.

In certain embodiments, $R^{14}$ is —Cl, —Br, or —I. In certain embodiments, $R^{14}$ is —F. In certain embodiments, $R^{14}$ is —$OS(=O)R^{E4a}$ or —$OS(=O)_2R^{E4a}$, wherein $R^{E4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^{14}$ is —$OR^{E4a}$. In certain embodiments, $R^{E4}$ is —OMs, —OTf, —OTs, —OBs, or 2-nitrobenzenesulfonyloxy. In certain embodiments, $R^{14}$ is —OMe, —$OCF_3$, or —OPh. In certain embodiments, $R^{14}$ is —$OC(=O)R^{E4a}$. In certain embodiments, $R^{14}$ is —OC(=O)Me, —OC(=O)$CF_3$, —OC(=O)Ph, or —OC(=O)Cl. In certain embodiments, $R^{E4}$ is —$OC(=O)OR^{E4a}$. In certain embodiments, $R^{14}$ is —OC(=O)OMe or —OC(=O)O(t-Bu).

In certain embodiments, $R^{E5}$ is —Cl, —Br, or —I. In certain embodiments, $R^{E5}$ is —F.

In certain embodiments, $R^{E6}$ is hydrogen. In certain embodiments, $R^{E6}$ is substituted or unsubstituted $C_1$-$C_6$ alkyl (e.g., Me). In certain embodiments, $R^{E6}$ is a nitrogen protecting group (e.g., Bn, Boc, Cbz, Fmoc, trifluoroacetyl, triphenylmethyl, acetyl, Ts).

In certain embodiments, a is 1. In certain embodiments, a is 2.

In certain embodiments, at least one instance of z is 0. In certain embodiments, at least one instance of z is 1. In certain embodiments, at least one instance of z is 2. In certain embodiments, at least one instance of z is 3, 4, 5, or 6.

In certain embodiments, at least one instance of Y is O. In certain embodiments, each instance of Y is O. In certain embodiments, at least one instance of Y is S. In certain embodiments, at least one instance of Y is $NR^{E7}$. In certain embodiments, at least one instance of Y is NH.

In certain embodiments, $R^{E7}$ is hydrogen. In certain embodiments, $R^{E7}$ is substituted or unsubstituted $C_1$-$C_6$ alkyl (e.g., Me). In certain embodiments, $R^{E7}$ is a nitrogen protecting group (e.g., Bn, Boc, Cbz, Fmoc, trifluoroacetyl, triphenylmethyl, acetyl, Ts).

In certain embodiments, m is 0. In certain embodiments, m is 1.

In certain embodiments, at least one instance of $R^2$ is halogen (e.g., F, Cl, Br, I). In certain embodiments, at least one instance of $R^2$ is substituted alkyl (e.g., alkyl substituted with one or more instances of halogen (e.g., F)). In certain embodiments, at least one instance of $R^2$ is unsubstituted alkyl. In certain embodiments, at least one instance of $R^2$ is unsubstituted, $C_{1-6}$ alkyl. In certain embodiments, at least one instance of $R^2$ is Me. In certain embodiments, at least one instance of $R^2$ is Et, Pr, or Bu. In certain embodiments, at least one instance of $R^2$ is substituted $C_{1-6}$ alkyl. In certain embodiments, at least one instance of $R^2$ is substituted methyl (e.g., —$CF_3$, —$CF_2H$, —$CFH_2$). In certain embodiments, at least one instance of $R^2$ is substituted ethyl, substituted propyl, or substituted butyl. In certain embodiments, at least one instance of $R^2$ is substituted or unsubstituted alkenyl. In certain embodiments, at least one instance of $R^2$ is substituted or unsubstituted, $C_{2-6}$ alkenyl (e.g., substituted or unsubstituted vinyl or substituted or unsubstituted allyl). In certain embodiments, at least one instance of $R^2$ is substituted or unsubstituted alkynyl. In certain embodiments, at least one instance of $R^2$ is substituted or unsubstituted, $C_{2-6}$ alkynyl (substituted or unsubstituted ethynyl). In certain embodiments, at least one instance of $R^2$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^2$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^2$ is substituted or unsubstituted heterocyclyl (e.g., substituted or unsubstituted, 3- to 7-membered, monocyclic heterocyclyl). In certain embodiments, at least one instance of $R^2$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^2$ is substituted or unsubstituted aryl. In certain embodiments, at least one instance of $R^2$ is substituted or unsubstituted phenyl. In certain embodiments, at least one instance of $R^2$ is substituted or unsubstituted naphthyl. In certain embodiments, at least one instance of $R^2$ is substituted or unsubstituted heteroaryl. In certain embodiments, at least one instance of $R^2$ is substituted or unsubstituted, 5- to 6-membered, monocyclic heteroaryl. In certain embodiments, at least one instance of $R^2$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^2$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^2$ is substituted or unsubstituted, 9- to 10-membered, bicyclic heteroaryl. In certain embodiments, at least one instance of $R^2$ is —$OR^a$ (e.g., —OH, —O (substituted or unsubstituted, $C_{1-6}$ alkyl) (e.g., —OMe, —$OCF_3$, —OEt, —OPr, —OBu, or —OBn), or —O (substituted or unsubstituted phenyl) (e.g., —OPh)). In certain embodiments, at least one instance of $R^2$ is —OMe. In certain embodiments, at least one instance of $R^2$ is —$SR^a$ (e.g., —SH, —S (substituted or unsubstituted, $C_{1-6}$ alkyl) (e.g., —SMe, —$SCF_3$, —SEt, —SPr, —SBu, or —SBn), or —S (substituted or unsubstituted phenyl) (e.g., —SPh)). In certain embodiments, at least one instance of $R^2$ is —$N(R^a)_2$ (e.g., —$NH_2$, —NH (substituted or unsubstituted, $C_{1-6}$ alkyl) (e.g., —NHMe), or —N (substituted or unsubstituted, $C_{1-6}$ alkyl)-(substituted or unsubstituted, $C_{1-6}$ alkyl) (e.g., —$NMe_2$)). In certain embodiments, at least one instance of $R^2$ is —CN or —SCN. In certain embodiments, at least one instance of $R^2$ is —$NO_2$. In certain embodiments, at least one instance of $R^2$ is —$C(=NR^a)R^a$, —$C(=NR^a)OR^a$, or —$C(=NR^a)N(R^a)_2$. In certain embodiments, at least one instance of $R^2$ is —$C(=O)R^a$ (e.g., —C(=O) (substituted or unsubstituted alkyl) (e.g., —C(=O)Me) or —C(=O) (substituted or unsubstituted phenyl)). In certain embodiments, at least one instance of $R^2$ is —$C(=O)OR^a$ (e.g., —C(=O)OH, —C(=O)O (substituted or unsubstituted alkyl) (e.g., —C(=O)OMe), or —C(=O)O (substituted or unsubstituted phenyl)). In certain embodiments, at least one instance of $R^2$ is —$C(=O)N(R^a)_2$ (e.g., —$C(=O)NH_2$, —C(=O)NH (substituted or unsubstituted alkyl) (e.g., —C(=O)NHMe), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, at least one instance of $R^2$ is —$NR^aC(=O)R^a$ (e.g., —NHC(=O) (substituted or unsubstituted, $C_{1-6}$ alkyl) (e.g., —NHC(=O)Me) or —NHC(=O) (substituted or unsubstituted phenyl)). In certain embodiments, at least one instance of $R^2$ is —$NR^aC(=O)OR^a$. In certain embodiments, at least one instance of $R^2$ is —$NR^aC(=O)N(R^a)_2$ (e.g., —$NHC(=O)NH_2$, —NHC(=O)NH (substituted or unsubstituted, $C_{1-6}$ alkyl) (e.g., —NHC(=O)NHMe)). In certain embodiments, at least one instance of $R^2$ is —$OC(=O)R^a$ (e.g., —OC(=O) (substituted or unsubstituted alkyl) or —OC(=O) (substituted or unsubstituted phenyl)), —$OC(=O)OR^a$(e.g., —OC(=O)O (substituted or unsubstituted alkyl) or —OC(=O)O (substituted or unsubstituted phenyl)), or —$OC(=O)N(R^a)_2$ (e.g., —$OC(=O)NH_2$, —OC(=O)NH (substituted or unsubstituted alkyl), —OC(=O)NH (substituted or unsubstituted phenyl), —OC(=O)N (substituted or unsubstituted alkyl)-(substituted or unsubstituted alkyl), or —OC(=O)N (substituted or unsubstituted phenyl)-(substituted or unsubstituted alkyl)).

In certain embodiments, n is 0. In certain embodiments, n is 1. In certain embodiments, n is 2. In certain embodiments, n is 3, 4, 5, or 6.

In certain embodiments, at least one instance of $R^2$ is halogen, substituted or unsubstituted alkyl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)$ $R^a$, —$NR^aC$(═O)$OR^a$, —$NR^aC$(═O)$N(R^a)_2$, —OC(═O)$R^a$, —OC(═O)$OR^a$, or —OC(═O)$N(R^a)_2$; and n is 1 or 2, as valency permits.

In certain embodiments, L is a single bond. In certain embodiments, L is —C(═O)—.

Formula (I) includes $R^3$ as a substituent on a nitrogen atom. In certain embodiments, $R^3$ is hydrogen. In certain embodiments, $R^3$ is substituted or unsubstituted acyl (e.g., —C(═O)$R^a$, —C(═O)$OR^a$, —C(═O)$N(R^a)_2$). In certain embodiments, $R^3$ is substituted or unsubstituted alkyl (e.g., substituted or unsubstituted, $C_{1-6}$ alkyl). In certain embodiments, $R^3$ is Me. In certain embodiments, $R^3$ is Et, Pr, Bu, substituted methyl, substituted ethyl, substituted propyl, or substituted butyl. In certain embodiments, $R^3$ is a nitrogen protecting group (e.g., Bn, BOC, Cbz, Fmoc, trifluoroacetyl, triphenylmethyl, acetyl, Ts).

Formula (I) includes Ring B

Ring B is a heteroaryl ring. Formula (I) also includes Ring C

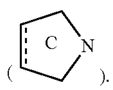

Ring B and Ring C are fused to each other to form the bicyclic ring

In certain embodiments,

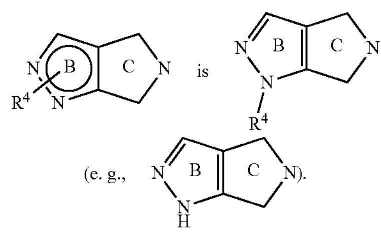

In certain embodiments.

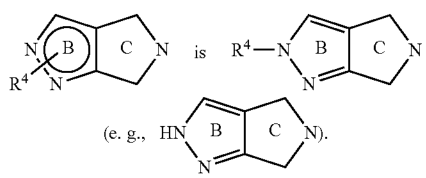

In certain embodiments, when $R^4$ is hydrogen,

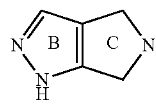

also includes the other tautomeric form

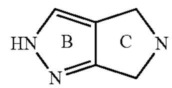

Formula (I) includes the substituent $R^4$ on a nitrogen atom of Ring B. In certain embodiments, $R^4$ is hydrogen. In certain embodiments, $R^4$ is substituted or unsubstituted acyl (e.g., —C(═O)$R^a$, —C(═O)$OR^a$, —C(═O)$N(R^a)_2$). In certain embodiments, $R^4$ is substituted or unsubstituted alkyl (e.g., substituted or unsubstituted, $C_{1-6}$ alkyl). In certain embodiments, $R^4$ is Me. In certain embodiments, $R^4$ is Et, Pr, Bu, substituted methyl, substituted ethyl, substituted propyl, or substituted butyl. In certain embodiments, $R^4$ is a nitrogen protecting group (e.g., Bn, BOC, Cbz, Fmoc, trifluoroacetyl, triphenylmethyl, acetyl, Ts).

Formula (I) includes the substituents $R^{5a}$ and $R^{5b}$ on a carbon atom of Ring C.

In certain embodiments, $R^{5a}$ is hydrogen. In certain embodiments, $R^{5a}$ is halogen (e.g., F, Cl, Br, I). In certain embodiments, $R^{5a}$ is substituted alkyl (e.g., alkyl substituted with one or more instances of halogen (e.g., F)). In certain embodiments, $R^{5a}$ is unsubstituted alkyl. In certain embodiments, $R^{5a}$ is unsubstituted, $C_{1-6}$ alkyl. In certain embodiments, $R^{5a}$ is Me. In certain embodiments, $R^{5a}$ is Et, Pr, or Bu. In certain embodiments, $R^{5a}$ is substituted $C_{1-6}$ alkyl. In certain embodiments, $R^{5a}$ is substituted methyl (e.g., —$CF_3$, —$CF_2H$, —$CFH_2$). In certain embodiments, $R^{5a}$ is substituted ethyl, substituted propyl, or substituted butyl. In certain embodiments, $R^{5a}$ is substituted or unsubstituted alkenyl. In certain embodiments, $R^{5a}$ is substituted or unsubstituted, $C_{2-6}$ alkenyl (e.g., substituted or unsubstituted vinyl or substituted or unsubstituted allyl). In certain embodiments, $R^{5a}$ is substituted or unsubstituted alkynyl. In certain embodiments, $R^{5a}$ is substituted or unsubstituted, $C_{2-6}$ alkynyl (substituted or unsubstituted ethynyl). In certain embodiments, $R^{5a}$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, $R^{5a}$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, $R^{5a}$ is substituted or unsubstituted heterocyclyl (e.g., substituted or unsubstituted, 3- to 7-membered, monocyclic heterocyclyl). In certain embodiments, $R^{5a}$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, $R^{5a}$ is substituted or unsubstituted aryl. In certain embodiments, $R^{5a}$ is substituted or unsubstituted phenyl. In certain embodiments, $R^{5a}$ is substituted or unsubstituted naphthyl. In certain embodiments, $R^{5a}$ is substituted or unsubstituted heteroaryl. In certain embodiments, $R^{5a}$ is substituted or unsubstituted, 5- to 6-membered, monocyclic heteroaryl. In certain embodiments, $R^{5a}$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, $R^{5a}$ is substituted or unsubstituted pyridinyl, substituted or unsubstituted pyrazinyl, substituted or unsubstituted pyrimidinyl, or substituted or unsubstituted pyridazinyl. In certain embodiments, $R^{5a}$ is substituted or unsubstituted, 9- to 10-membered, bicyclic heteroaryl. In certain embodiments, $R^{5a}$ is —OR$^a$ (e.g., —OH, —O (substituted or unsubstituted, $C_{1-6}$ alkyl) (e.g., —OMe, —$OCF_3$, —OEt, —OPr, —OBu, or —OBn), or —O (substituted or unsubstituted phenyl) (e.g., —OPh)). In certain embodiments, $R^{5a}$ is —OMe. In certain embodiments, $R^{5a}$ is —SR$^a$ (e.g., —SH, —S (substituted or unsubstituted, $C_{1-6}$ alkyl) (e.g., —SMe, —$SCF_3$, —SEt, —SPr, —SBu, or —SBn), or —S (substituted or unsubstituted phenyl) (e.g., —SPh)). In certain embodiments, $R^{5a}$ is —N(R$^a$)$_2$ (e.g., —$NH_2$, —NH (substituted or unsubstituted, $C_{1-6}$ alkyl) (e.g., —NHMe), or —N (substituted or unsubstituted, $C_{1-6}$ alkyl)-(substituted or unsubstituted, $C_{1-6}$ alkyl) (e.g., —$NMe_2$)). In certain embodiments, $R^{5a}$ is —CN or —SCN. In certain embodiments, $R^{5a}$ is —$NO_2$. In certain embodiments, $R^{5a}$ is —C(═NR$^a$)R$^a$, —C(═NR$^a$)OR$^a$, or —C(═NR$^a$)N(R$^a$)$_2$. In certain embodiments, $R^{5a}$ is —C(═O)R$^a$ (e.g., —C(═O) (substituted or unsubstituted alkyl) (e.g., —C(═O)Me) or —C(═O) (substituted or unsubstituted phenyl)). In certain embodiments, $R^{5a}$ is —C(═O)OR$^a$ (e.g., —C(═O)OH, —C(═O)O (substituted or unsubstituted alkyl) (e.g., —C(═O)OMe), or —C(═O)O (substituted or unsubstituted phenyl)). In certain embodiments, $R^{5a}$ is —C(═O)N(R$^a$)$_2$ (e.g., —C(═O)$NH_2$, —C(═O)NH (substituted or unsubstituted alkyl) (e.g., —C(═O)NHMe), —C(═O)NH (substituted or unsubstituted phenyl), —C(═O)N (substituted or unsubstituted alkyl)-(substituted or unsubstituted alkyl), or —C(═O)N (substituted or unsubstituted phenyl)-(substituted or unsubstituted alkyl)). In certain embodiments, $R^{5a}$ is —NR$^a$C(═O)R$^a$ (e.g., —NHC(═O) (substituted or unsubstituted, $C_{1-6}$ alkyl) (e.g., —NHC(═O)Me) or —NHC(═O) (substituted or unsubstituted phenyl)). In certain embodiments, $R^{5a}$ is —NR$^a$C(═O)OR$^a$. In certain embodiments, $R^{5a}$ is —NR$^a$C(═O)N(R$^a$)$_2$ (e.g., —NHC(═O)$NH_2$, —NHC(═O)NH (substituted or unsubstituted, $C_{1-6}$ alkyl) (e.g., —NHC(═O)NHMe)). In certain embodiments, $R^{5a}$ is —OC(═O)R$^a$ (e.g., —OC(═O) (substituted or unsubstituted alkyl) or —OC(═O) (substituted or unsubstituted phenyl)), —OC(═O)OR$^a$(e.g., —OC(═O)O (substituted or unsubstituted alkyl) or —OC(═O)O (substituted or unsubstituted phenyl)), or —OC(═O)N(R$^a$)$_2$ (e.g., —OC(═O)$NH_2$, —OC(═O)NH (substituted or unsubstituted alkyl), —OC(═O)NH (substituted or unsubstituted phenyl), —OC(═O)N (substituted or unsubstituted alkyl)-(substituted or unsubstituted alkyl), or —OC(═O)N (substituted or unsubstituted phenyl)-(substituted or unsubstituted alkyl)).

In certain embodiments, $R^{5b}$ is hydrogen. In certain embodiments, $R^{5b}$ is halogen (e.g., F, Cl, Br, I). In certain embodiments, $R^{5b}$ is substituted alkyl (e.g., alkyl substituted with one or more instances of halogen (e.g., F)). In certain embodiments, $R^{5b}$ is unsubstituted alkyl. In certain embodiments, $R^{5b}$ is unsubstituted, $C_{1-6}$ alkyl. In certain embodiments, $R^{5b}$ is Me. In certain embodiments, $R^{5b}$ is Et, Pr, or Bu. In certain embodiments, $R^{5b}$ is substituted $C_{1-6}$ alkyl. In certain embodiments, $R^{5b}$ is substituted methyl (e.g., —$CF_3$, —$CF_2H$, —$CFH_2$). In certain embodiments, $R^{5b}$ is substituted ethyl, substituted propyl, or substituted butyl. In certain embodiments, $R^{5b}$ is substituted or unsubstituted alkenyl. In certain embodiments, $R^{5b}$ is substituted or unsubstituted, $C_{2-6}$ alkenyl (e.g., substituted or unsubstituted vinyl or substituted or unsubstituted allyl). In certain embodiments, $R^{5b}$ is substituted or unsubstituted alkynyl. In certain embodiments, $R^{5b}$ is substituted or unsubstituted, $C_{2-6}$ alkynyl (substituted or unsubstituted ethynyl). In certain embodiments, $R^{5b}$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, $R^{5b}$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, $R^{5b}$ is substituted or unsubstituted heterocyclyl (e.g., substituted or unsubstituted, 3- to 7-membered, monocyclic heterocyclyl). In certain embodiments, $R^{5b}$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, $R^{5b}$ is substituted or unsubstituted aryl. In certain embodiments, $R^{5b}$ is substituted or unsubstituted phenyl. In certain embodiments, $R^{5b}$ is substituted or unsubstituted naphthyl. In certain embodiments, $R^{5b}$ is substituted or unsubstituted heteroaryl. In certain embodiments, $R^{5b}$ is substituted or unsubstituted, 5- to 6-membered, monocyclic heteroaryl. In certain embodiments, $R^{5b}$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, $R^{5b}$ is substituted or unsubstituted pyridinyl, substituted or unsubstituted pyrazinyl, substituted or unsubstituted pyrimidinyl, or substituted or unsubstituted pyridazinyl. In certain embodiments, $R^{5b}$ is substituted or unsubstituted, 9- to 10-membered, bicyclic heteroaryl. In certain embodiments, $R^{5b}$ is —OR$^a$ (e.g., —OH, —O (substituted or unsubstituted, $C_{1-6}$ alkyl) (e.g., —OMe, —$OCF_3$, —OEt, —OPr, —OBu, or —OBn), or —O (substituted or unsubstituted phenyl) (e.g., —OPh)). In certain embodiments, $R^{5b}$ is —OMe. In certain embodiments, $R^{5b}$ is —SR$^a$ (e.g., —SH, —S (substituted or unsubstituted, $C_{1-6}$ alkyl) (e.g., —SMe, —$SCF_3$, —SEt, —SPr, —SBu, or —SBn), or —S (substituted or unsubstituted phenyl) (e.g., —SPh)). In certain embodiments, $R^{5b}$ is —N(R$^a$)$_2$ (e.g., —$NH_2$, —NH (substituted or unsubstituted, $C_{1-6}$ alkyl) (e.g., —NHMe), or —N (substituted or unsubstituted, $C_{1-6}$ alkyl)-(substituted or unsubstituted, $C_{1-6}$ alkyl) (e.g., —$NMe_2$)). In certain embodiments, $R^{5b}$ is —CN or —SCN. In certain embodiments, $R^{5b}$ is —$NO_2$. In certain embodiments, $R^{5b}$ is —C(═NR$^a$)R$^a$, —C(═NR$^a$)OR$^a$, or —C(═NR$^a$)N(R$^a$)$_2$. In certain embodiments, $R^{5b}$ is —C(═O)R$^a$ (e.g., —C(═O) (substituted or unsubstituted alkyl) (e.g., —C(═O)Me) or —C(═O) (substituted or unsubstituted phenyl)). In certain embodiments, $R^{5b}$ is —C(═O)OR$^a$ (e.g., —C(═O)OH, —C(═O)O (substituted or unsubstituted alkyl) (e.g., —C(═O)OMe), or —C(═O)O (substituted or unsubstituted phenyl)). In certain embodiments, $R^{5b}$ is —C(═O)N(R$^a$)$_2$ (e.g., —C(═O)$NH_2$, —C(═O)NH (substituted or unsubstituted alkyl) (e.g., —C(═O)NHMe), —C(═O)NH (substituted or unsubstituted phenyl), —C(═O)N (substituted or unsubstituted alkyl)-(substituted or unsubstituted alkyl), or —C(═O)N (substituted or unsubstituted phenyl)-(substituted or unsubstituted alkyl)). In certain embodiments, $R^{5b}$ is $—NR^aC(═O)R^a$ (e.g., —NHC(═O) (substituted or unsubstituted, $C_{1-6}$ alkyl) (e.g., —NHC(═O)Me) or —NHC(═O) (substituted or unsubstituted phenyl)). In certain embodiments, $R^{5b}$ is $—NR^aC(═O)OR^a$. In certain embodiments, $R^{5b}$ is $—NR^aC(═O)N(R^a)_2$ (e.g., —NHC(═O)$NH_2$, —NHC(═O)NH (substituted or unsubstituted, $C_{1-6}$ alkyl) (e.g., —NHC(═O)NHMe)). In certain embodiments, $R^{5b}$ is $—OC(═O)R^a$ (e.g., —OC(═O) (substituted or unsubstituted alkyl) or —OC(═O) (substituted or unsubstituted phenyl)), $—OC(═O)OR^a$(e.g., —OC(═O)O (substituted or unsubstituted alkyl) or —OC(═O)O (substituted or unsubstituted phenyl)), or $—OC(═O)N(R^a)_2$ (e.g., —OC(═O)$NH_2$, —OC(═O)NH (substituted or unsubstituted alkyl), —OC(═O)NH (substituted or unsubstituted phenyl), —OC(═O)N (substituted or unsubstituted alkyl)-(substituted or unsubstituted alkyl), or —OC(═O)N (substituted or unsubstituted phenyl)-(substituted or unsubstituted alkyl)).

In certain embodiments, $R^{5a}$ and $R^{5b}$ are the same. In certain embodiments, each of $R^{5a}$ and $R^{5b}$ is hydrogen. In certain embodiments, each of $R^{5a}$ and $R^{5b}$ is substituted or unsubstituted alkyl. In certain embodiments, each of $R^{5a}$ and $R^{5b}$ is Me. In certain embodiments, $R^{5a}$ and $R^{5b}$ are different from each other. In certain embodiments, $R^{5a}$ is hydrogen, and $R^{5b}$ is substituted or unsubstituted alkyl (e.g., Me). In certain embodiments, $R^{5b}$ is hydrogen, and $R^{5a}$ is substituted or unsubstituted alkyl (e.g., Me).

In certain embodiments, $R^{5a}$ and $R^{5b}$ are joined to form substituted or unsubstituted carbocyclyl. In certain embodiments, $R^{5a}$ and $R^{5b}$ are joined to form an optionally substituted, monocyclic, $C_3$-$C_6$ carbocyclyl (e.g., cyclopropyl, cyclobutyl, cyclopentyl, cyclohexyl). In certain embodiments, $R^{5a}$ and $R^{5b}$ are joined to form substituted or unsubstituted heterocyclyl. In certain embodiments, $R^{5a}$ and $R^{5b}$ are joined to form an optionally substituted, monocyclic, 3- to 7-membered heterocyclyl (e.g., piperidinyl, piperizinyl, morpholinyl, pyrrolidinyl).

Formula (I) includes the substituents $R^6$ and $R^7$ on a carbon atom of Ring C. In certain embodiments, $R^6$ is hydrogen. In certain embodiments, $R^6$ is halogen (e.g., F, Cl, Br, I). In certain embodiments, $R^6$ is substituted or unsubstituted, $C_{1-3}$ alkyl. In certain embodiments, $R^6$ is substituted alkyl (e.g., alkyl substituted with one or more instances of halogen (e.g., F)). In certain embodiments, $R^6$ is unsubstituted alkyl. In certain embodiments, $R^6$ is unsubstituted, $C_{1-6}$ alkyl. In certain embodiments, $R^6$ is Me. In certain embodiments, $R^6$ is Et, Pr, or Bu. In certain embodiments, $R^6$ is substituted $C_{1-6}$ alkyl. In certain embodiments, $R^6$ is substituted methyl (e.g., $—CF_3$, $—CF_2H$, $—CFH_2$). In certain embodiments, $R^6$ is substituted ethyl, substituted propyl, or substituted butyl. In certain embodiments, $R^6$ is hydrogen, halogen, or substituted or unsubstituted alkyl. In certain embodiments, $R^6$ is substituted or unsubstituted alkenyl. In certain embodiments, $R^6$ is substituted or unsubstituted, $C_{2-6}$ alkenyl (e.g., substituted or unsubstituted vinyl or substituted or unsubstituted allyl). In certain embodiments, $R^6$ is substituted or unsubstituted alkynyl. In certain embodiments, $R^6$ is substituted or unsubstituted, $C_{2-6}$ alkynyl (substituted or unsubstituted ethynyl). In certain embodiments, $R^6$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, $R^6$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, $R^6$ is substituted or unsubstituted heterocyclyl (e.g., substituted or unsubstituted, 3- to 7-membered, monocyclic heterocyclyl). In certain embodiments, $R^6$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, $R^6$ is substituted or unsubstituted aryl. In certain embodiments, $R^6$ is substituted or unsubstituted phenyl. In certain embodiments, $R^6$ is substituted or unsubstituted naphthyl. In certain embodiments, $R^6$ is substituted or unsubstituted heteroaryl. In certain embodiments, $R^6$ is substituted or unsubstituted, 5- to 6-membered, monocyclic heteroaryl. In certain embodiments, $R^6$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, $R^6$ is substituted or unsubstituted pyridinyl, substituted or unsubstituted pyrazinyl, substituted or unsubstituted pyrimidinyl, or substituted or unsubstituted pyridazinyl. In certain embodiments, $R^6$ is substituted or unsubstituted, 9- to 10-membered, bicyclic heteroaryl. In certain embodiments, $R^6$ is $—OR^a$ (e.g., —OH, —O (substituted or unsubstituted, $C_{1-6}$ alkyl) (e.g., —OMe, $—OCF_3$, —OEt, —OPr, —OBu, or —OBn), or —O (substituted or unsubstituted phenyl) (e.g., —OPh)). In certain embodiments, $R^6$ is —OMe. In certain embodiments, $R^6$ is $—SR^a$ (e.g., —SH, —S (substituted or unsubstituted, $C_{1-6}$ alkyl) (e.g., —SMe, $—SCF_3$, —SEt, —SPr, —SBu, or —SBn), or —S (substituted or unsubstituted phenyl) (e.g., —SPh)). In certain embodiments, $R^6$ is $—N(R^a)_2$ (e.g., $—NH_2$, —NH (substituted or unsubstituted, $C_{1-6}$ alkyl) (e.g., —NHMe), or —N (substituted or unsubstituted, $C_{1-6}$ alkyl)-(substituted or unsubstituted, $C_{1-6}$ alkyl) (e.g., $—NMe_2$)). In certain embodiments, $R^6$ is —CN or —SCN. In certain embodiments, $R^6$ is $—NO_2$. In certain embodiments, $R^6$ is $—C(═NR^a)R^a$, $—C(═NR^a)OR^a$, or $—C(═NR^a)N(R^a)_2$. In certain embodiments, $R^6$ is $—C(═O)R^a$ (e.g., —C(═O) (substituted or unsubstituted alkyl) (e.g., —C(═O)Me) or —C(═O) (substituted or unsubstituted phenyl)). In certain embodiments, $R^6$ is $—C(═O)OR^a$ (e.g., —C(═O)OH, —C(═O)O (substituted or unsubstituted alkyl) (e.g., —C(═O)OMe), or —C(═O)O (substituted or unsubstituted phenyl)). In certain embodiments, $R^6$ is $—C(═O)N(R^a)_2$ (e.g., —C(═O)$NH_2$, —C(═O)NH (substituted or unsubstituted alkyl) (e.g., —C(═O)NHMe), —C(═O)NH (substituted or unsubstituted phenyl), —C(═O)N (substituted or unsubstituted alkyl)-(substituted or unsubstituted alkyl), or —C(═O)N (substituted or unsubstituted phenyl)-(substituted or unsubstituted alkyl)). In certain embodiments, $R^6$ is $—NR^aC(═O)R^a$ (e.g., —NHC(═O) (substituted or unsubstituted, $C_{1-6}$ alkyl) (e.g., —NHC(═O)Me) or —NHC(═O) (substituted or unsubstituted phenyl)). In certain embodiments, $R^6$ is $—NR^aC(═O)OR^a$. In certain embodiments, $R^6$ is $—NR^aC(═O)N(R^a)_2$ (e.g., —NHC(═O)$NH_2$, —NHC(═O)NH (substituted or unsubstituted, $C_{1-6}$ alkyl) (e.g., —NHC(═O)NHMe)). In certain embodiments, $R^6$ is $—OC(═O)R^a$ (e.g., —OC(═O) (substituted or unsubstituted alkyl) or —OC (=O) (substituted or unsubstituted phenyl)), —OC(=O)OR$^a$(e.g., —OC(=O)O (substituted or unsubstituted alkyl) or —OC(=O)O (substituted or unsubstituted phenyl)), or —OC(=O)N(R$^a$)$_2$ (e.g., —OC(=O)NH$_2$, —OC(=O)NH (substituted or unsubstituted alkyl), —OC(=O)NH (substituted or unsubstituted phenyl), —OC(=O)N (substituted or unsubstituted alkyl)-(substituted or unsubstituted alkyl), or —OC(=O)N (substituted or unsubstituted phenyl)-(substituted or unsubstituted alkyl)).

In certain embodiments, R$^7$ is hydrogen. In certain embodiments, R$^7$ is halogen (e.g., F, Cl, Br, I). In certain embodiments, R$^7$ is substituted or unsubstituted, C$_{1-3}$ alkyl. In certain embodiments, R$^7$ is substituted alkyl (e.g., alkyl substituted with one or more instances of halogen (e.g., F)). In certain embodiments, R$^7$ is unsubstituted alkyl. In certain embodiments, R$^7$ is unsubstituted, C$_{1-6}$ alkyl. In certain embodiments, R$^7$ is Me. In certain embodiments, R$^7$ is Et, Pr, or Bu. In certain embodiments, R$^7$ is substituted C$_{1-6}$ alkyl. In certain embodiments, R$^7$ is substituted methyl (e.g., —CF$_3$, —CF$_2$H, —CFH$_2$). In certain embodiments, R$^7$ is substituted ethyl, substituted propyl, or substituted butyl. In certain embodiments, R$^7$ is hydrogen, halogen, or substituted or unsubstituted alkyl. In certain embodiments, R$^7$ is substituted or unsubstituted alkenyl. In certain embodiments, R$^7$ is substituted or unsubstituted, C$_{2-6}$ alkenyl (e.g., substituted or unsubstituted vinyl or substituted or unsubstituted allyl). In certain embodiments, R$^7$ is substituted or unsubstituted alkynyl. In certain embodiments, R$^7$ is substituted or unsubstituted, C$_{2-6}$ alkynyl (substituted or unsubstituted ethynyl). In certain embodiments, R$^7$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, R$^7$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, R$^7$ is substituted or unsubstituted heterocyclyl (e.g., substituted or unsubstituted, 3- to 7-membered, monocyclic heterocyclyl). In certain embodiments, R$^7$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, R$^7$ is substituted or unsubstituted aryl. In certain embodiments, R$^7$ is substituted or unsubstituted phenyl. In certain embodiments, R$^7$ is substituted or unsubstituted naphthyl. In certain embodiments, R$^7$ is substituted or unsubstituted heteroaryl. In certain embodiments, R$^7$ is substituted or unsubstituted, 5- to 6-membered, monocyclic heteroaryl. In certain embodiments, R$^7$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, R$^7$ is substituted or unsubstituted pyridinyl, substituted or unsubstituted pyrazinyl, substituted or unsubstituted pyrimidinyl, or substituted or unsubstituted pyridazinyl. In certain embodiments, R$^7$ is substituted or unsubstituted, 9- to 10-membered, bicyclic heteroaryl. In certain embodiments, R$^7$ is —OR$^a$ (e.g., —OH, —O (substituted or unsubstituted, C$_{1-6}$ alkyl) (e.g., —OMe, —OCF$_3$, —OEt, —OPr, —OBu, or —OBn), or —O (substituted or unsubstituted phenyl) (e.g., —OPh)). In certain embodiments, R$^7$ is —OMe. In certain embodiments, R$^7$ is —SR$^a$ (e.g., —SH, —S (substituted or unsubstituted, C$_{1-6}$ alkyl) (e.g., —SMe, —SCF$_3$, —SEt, —SPr, —SBu, or —SBn), or —S (substituted or unsubstituted phenyl) (e.g., —SPh)). In certain embodiments, R$^7$ is —N(R$^a$)$_2$ (e.g., —NH$_2$, —NH (substituted or unsubstituted, C$_{1-6}$ alkyl) (e.g., —NHMe), or —N (substituted or unsubstituted, C$_{1-6}$ alkyl)-(substituted or unsubstituted, C$_{1-6}$ alkyl) (e.g., —NMe$_2$)). In certain embodiments, R$^7$ is —CN or —SCN. In certain embodiments, R$^7$ is —NO$_2$. In certain embodiments, R$^7$ is —C(=NR$^a$)R$^a$, —C(=NR$^a$)OR$^a$, or —C(=NR$^a$)N(R$^a$)$_2$. In certain embodiments, R$^7$ is —C(=O)R$^a$ (e.g., —C(=O) (substituted or unsubstituted alkyl) (e.g., —C(=O)Me) or —C(=O) (substituted or unsubstituted phenyl)). In certain embodiments, R$^7$ is —C(=O)OR$^a$(e.g., —C(=O)OH, —C(=O)O (substituted or unsubstituted alkyl) (e.g., —C(=O)OMe), or —C(=O)O (substituted or unsubstituted phenyl)). In certain embodiments, R$^7$ is —C(=O)N(R$^a$)$_2$ (e.g., —C(=O)NH$_2$, —C(=O)NH (substituted or unsubstituted alkyl) (e.g., —C(=O)NHMe), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, R$^7$ is —NR$^a$C(=O)R$^a$ (e.g., —NHC(=O) (substituted or unsubstituted, C$_{1-6}$ alkyl) (e.g., —NHC(=O)Me) or —NHC(=O) (substituted or unsubstituted phenyl)). In certain embodiments, R$^7$ is —NR$^a$C(=O)OR$^a$. In certain embodiments, R$^7$ is —NR$^a$C(=O)N(R$^a$)$_2$ (e.g., —NHC(=O)NH$_2$, —NHC(=O)NH (substituted or unsubstituted, C$_{1-6}$ alkyl) (e.g., —NHC(=O)NHMe)). In certain embodiments, R$^7$ is —OC(=O)R$^a$ (e.g., —OC(=O) (substituted or unsubstituted alkyl) or —OC(=O) (substituted or unsubstituted phenyl)), —OC(=O)OR$^a$(e.g., —OC(=O)O (substituted or unsubstituted alkyl) or —OC(=O)O (substituted or unsubstituted phenyl)), or —OC(=O)N(R$^a$)$_2$ (e.g., —OC(=O)NH$_2$, —OC(=O)NH (substituted or unsubstituted alkyl), —OC(=O)NH (substituted or unsubstituted phenyl), —OC(=O)N (substituted or unsubstituted alkyl)-(substituted or unsubstituted alkyl), or —OC(=O)N (substituted or unsubstituted phenyl)-(substituted or unsubstituted alkyl)).

In certain embodiments, R$^6$ and R$^7$ are the same. In certain embodiments, each of R$^6$ and R$^7$ is hydrogen. In certain embodiments, each of R$^6$ and R$^7$ is substituted or unsubstituted alkyl. In certain embodiments, each of R$^6$ and R$^7$ is Me. In certain embodiments, R$^6$ and R$^7$ are different from each other. In certain embodiments, R$^6$ is hydrogen, and R$^7$ is substituted or unsubstituted alkyl (e.g., Me). In certain embodiments, R$^7$ is hydrogen, and R$^6$ is substituted or unsubstituted alkyl (e.g., Me).

In certain embodiments, R$^6$ and R$^7$ are joined to form substituted or unsubstituted carbocyclyl. In certain embodiments, R$^6$ and R$^7$ are joined to form an optionally substituted, monocyclic, C$_3$-C$_6$ carbocyclyl (e.g., cyclopropyl, cyclobutyl, cyclopentyl, cyclohexyl). In certain embodiments, R$^6$ and R$^7$ are not joined to form unsubstituted cyclopropyl. In certain embodiments, R$^6$ and R$^7$ are not joined to form substituted or unsubstituted cyclopropyl. In certain embodiments, R$^6$ and R$^7$ are not joined to form substituted or unsubstituted carbocyclyl. In certain embodiments, R$^6$ and R$^7$ are joined to form substituted or unsubstituted heterocyclyl. In certain embodiments, R$^6$ and R$^7$ are joined to form an optionally substituted, monocyclic, 3- to 7-membered heterocyclyl (e.g., piperidinyl, piperizinyl, morpholinyl, pyrrolidinyl).

Formula (I) includes $R^8$ on a nitrogen atom. In certain embodiments, $R^8$ is hydrogen. In certain embodiments, $R^8$ is substituted or unsubstituted acyl (e.g., —C(═O)$R^a$, —C(═O)O$R^a$, —C(═O)N$(R^a)_2$). In certain embodiments, $R^8$ is substituted or unsubstituted alkyl (e.g., substituted or unsubstituted, $C_{1-6}$ alkyl). In certain embodiments, $R^8$ is Me. In certain embodiments, $R^8$ is Et, Pr, Bu, substituted methyl, substituted ethyl, substituted propyl, or substituted butyl. In certain embodiments, $R^8$ is a nitrogen protecting group (e.g., Bn, BOC, Cbz, Fmoc, trifluoroacetyl, triphenylmethyl, acetyl, Ts).

In certain embodiments, at least one instance of $R^9$ is hydrogen. In certain embodiments, each instance of $R^9$ is hydrogen. In certain embodiments, at least one instance of $R^9$ is halogen (e.g., F, Cl, Br, I). In certain embodiments, at least one instance of $R^9$ is substituted or unsubstituted, $C_{1-3}$ alkyl. In certain embodiments, at least one instance of $R^9$ is substituted alkyl (e.g., alkyl substituted with one or more instances of halogen (e.g., F)). In certain embodiments, at least one instance of $R^9$ is alkyl substituted at least with —N$(R^a)_2$. In certain embodiments, at least one instance of $R^9$ is —$(CH_2)_{1-3}$—N (substituted or unsubstituted alkyl)$_2$ (e.g., —$CH_2$—N (substituted or unsubstituted alkyl)$_2$). In certain embodiments, at least one instance of $R^9$ is —$CH_2$—N$(CH_3)_2$. In certain embodiments, at least one instance of $R^9$ is unsubstituted alkyl. In certain embodiments, at least one instance of $R^9$ is unsubstituted, $C_{1-6}$ alkyl. In certain embodiments, at least one instance of $R^9$ is Me. In certain embodiments, at least one instance of $R^9$ is Et, Pr, or Bu. In certain embodiments, at least one instance of $R^9$ is substituted $C_{1-6}$ alkyl. In certain embodiments, at least one instance of $R^9$ is substituted methyl (e.g., —$CF_3$, —$CF_2H$, —$CFH_2$). In certain embodiments, at least one instance of $R^9$ is substituted ethyl, substituted propyl, or substituted butyl. In certain embodiments, at least one instance of $R^9$ is hydrogen, halogen, or substituted or unsubstituted alkyl. In certain embodiments, at least one instance of $R^9$ is substituted or unsubstituted alkenyl. In certain embodiments, at least one instance of $R^9$ is substituted or unsubstituted, $C_{2-6}$ alkenyl (e.g., substituted or unsubstituted vinyl or substituted or unsubstituted allyl). In certain embodiments, at least one instance of $R^9$ is substituted or unsubstituted alkynyl. In certain embodiments, at least one instance of $R^9$ is substituted or unsubstituted, $C_{2-6}$ alkynyl (substituted or unsubstituted ethynyl). In certain embodiments, at least one instance of $R^9$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^9$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^9$ is substituted or unsubstituted heterocyclyl (e.g., substituted or unsubstituted, 3- to 7-membered, monocyclic heterocyclyl). In certain embodiments, at least one instance of $R^9$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^9$ is substituted or unsubstituted aryl. In certain embodiments, at least one instance of $R^9$ is substituted or unsubstituted phenyl. In certain embodiments, at least one instance of $R^9$ is substituted or unsubstituted naphthyl. In certain embodiments, at least one instance of $R^9$ is substituted or unsubstituted heteroaryl. In certain embodiments, at least one instance of $R^9$ is substituted or unsubstituted, 5- to 6-membered, monocyclic heteroaryl. In certain embodiments, at least one instance of $R^9$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^9$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^9$ is substituted or unsubstituted, 9- to 10-membered, bicyclic heteroaryl. In certain embodiments, at least one instance of $R^9$ is —O$R^a$ (e.g., —OH, —O (substituted or unsubstituted, $C_{1-6}$ alkyl) (e.g., —OMe, —O$CF_3$, —OEt, —OPr, —OBu, or —OBn), or —O (substituted or unsubstituted phenyl) (e.g., —OPh)). In certain embodiments, at least one instance of $R^9$ is —OMe. In certain embodiments, at least one instance of $R^9$ is —S$R^a$ (e.g., —SH, —S (substituted or unsubstituted, $C_{1-6}$ alkyl) (e.g., —SMe, —S$CF_3$, —SEt, —SPr, —SBu, or —SBn), or —S (substituted or unsubstituted phenyl) (e.g., —SPh)). In certain embodiments, at least one instance of $R^9$ is —N$(R^a)_2$ (e.g., —$NH_2$, —NH (substituted or unsubstituted, $C_{1-6}$ alkyl) (e.g., —NHMe), or —N (substituted or unsubstituted, $C_{1-6}$ alkyl)-(substituted or unsubstituted, $C_{1-6}$ alkyl) (e.g., —$NMe_2$)). In certain embodiments, at least one instance of $R^9$ is —CN or —SCN. In certain embodiments, at least one instance of $R^9$ is —$NO_2$. In certain embodiments, at least one instance of $R^9$ is —C(═N$R^a$)$R^a$, —C(═N$R^a$)O$R^a$, or —C(═N$R^a$)N$(R^a)_2$. In certain embodiments, at least one instance of $R^9$ is —C(═O)$R^a$ (e.g., —C(═O) (substituted or unsubstituted alkyl) (e.g., —C(═O)Me) or —C(═O) (substituted or unsubstituted phenyl)). In certain embodiments, at least one instance of $R^9$ is —C(═O)O$R^a$(e.g., —C(═O)OH, —C(═O)O (substituted or unsubstituted alkyl) (e.g., —C(═O)OMe), or —C(═O)O (substituted or unsubstituted phenyl)). In certain embodiments, at least one instance of $R^9$ is —C(═O)N$(R^a)_2$ (e.g., —C(═O)$NH_2$, —C(═O)NH (substituted or unsubstituted alkyl) (e.g., —C(═O)NHMe), —C(═O)NH (substituted or unsubstituted phenyl), —C(═O)N (substituted or unsubstituted alkyl)-(substituted or unsubstituted alkyl), or —C(═O)N (substituted or unsubstituted phenyl)-(substituted or unsubstituted alkyl)). In certain embodiments, at least one instance of $R^9$ is —N$R^a$C(═O)$R^a$ (e.g., —NHC(═O) (substituted or unsubstituted, $C_{1-6}$ alkyl) (e.g., —NHC(═O)Me) or —NHC(═O) (substituted or unsubstituted phenyl)). In certain embodiments, at least one instance of $R^9$ is —N$R^a$C(═O)O$R^a$. In certain embodiments, at least one instance of $R^9$ is —N$R^a$C(═O)N$(R^a)_2$ (e.g., —NHC(═O)$NH_2$, —NHC(═O)NH (substituted or unsubstituted, $C_{1-6}$ alkyl) (e.g., —NHC(═O)NHMe)). In certain embodiments, at least one instance of $R^9$ is —OC(═O)$R^a$ (e.g., —OC(═O) (substituted or unsubstituted alkyl) or —OC(═O) (substituted or unsubstituted phenyl)), —OC(═O)O$R^a$(e.g., —OC(═O)O (substituted or unsubstituted alkyl) or —OC(═O)O (substituted or unsubstituted phenyl)), or —OC(═O)N$(R^a)_2$ (e.g., —OC(═O)$NH_2$, —OC(═O)NH (substituted or unsubstituted alkyl), —OC(═O)NH (substituted or unsubstituted phenyl), —OC(═O)N (substituted or unsubstituted alkyl)-(substituted or unsubstituted alkyl), or —OC(═O)N (substituted or unsubstituted phenyl)-(substituted or unsubstituted alkyl)).

In certain embodiments, at least one instance of $R^{10}$ is hydrogen. In certain embodiments, each instance of $R^{10}$ is hydrogen. In certain embodiments, at least one instance of $R^{10}$ is halogen (e.g., F, Cl, Br, I). In certain embodiments, at least one instance of $R^{10}$ is substituted or unsubstituted, $C_{1-3}$ alkyl. In certain embodiments, at least one instance of $R^{10}$ is substituted alkyl (e.g., alkyl substituted with one or more instances of halogen (e.g., F)). In certain embodiments, at least one instance of $R^{10}$ is alkyl substituted at least with —$N(R^a)_2$. In certain embodiments, at least one instance of $R^{10}$ is —$(CH_2)_{1-3}$—N (substituted or unsubstituted alkyl)$_2$ (e.g., —$CH_2$—N (substituted or unsubstituted alkyl)$_2$). In certain embodiments, at least one instance of $R^{10}$ is —$CH_2$—$N(CH_3)_2$. In certain embodiments, at least one instance of $R^{10}$ is unsubstituted alkyl. In certain embodiments, at least one instance of $R^{10}$ is unsubstituted, $C_{1-6}$ alkyl. In certain embodiments, at least one instance of $R^{10}$ is Me. In certain embodiments, at least one instance of $R^{10}$ is Et, Pr, or Bu. In certain embodiments, at least one instance of $R^{10}$ is substituted $C_{1-6}$ alkyl. In certain embodiments, at least one instance of $R^{10}$ is substituted methyl (e.g., —$CF_3$, —$CF_2H$, —$CFH_2$). In certain embodiments, at least one instance of $R^{10}$ is substituted ethyl, substituted propyl, or substituted butyl. In certain embodiments, at least one instance of $R^{10}$ is hydrogen, halogen, or substituted or unsubstituted alkyl. In certain embodiments, at least one instance of $R^{10}$ is substituted or unsubstituted alkenyl. In certain embodiments, at least one instance of $R^{10}$ is substituted or unsubstituted, $C_{2-6}$ alkenyl (e.g., substituted or unsubstituted vinyl or substituted or unsubstituted allyl). In certain embodiments, at least one instance of $R^{10}$ is substituted or unsubstituted alkynyl. In certain embodiments, at least one instance of $R^{10}$ is substituted or unsubstituted, $C_{2-6}$ alkynyl (substituted or unsubstituted ethynyl). In certain embodiments, at least one instance of $R^{10}$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^{10}$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^{10}$ is substituted or unsubstituted heterocyclyl (e.g., substituted or unsubstituted, 3- to 7-membered, monocyclic heterocyclyl). In certain embodiments, at least one instance of $R^{10}$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^{10}$ is substituted or unsubstituted aryl. In certain embodiments, at least one instance of $R^{10}$ is substituted or unsubstituted phenyl. In certain embodiments, at least one instance of $R^{10}$ is substituted or unsubstituted naphthyl. In certain embodiments, at least one instance of $R^{10}$ is substituted or unsubstituted heteroaryl. In certain embodiments, at least one instance of $R^{10}$ is substituted or unsubstituted, 5- to 6-membered, monocyclic heteroaryl. In certain embodiments, at least one instance of $R^{10}$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^{10}$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^{10}$ is substituted or unsubstituted, 9- to 10-membered, bicyclic heteroaryl. In certain embodiments, at least one instance of $R^{10}$ is —$OR^a$ (e.g., —OH, —O (substituted or unsubstituted, $C_{1-6}$ alkyl) (e.g., —OMe, —$OCF_3$, —OEt, —OPr, —OBu, or —OBn), or —O (substituted or unsubstituted phenyl) (e.g., —OPh)). In certain embodiments, at least one instance of $R^{10}$ is —OMe. In certain embodiments, at least one instance of $R^{10}$ is —$SR^a$ (e.g., —SH, —S (substituted or unsubstituted, $C_{1-6}$ alkyl) (e.g., —SMe, —$SCF_3$, —SEt, —SPr, —SBu, or —SBn), or —S (substituted or unsubstituted phenyl) (e.g., —SPh)). In certain embodiments, at least one instance of $R^{10}$ is —$N(R^a)_2$ (e.g., —$NH_2$, —NH (substituted or unsubstituted, $C_{1-6}$ alkyl) (e.g., —NHMe), or —N (substituted or unsubstituted, $C_{1-6}$ alkyl)-(substituted or unsubstituted, $C_{1-6}$ alkyl) (e.g., —$NMe_2$)). In certain embodiments, at least one instance of $R^{10}$ is —CN or —SCN. In certain embodiments, at least one instance of $R^{10}$ is —$NO_2$. In certain embodiments, at least one instance of $R^{10}$ is —$C(═NR^a)R^a$, —$C(═NR^a)OR^a$, or —$C(═NR^a)N(R^a)_2$. In certain embodiments, at least one instance of $R^{10}$ is —$C(═O)R^a$ (e.g., —C(═O) (substituted or unsubstituted alkyl) (e.g., —C(═O)Me) or —C(═O) (substituted or unsubstituted phenyl)). In certain embodiments, at least one instance of $R^{10}$ is —$C(═O)OR^a$ (e.g., —C(═O)OH, —C(═O)O (substituted or unsubstituted alkyl) (e.g., —C(═O)OMe), or —C(═O)O (substituted or unsubstituted phenyl)). In certain embodiments, at least one instance of $R^{10}$ is —C(═O)N $(R^a)_2$ (e.g., —C(═O)$NH_2$, —C(═O)NH (substituted or unsubstituted alkyl) (e.g., —C(═O)NHMe), —C(═O)NH (substituted or unsubstituted phenyl), —C(═O)N (substituted or unsubstituted alkyl)-(substituted or unsubstituted alkyl), or —C(═O)N (substituted or unsubstituted phenyl)-(substituted or unsubstituted alkyl)). In certain embodiments, at least one instance of $R^{10}$ is —$NR^aC(═O)R^a$ (e.g., —NHC(═O) (substituted or unsubstituted, $C_{1-6}$ alkyl) (e.g., —NHC(═O)Me) or —NHC(═O) (substituted or unsubstituted phenyl)). In certain embodiments, at least one instance of $R^{10}$ is —$NR^aC(═O)OR^a$. In certain embodiments, at least one instance of $R^{10}$ is —$NR^aC(═O)N(R^a)_2$ (e.g., —NHC(═O)$NH_2$, —NHC(═O)NH (substituted or unsubstituted, $C_{1-6}$ alkyl) (e.g., —NHC(═O)NHMe)). In certain embodiments, at least one instance of $R^{10}$ is —$OC(═O)R^a$ (e.g., —OC(═O) (substituted or unsubstituted alkyl) or —OC(═O) (substituted or unsubstituted phenyl)), —OC(═O)$OR^a$(e.g., —OC(═O)O (substituted or unsubstituted alkyl) or —OC(═O)O (substituted or unsubstituted phenyl)), or —OC(═O)$N(R^a)_2$ (e.g., —OC(═O)$NH_2$, —OC(═O)NH (substituted or unsubstituted alkyl), —OC(═O)NH (substituted or unsubstituted phenyl), —OC(═O)N (substituted or unsubstituted alkyl)-(substituted or unsubstituted alkyl), or —OC(═O)N (substituted or unsubstituted phenyl)-(substituted or unsubstituted alkyl)).

In certain embodiments, no instance of —$C(R^9)(R^{10})$— is —CH(Ph)-. In certain embodiments, no instance of —$C(R^9)(R^{10})$— is —CH (substituted or unsubstituted phenyl)-. In certain embodiments, no instance of $R^9$ and $R^{10}$ is unsubstituted phenyl. In certain embodiments, no instance of $R^9$ and $R^{10}$ is substituted or unsubstituted phenyl.

In certain embodiments, at least one instance of

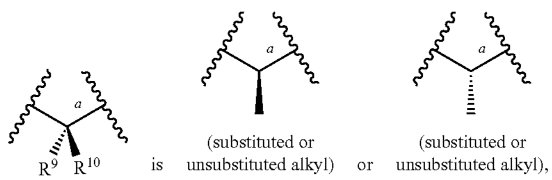

wherein bond a is attached to Ring D. In certain embodiments, at least one instance of

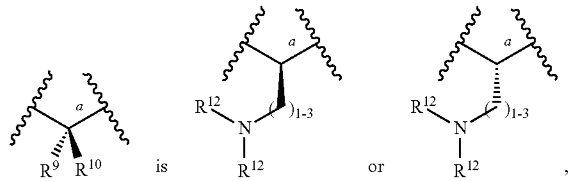

wherein bond a is attached to Ring D. In certain embodiments, at least one instance of

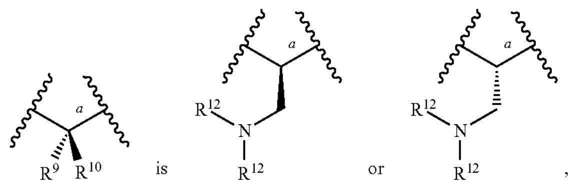

wherein bond a is attached to Ring D. In certain embodiments, at least one instance of

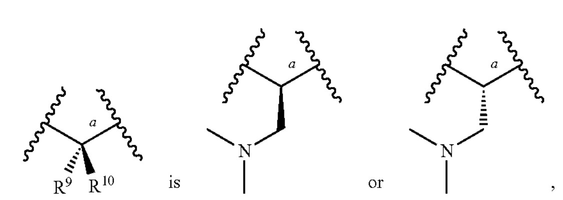

wherein bond a is attached to Ring D.

In certain embodiments,

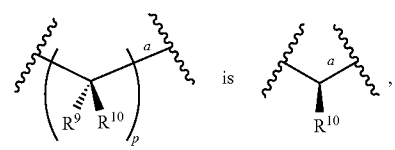

wherein bond a is attached to Ring. In certain embodiments,

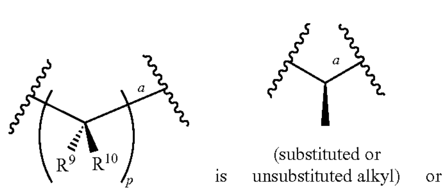

-continued

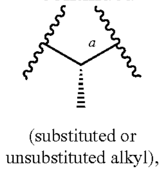

wherein bond a is attached to Ring D. In certain embodiments,

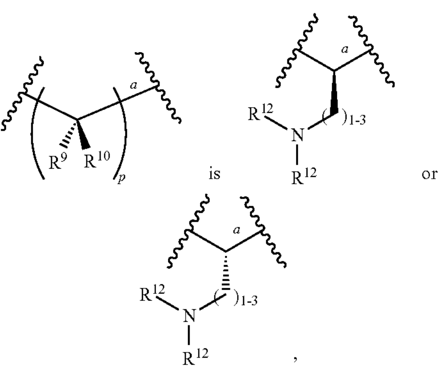

wherein bond a is attached to Ring D. In certain embodiments, wherein bond a is attached to Ring D. In certain embodiments,

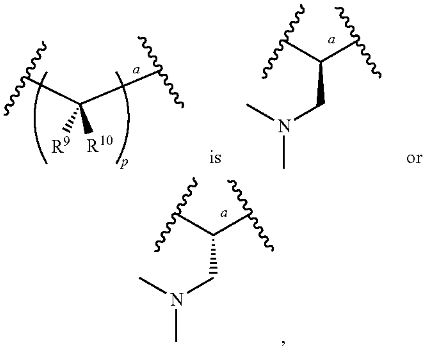

wherein bond a is attached to Ring D.

Each instance of $R^{12}$ is independently hydrogen, substituted or unsubstituted acyl, substituted or unsubstituted alkyl, substituted or unsubstituted phenyl, or a nitrogen protecting group, or two instances of $R^{12}$ are joined to form substituted or unsubstituted heterocyclyl or substituted or unsubstituted heteroaryl. In certain embodiments, at least one instance of $R^{12}$ is hydrogen. In certain embodiments, each instance of $R^{12}$ is hydrogen. In certain embodiments, no instance of $R^{12}$ is hydrogen. In certain embodiments, at least one instance of $R^{12}$ is substituted or unsubstituted acyl (e.g., —C(=O)$R^a$, —C(=O)O$R^a$, —C(=O)N($R^a$)$_2$). In certain embodiments, at least one instance of $R^{12}$ is substituted or unsubstituted alkyl (e.g., substituted or unsubstituted, $C_{1-6}$ alkyl). In certain embodiments, each instance of $R^{12}$ is substituted or unsubstituted alkyl. In certain embodiments, at least one instance of $R^{12}$ is Me. In certain embodiments, each instance of $R^{12}$ is Me. In certain embodiments, at least one instance of $R^{12}$ is Et, Pr, Bu, substituted methyl, substituted ethyl, substituted propyl, or substituted butyl. In certain embodiments, one instance of $R^{12}$ is hydrogen, and the other instance of $R^{12}$ is substituted or unsubstituted alkyl (e.g., substituted or unsubstituted, $C_{1-6}$ alkyl). In certain embodiments, one instance of $R^{12}$ is hydrogen, and the other instance of $R^{12}$ is Me. In certain embodiments, at least one instance of $R^{12}$ is substituted or unsubstituted phenyl. In certain embodiments, at least one instance of $R^{12}$ is a nitrogen protecting group (e.g., Bn, BOC, Cbz, Fmoc, trifluoroacetyl, triphenylmethyl, acetyl, Ts). In certain embodiments, two instances of $R^{12}$ are joined to form substituted or unsubstituted heterocyclyl (e.g., substituted or unsubstituted, 3- to 7-membered, monocyclic heterocyclyl). In certain embodiments, two instances of $R^{12}$ are joined to form substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, two instances of $R^{12}$ are joined to form substituted or unsubstituted heteroaryl (e.g., substituted or unsubstituted, 5- to 6-membered, monocyclic heteroaryl that comprises at least one nitrogen atom in the heteroaryl ring system).

In certain embodiments, $R^9$ and $R^{10}$ are joined to form substituted or unsubstituted carbocyclyl. In certain embodiments, $R^9$ and $R^{10}$ are joined to form an optionally substituted, monocyclic, $C_3$-$C_9$ carbocyclyl (e.g., cyclopropyl, cyclobutyl, cyclopentyl, cyclohexyl). In certain embodiments, $R^9$ and $R^{10}$ are not joined to form unsubstituted cyclopropyl. In certain embodiments, $R^9$ and $R^{10}$ are not joined to form substituted or unsubstituted cyclopropyl. In certain embodiments, $R^9$ and $R^{10}$ are not joined to form substituted or unsubstituted carbocyclyl. In certain embodiments, $R^9$ and $R^{10}$ are joined to form substituted or unsubstituted heterocyclyl. In certain embodiments, $R^9$ and $R^{10}$ are joined to form an optionally substituted, monocyclic, $C_3$-$C_9$ heterocyclyl (e.g., piperidinyl, piperizinyl, morpholinyl, pyrrolidinyl).

In certain embodiments, p is 0. In certain embodiments, p is 1. In certain embodiments, p is 2. In certain embodiments, p is 3. In certain embodiments, p is 4.

Formula (I) includes Ring D ( D ).

In certain embodiments, Ring D is carbocyclyl. In certain embodiments, Ring D is monocyclic, 3- to 7-membered carbocyclyl comprising 0, 1, or 2 double bonds in the carbocyclic ring system, as valency permits. In certain embodiments, Ring D is cyclopropyl, cyclobutyl, cyclopentyl, cyclohexyl, or cycloheptyl. In certain embodiments, Ring D is cyclopropyl. In certain embodiments,

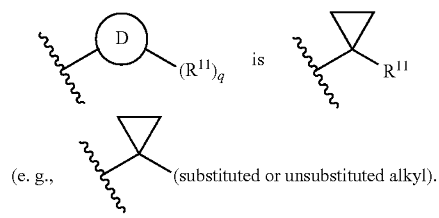

In certain embodiments,

In certain embodiments, Ring D is bicyclic, 5- to 13-membered carbocyclyl comprising 0, 1, 2, or 3 double bonds in the carbocyclic ring system, as valency permits. In certain embodiments, Ring D is monocyclic, 3- to 7-membered carbocyclyl fused to phenyl, wherein the monocyclic, 3- to 7-membered carbocyclyl comprises 0 or 1 double bond in the unfused part of the carbocyclic ring system, as valency permits.

In certain embodiments, Ring D is heterocyclyl. In certain embodiments, Ring D is monocyclic, 3- to 7-membered heterocyclyl. In certain embodiments, Ring D is monocyclic, 5- or 6-membered heterocyclyl. In certain embodiments, each heteroatom in the heterocyclic ring system of Ring D is oxygen. In certain embodiments, each heteroatom in the heterocyclic ring system of Ring D is nitrogen. In certain embodiments, Ring D is oxetanyl, tetrahydrofuranyl, tetrahydropyranyl, azetidinyl, pyrrolidinyl, piperidinyl, morpholinyl, or piperazinyl. In certain embodiments, Ring D is tetrahydropyranyl. In certain embodiments,

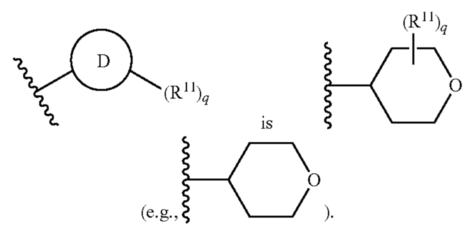

In certain embodiments, Ring D is tetrahydrofuranyl. In certain embodiments,

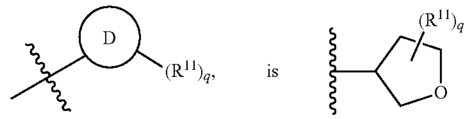

-continued

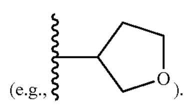

In certain embodiments, Ring D is piperazinyl. In certain embodiments,

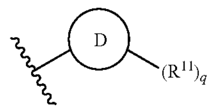

is

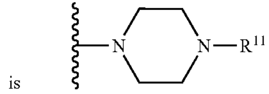

.

In certain embodiments, Ring D is morpholinyl. In certain embodiments,

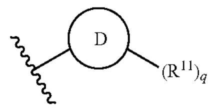

is

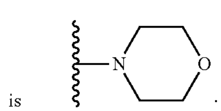

.

In certain embodiments, Ring D is piperidinyl. In certain embodiments,

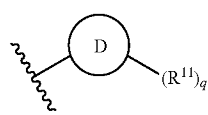

is

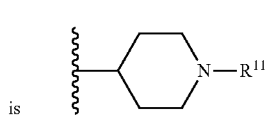

.

In certain embodiments,

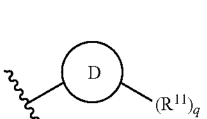

is

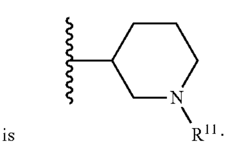

In certain embodiments,

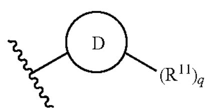

is

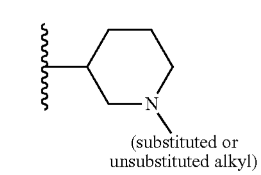

(e.g.,

).

In certain embodiments, Ring D is bicyclic, 5- to 13-membered heterocyclyl. In certain embodiments, Ring D is monocyclic, 3- to 7-membered heterocyclyl fused to phenyl. In certain embodiments,

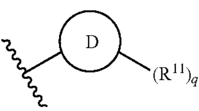

is

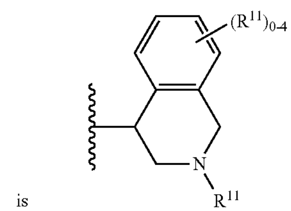

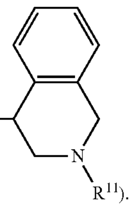

(e.g., R11).

In certain embodiments,

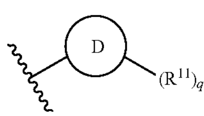

is

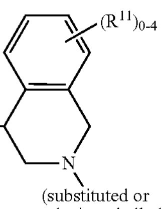

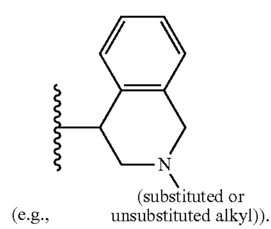

(e.g.,

In certain embodiments,

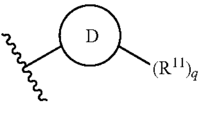

is

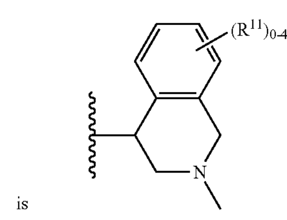

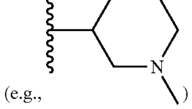

(e.g., )

In certain embodiments,

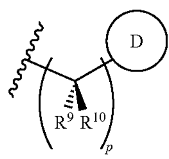

is not pyrrolidinyl. In certain embodiments,

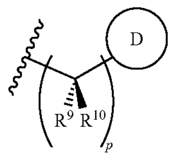

is not

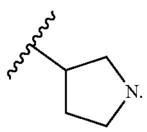

In certain embodiments,

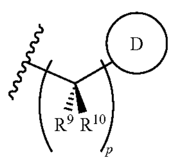

is not piperidinyl. In certain embodiments,

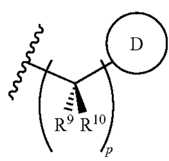

is not

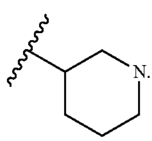

In certain embodiments, when p is 0, Ring D does not comprise one or more nitrogen atoms in the ring system. In certain embodiments, when p is 2, Ring D is not pyrrolidinyl. In certain embodiments, when p is 2, Ring D is not morpholinyl. In certain embodiments, when p is 1, Ring D is not cyclohexyl.

Ring D may include one or more substituents $R^{11}$. $R^{11}$ may attach to any atom of the carbocyclic or heterocyclic ring system (e.g., monocyclic or bicyclic ring system) of Ring D, as valency permits. In certain embodiments, at least one instance of $R^{11}$ is halogen (e.g., F, Cl, Br, I). In certain embodiments, at least one instance of $R^{11}$ is substituted or unsubstituted, $C_{1-3}$ alkyl. In certain embodiments, at least one instance of $R^{11}$ is substituted alkyl (e.g., alkyl substituted with one or more instances of halogen (e.g., F)). In certain embodiments, at least one instance of $R^{11}$ is alkyl substituted with at least —$N(R^a)_2$. In certain embodiments, at least one instance of $R^{11}$ is —$(CH_2)_{1-3}$—N (substituted or unsubstituted alkyl)$_2$ (e.g., —$CH_2$—N (substituted or unsubstituted alkyl)$_2$). In certain embodiments, at least one instance of $R^{11}$ is —$CH_2$—$N(CH_3)_2$. In certain embodiments, at least one instance of $R^{11}$ is unsubstituted alkyl. In certain embodiments, at least one instance of $R^{11}$ is unsubstituted, $C_{1-6}$ alkyl. In certain embodiments, at least one instance of $R^{11}$ is Me. In certain embodiments, at least one instance of $R^{11}$ is Et, Pr, or Bu. In certain embodiments, at least one instance of $R^{11}$ is substituted $C_{1-6}$ alkyl. In certain embodiments, at least one instance of $R^{11}$ is substituted methyl (e.g., —$CF_3$, —$CF_2H$, —$CFH_2$). In certain embodiments, at least one instance of $R^{11}$ is substituted ethyl, substituted propyl, or substituted butyl. In certain embodiments, at least one instance of $R^{11}$ is hydrogen, halogen, or substituted or unsubstituted alkyl. In certain embodiments, at least one instance of $R^{11}$ is substituted or unsubstituted alkenyl. In certain embodiments, at least one instance of $R^{11}$ is substituted or unsubstituted, $C_{2-6}$ alkenyl (e.g., substituted or unsubstituted vinyl or substituted or unsubstituted allyl). In certain embodiments, at least one instance of $R^{11}$ is substituted or unsubstituted alkynyl. In certain embodiments, at least one instance of $R^{11}$ is substituted or unsubstituted, $C_{2-6}$ alkynyl (substituted or unsubstituted ethynyl). In certain embodiments, at least one instance of $R^{11}$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^{11}$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^{11}$ is substituted or unsubstituted heterocyclyl (e.g., substituted or unsubstituted, 3- to 7-membered, monocyclic heterocyclyl). In certain embodiments, at least one instance of $R^{11}$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^{11}$ is substituted or unsubstituted aryl. In certain embodiments, at least one instance of $R^{11}$ is substituted or unsubstituted phenyl. In certain embodiments, at least one instance of $R^{11}$ is substituted or unsubstituted naphthyl. In certain embodiments, at least one instance of $R^{11}$ is substituted or unsubstituted heteroaryl. In certain embodiments, at least one instance of $R^{11}$ is substituted or unsubstituted, 5- to 6-membered, monocyclic heteroaryl. In certain embodiments, at least one instance of $R^{11}$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^{11}$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^{11}$ is substituted or unsubstituted, 9- to 11-membered, bicyclic heteroaryl. In certain embodiments, at least one instance of $R^{11}$ is —$OR^a$ (e.g., —OH, —O (substituted or unsubstituted, $C_{1-6}$ alkyl) (e.g., —OMe, —$OCF_3$, —OEt, —OPr, —OBu, or —OBn), or —O (substituted or unsubstituted phenyl) (e.g., —OPh)). In certain embodiments, at least one instance of $R^{11}$ is —OMe. In certain embodiments, at least one instance of $R^{11}$ is —$SR^a$ (e.g., —SH, —S (substituted or unsubstituted, $C_{1-6}$ alkyl) (e.g., —SMe, —$SCF_3$, —SEt, —SPr, —SBu, or —SBn), or —S (substituted or unsubstituted phenyl) (e.g., —SPh)). In certain embodiments, at least one instance of $R^{11}$ is —$N(R^a)_2$ (e.g., —$NH_2$, —NH (substituted or unsubstituted, $C_{1-6}$ alkyl) (e.g., —NHMe), or —N (substituted or unsubstituted, $C_{1-6}$ alkyl)-(substituted or unsubstituted, $C_{1-6}$ alkyl) (e.g., —$NMe_2$)). In certain embodiments, at least one instance of $R^{11}$ is —CN or —SCN. In certain embodiments, at least one instance of $R^{11}$ is —$NO_2$. In certain embodiments, at least one instance of $R^{11}$ is —C(=$NR^a$)$R^a$, —C(=$NR^a$)$OR^a$, or —C(=$NR^a$)N($R^a$)$_2$. In certain embodiments, at least one instance of $R^{11}$ is —C(=O)$R^a$ (e.g., —C(=O) (substituted or unsubstituted alkyl) (e.g., —C(=O)Me) or —C(=O) (substituted or unsubstituted phenyl)). In certain embodiments, at least one instance of $R^{11}$ is —C(=O)$OR^a$(e.g., —C(=O)OH, —C(=O)O (substituted or unsubstituted alkyl) (e.g., —C(=O)OMe), or —C(=O)O (substituted or unsubstituted phenyl)). In certain embodiments, at least one instance of $R^{11}$ is —C(=O)N($R^a$)$_2$ (e.g., —C(=O)$NH_2$, —C(=O)NH (substituted or unsubstituted alkyl) (e.g., —C(=O)NHMe), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, at least one instance of $R^{11}$ is —$NR^a$C(=O)$R^a$ (e.g., —NHC(=O) (substituted or unsubstituted, $C_{1-6}$ alkyl) (e.g., —NHC(=O)Me) or —NHC(=O) (substituted or unsubstituted phenyl)). In certain embodiments, at least one instance of $R^{11}$ is —$NR^a$C(=O)$OR^a$. In certain embodiments, at least one instance of $R^{11}$ is —$NR^a$C(=O)N($R^a$)$_2$ (e.g., —NHC(=O)$NH_2$, —NHC(=O)NH (substituted or unsubstituted, $C_{1-6}$ alkyl) (e.g., —NHC(=O)NHMe)). In certain embodiments, at least one instance of $R^{11}$ is —OC(=O)$R^a$ (e.g., —OC(=O) (substituted or unsubstituted alkyl) or —OC(=O) (substituted or unsubstituted phenyl)), —OC(=O)$OR^a$ (e.g., —OC(=O)O (substituted or unsubstituted alkyl) or —OC(=O)O (substituted or unsubstituted phenyl)), or —OC(=O)N($R^a$)$_2$ (e.g., —OC(=O)$NH_2$, —OC(=O)NH (substituted or unsubstituted alkyl), —OC(=O)NH (substituted or unsubstituted phenyl), —OC(=O)N (substituted or unsubstituted alkyl)-(substituted or unsubstituted alkyl), or —OC(=O)N (substituted or unsubstituted phenyl)-(substituted or unsubstituted alkyl)). In certain embodiments, at least one instance of $R^{11}$ is a nitrogen protecting group (e.g., Bn, Boc, Cbz, Fmoc, trifluoroacetyl, triphenylmethyl, acetyl, Ts).

In certain embodiments, q is 0. In certain embodiments, q is 1. In certain embodiments, q is 2. In certain embodiments, q is 3, 4, 5, 6, 7, 8, 9, 10, or 11.

In certain embodiments, at least one instance of $R^a$ is hydrogen. In certain embodiments, each instance of $R^a$ is hydrogen. In certain embodiments, at least one instance of $R^a$ is not hydrogen. In certain embodiments, no instance of $R^a$ is hydrogen. In certain embodiments, at least one instance of $R^a$ is substituted alkyl (e.g., alkyl substituted with one or more instances of halogen (e.g., F)). In certain embodiments, at least one instance of $R^a$ is unsubstituted alkyl. In certain embodiments, at least one instance of $R^a$ is unsubstituted, $C_{1-6}$ alkyl. In certain embodiments, at least one instance of $R^a$ is Me. In certain embodiments, at least one instance of $R^a$ is Et, Pr, or Bu. In certain embodiments, at least one instance of $R^a$ is substituted $C_{1-6}$ alkyl. In certain embodiments, at least one instance of $R^a$ is substituted methyl. In certain embodiments, at least one instance of $R^a$ is substituted ethyl, substituted propyl, or substituted butyl. In certain embodiments, at least one instance of $R^a$ is substituted or unsubstituted alkenyl. In certain embodiments, at least one instance of $R^a$ is substituted or unsubstituted, $C_{2-6}$ alkenyl (e.g., substituted or unsubstituted vinyl or substituted or unsubstituted allyl). In certain embodiments, at least one instance of $R^a$ is substituted or unsubstituted alkynyl. In certain embodiments, at least one instance of $R^a$ is substituted or unsubstituted, $C_{2-6}$ alkynyl (substituted or unsubstituted ethynyl). In certain embodiments, at least one instance of $R^a$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^a$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^a$ is substituted or unsubstituted heterocyclyl (e.g., substituted or unsubstituted, 3- to 7-membered, monocyclic heterocyclyl). In certain embodiments, at least one instance of $R^a$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^a$ is substituted or unsubstituted aryl. In certain embodiments, at least one instance of $R^a$ is substituted or unsubstituted phenyl. In certain embodiments, at least one instance of $R^a$ is substituted or unsubstituted naphthyl. In certain embodiments, at least one instance of $R^a$ is substituted or unsubstituted heteroaryl. In certain embodiments, at least one instance of $R^a$ is substituted or unsubstituted, 5- to 6-membered, monocyclic heteroaryl. In certain embodiments, at least one instance of $R^a$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^a$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^a$ is substituted or unsubstituted, 9- to 10-membered, bicyclic heteroaryl. In certain embodiments, at least one instance of $R^a$ is a nitrogen protecting group (e.g., Bn, Boc, Cbz, Fmoc, trifluoroacetyl, triphenylmethyl, acetyl, or Ts) when attached to a nitrogen atom. In certain embodiments, at least one instance of $R^a$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, two instances of $R^a$ are joined to form substituted or unsubstituted heterocyclyl (e.g., substituted or unsubstituted, 3- to 7-membered, monocyclic heterocyclyl).

In certain embodiments, two instances of $R^a$ are joined to form substituted or unsubstituted heteroaryl (e.g., substituted or unsubstituted, 5- to 6-membered, monocyclic heteroaryl).

In certain embodiments, the compound is of the formula:

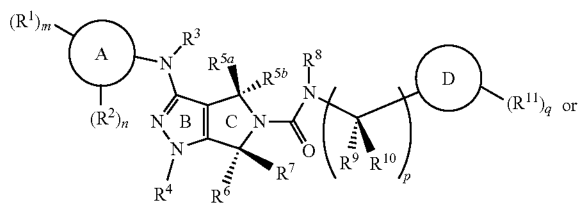

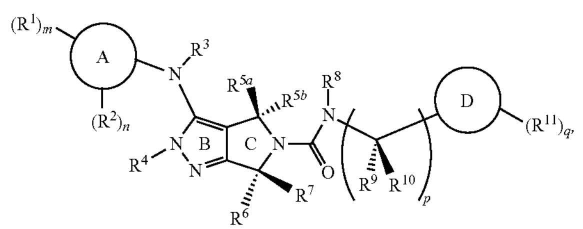

or a pharmaceutically acceptable salt, solvate, hydrate, polymorph, co-crystal, tautomer, stereoisomer, isotopically labeled derivative, or prodrug thereof.

In certain embodiments, the compound is of the formula:

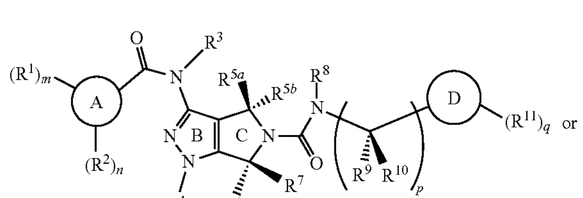

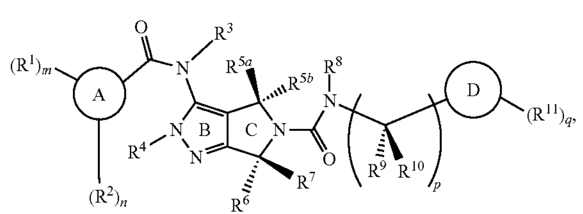

or a pharmaceutically acceptable salt, solvate, hydrate, polymorph, co-crystal, tautomer, stereoisomer, isotopically labeled derivative, or prodrug thereof.

In certain embodiments, the compound is of the formula:

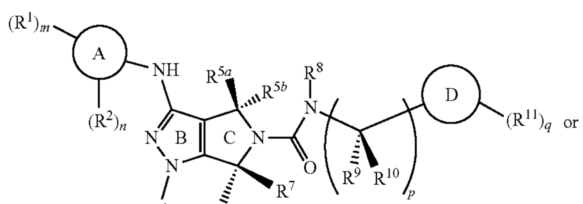

-continued

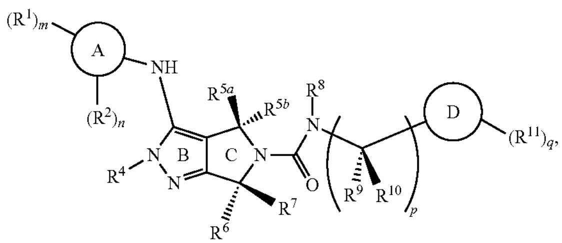

or a pharmaceutically acceptable salt, solvate, hydrate, polymorph, co-crystal, tautomer, stereoisomer, isotopically labeled derivative, or prodrug thereof.

In certain embodiments, the compound is of the formula:

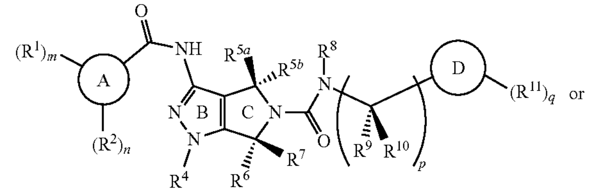

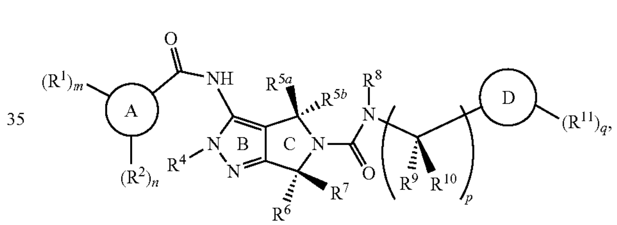

or a pharmaceutically acceptable salt, solvate, hydrate, polymorph, co-crystal, tautomer, stereoisomer, isotopically labeled derivative, or prodrug thereof.

In certain embodiments, the compound is of the formula:

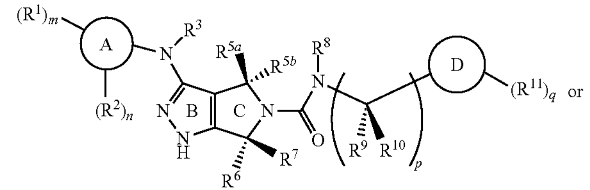

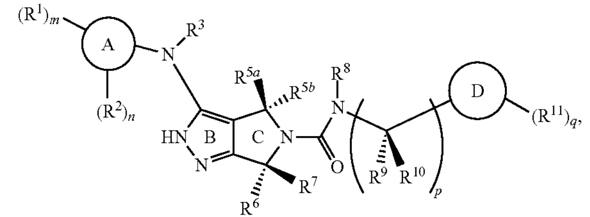

or a pharmaceutically acceptable salt, solvate, hydrate, polymorph, co-crystal, tautomer, stereoisomer, isotopically labeled derivative, or prodrug thereof.

In certain embodiments, the compound is of the formula:

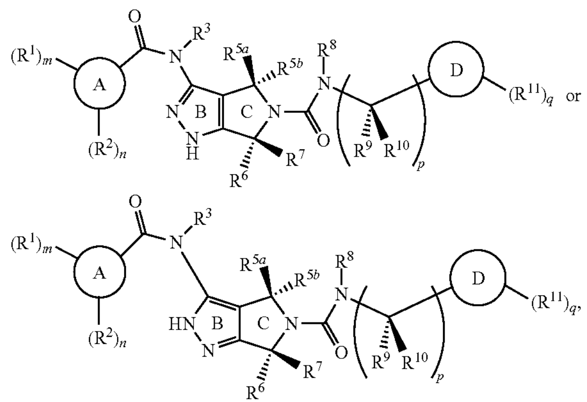

or a pharmaceutically acceptable salt, solvate, hydrate, polymorph, co-crystal, tautomer, stereoisomer, isotopically labeled derivative, or prodrug thereof.

In certain embodiments, the compound is of the formula:

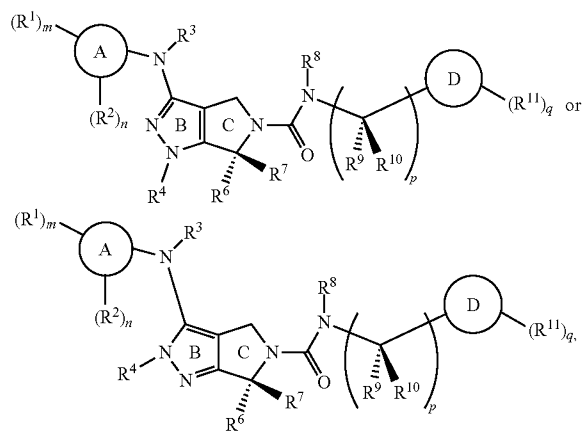

or a pharmaceutically acceptable salt, solvate, hydrate, polymorph, co-crystal, tautomer, stereoisomer, isotopically labeled derivative, or prodrug thereof.

In certain embodiments, the compound is of the formula:

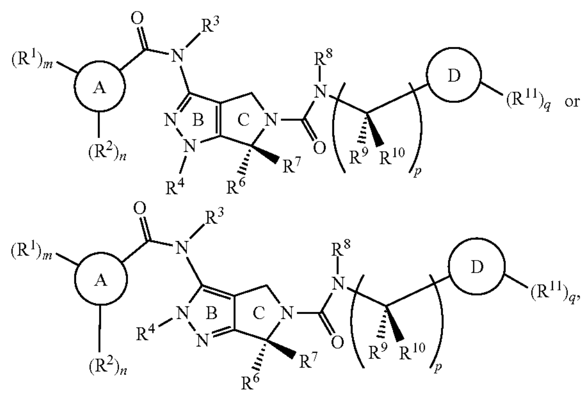

or a pharmaceutically acceptable salt, solvate, hydrate, polymorph, co-crystal, tautomer, stereoisomer, isotopically labeled derivative, or prodrug thereof.

In certain embodiments, the compound is of the formula:

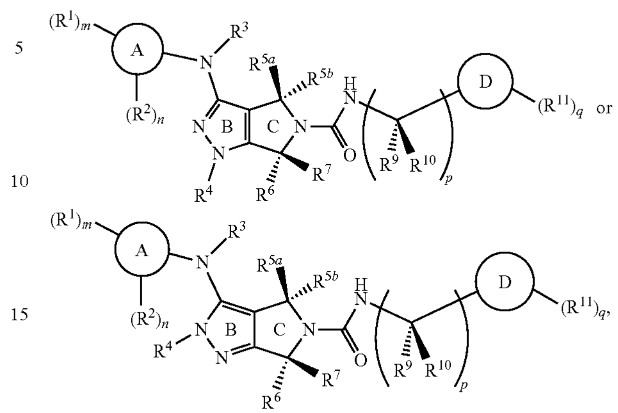

or a pharmaceutically acceptable salt, solvate, hydrate, polymorph, co-crystal, tautomer, stereoisomer, isotopically labeled derivative, or prodrug thereof.

In certain embodiments, the compound is of the formula:

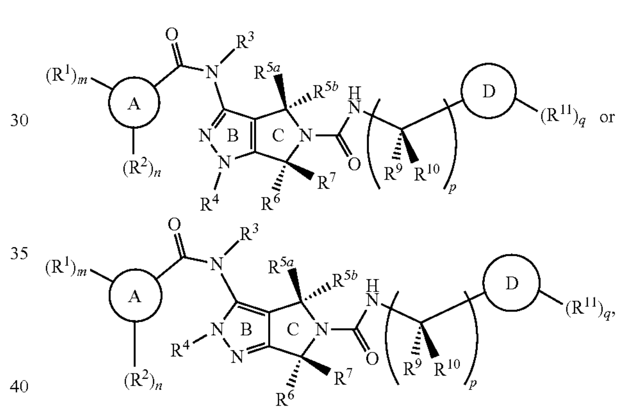

or a pharmaceutically acceptable salt, solvate, hydrate, polymorph, co-crystal, tautomer, stereoisomer, isotopically labeled derivative, or prodrug thereof.

In certain embodiments, the compound is of the formula:

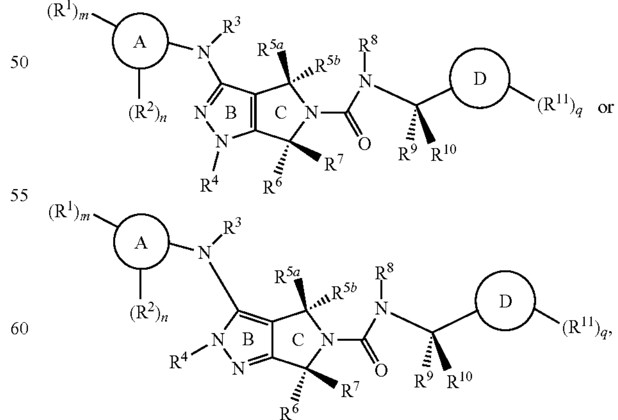

or a pharmaceutically acceptable salt, solvate, hydrate, polymorph, co-crystal, tautomer, stereoisomer, isotopically labeled derivative, or prodrug thereof.

In certain embodiments, the compound is of the formula:

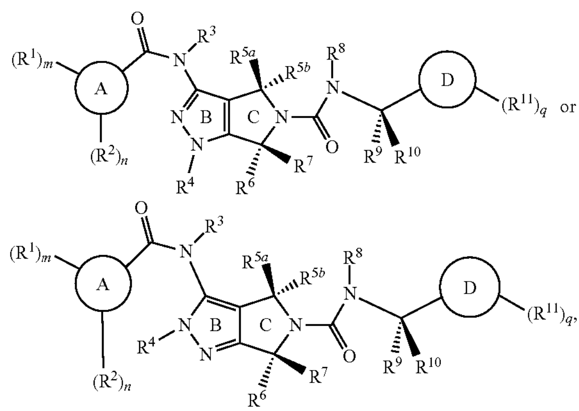

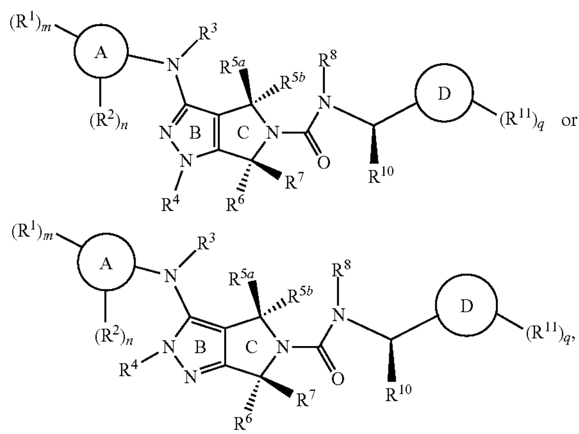

or a pharmaceutically acceptable salt, solvate, hydrate, polymorph, co-crystal, tautomer, stereoisomer, isotopically labeled derivative, or prodrug thereof.

In certain embodiments, the compound is of the formula:

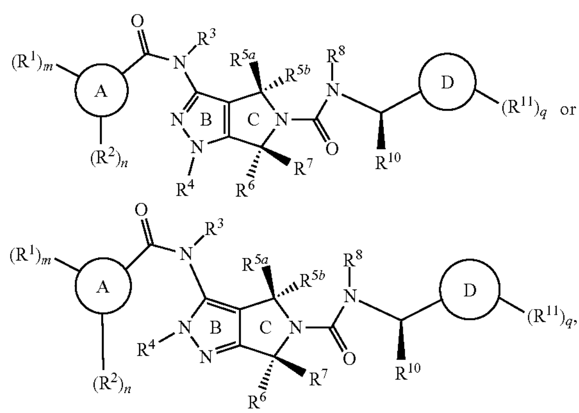

or a pharmaceutically acceptable salt, solvate, hydrate, polymorph, co-crystal, tautomer, stereoisomer, isotopically labeled derivative, or prodrug thereof, provided that $R^{10}$ is not hydrogen.

In certain embodiments, the compound is of the formula:

or a pharmaceutically acceptable salt, solvate, hydrate, polymorph, co-crystal, tautomer, stereoisomer, isotopically labeled derivative, or prodrug thereof, provided that $R^{10}$ is not hydrogen.

In certain embodiments, the compound is of the formula:

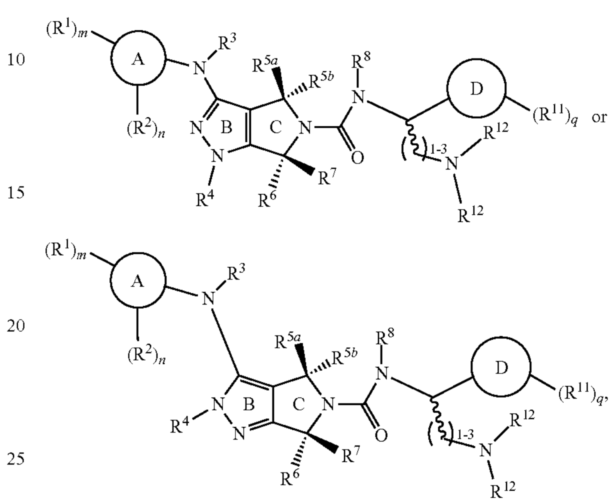

or a pharmaceutically acceptable salt, solvate, hydrate, polymorph, co-crystal, tautomer, stereoisomer, isotopically labeled derivative, or prodrug thereof, optionally

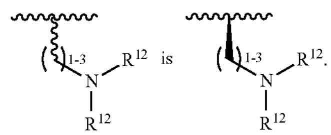

In certain embodiments, the compound is of the formula:

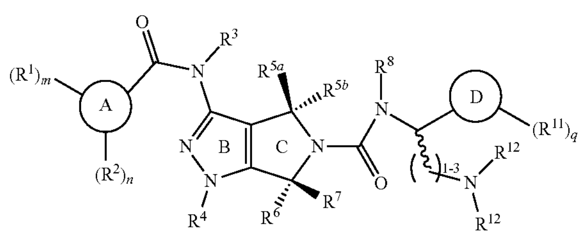

or

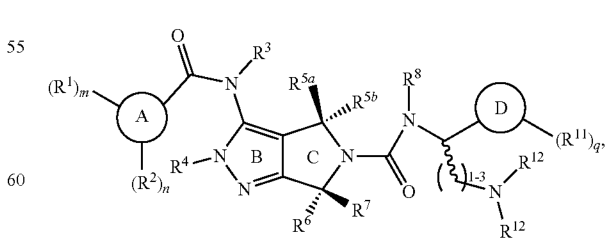

or a pharmaceutically acceptable salt, solvate, hydrate, polymorph, co-crystal, tautomer, stereoisomer, isotopically labeled derivative, or prodrug thereof, optionally

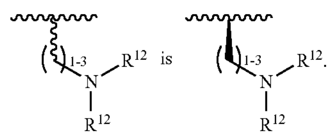

In certain embodiments, the compound is of the formula:

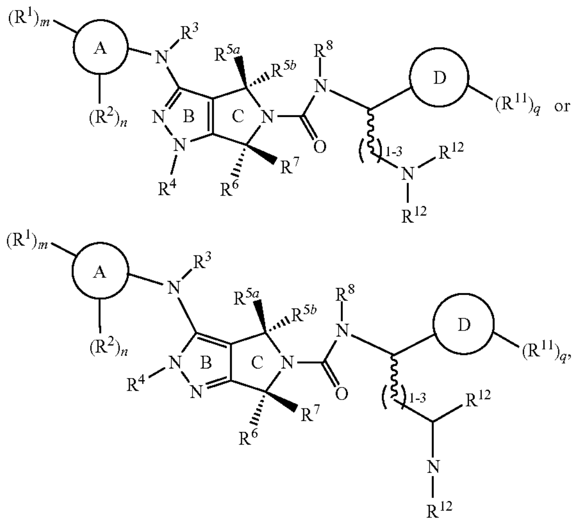

or a pharmaceutically acceptable salt, solvate, hydrate, polymorph, co-crystal, tautomer, stereoisomer, isotopically labeled derivative, or prodrug thereof, optionally

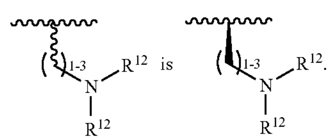

In certain embodiments, the compound is of the formula:

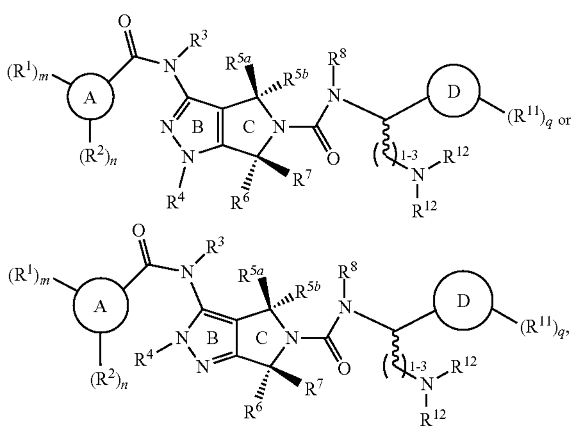

or a pharmaceutically acceptable salt, solvate, hydrate, polymorph, co-crystal, tautomer, stereoisomer, isotopically labeled derivative, or prodrug thereof, optionally

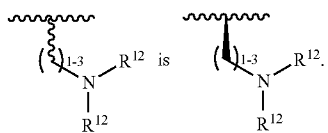

In certain embodiments, the compound is of the formula:

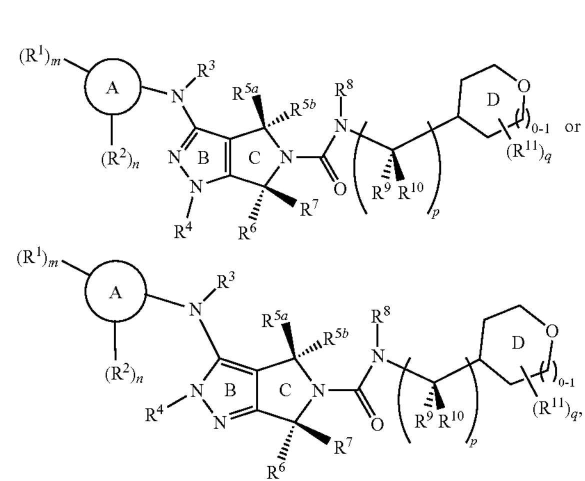

or a pharmaceutically acceptable salt, solvate, hydrate, polymorph, co-crystal, tautomer, stereoisomer, isotopically labeled derivative, or prodrug thereof.

In certain embodiments, the compound is of the formula:

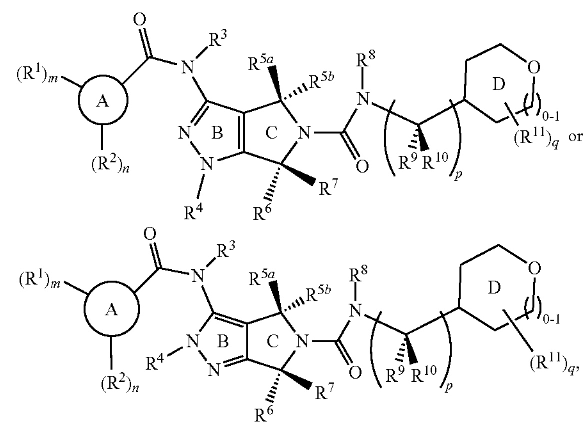

or a pharmaceutically acceptable salt, solvate, hydrate, polymorph, co-crystal, tautomer, stereoisomer, isotopically labeled derivative, or prodrug thereof.

In certain embodiments, the compound is of the formula:

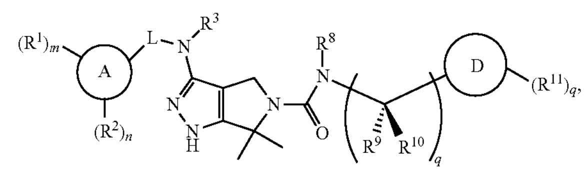

or a pharmaceutically acceptable salt, solvate, hydrate, polymorph, co-crystal, tautomer, stereoisomer, isotopically labeled derivative, or prodrug thereof.

In certain embodiments, the compound is of the formula:

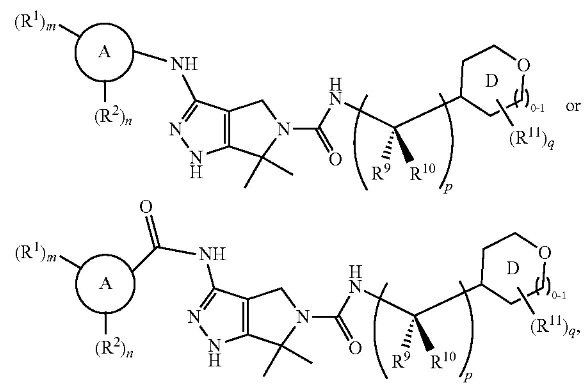

or a pharmaceutically acceptable salt, solvate, hydrate, polymorph, co-crystal, tautomer, stereoisomer, isotopically labeled derivative, or prodrug thereof.

In certain embodiments, the compound is of the formula:

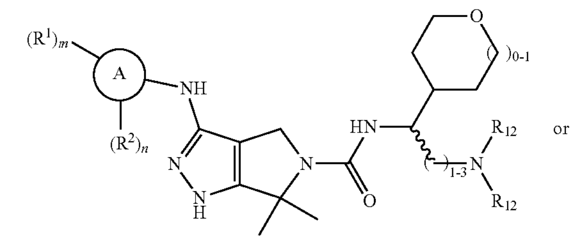

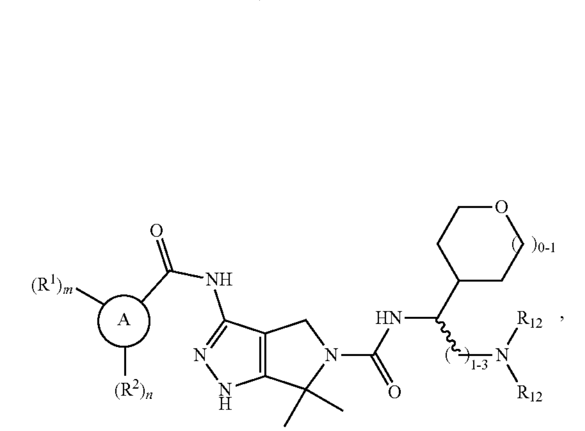

or a pharmaceutically acceptable salt, solvate, hydrate, polymorph, co-crystal, tautomer, stereoisomer, isotopically labeled derivative, or prodrug thereof, optionally

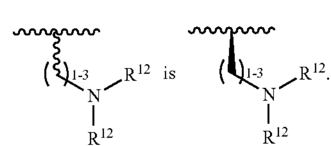

In certain embodiments, the compound is of the formula:

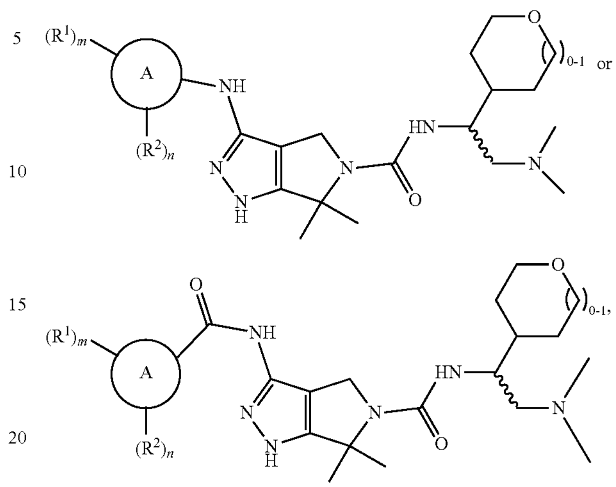

or a pharmaceutically acceptable salt, solvate, hydrate, polymorph, co-crystal, tautomer, stereoisomer, isotopically labeled derivative, or prodrug thereof, optionally is In certain embodiments, the compound is of the formula:

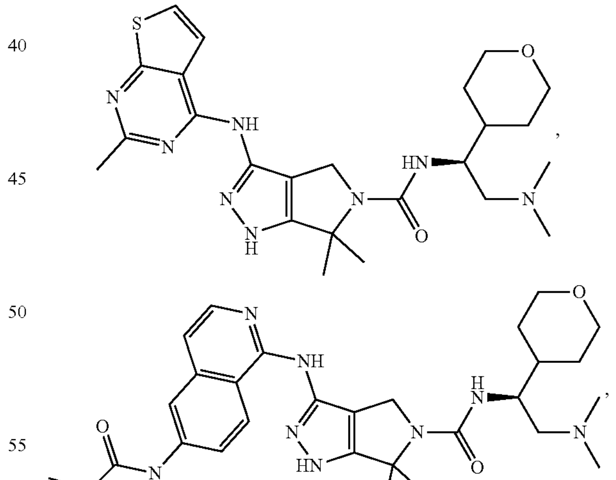

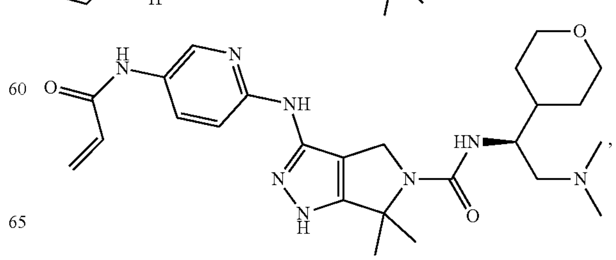

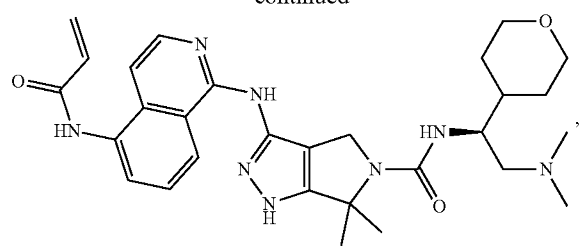

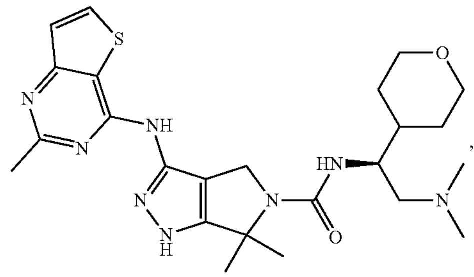

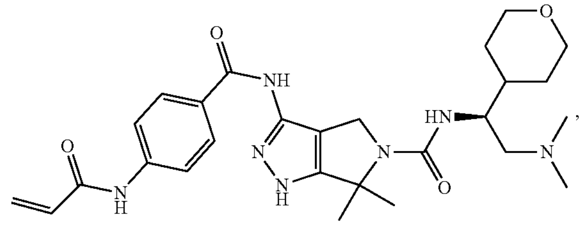

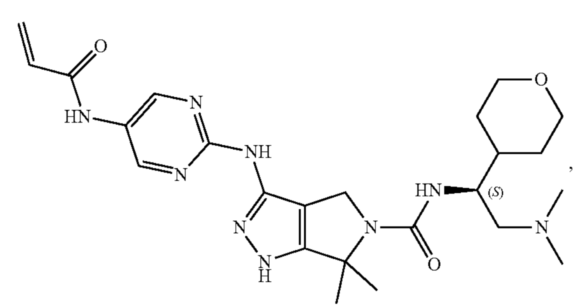

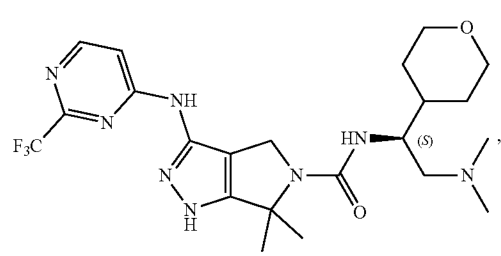

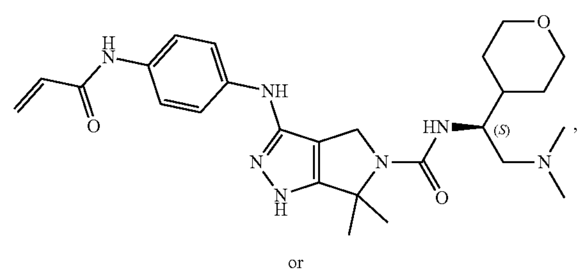

or

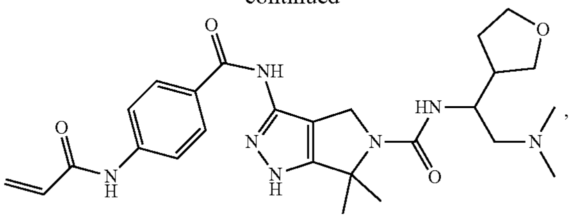

or a pharmaceutically acceptable salt, solvate, hydrate, polymorph, co-crystal, tautomer, stereoisomer, isotopically labeled derivative, or prodrug thereof.

In certain embodiments, the compound is of the formula:

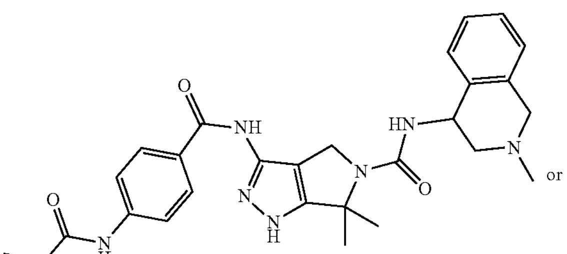

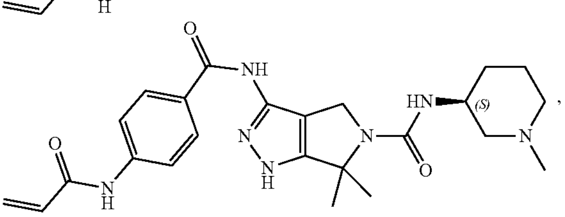

or a pharmaceutically acceptable salt, solvate, hydrate, polymorph, co-crystal, tautomer, stereoisomer, isotopically labeled derivative, or prodrug thereof.

In certain embodiments, the compound is of the formula:

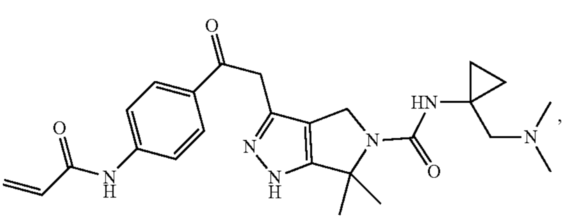 [SMILES: C=CC(=O)Nc1ccc(C(=O)Cc2n[nH]c3c2CN(C(=O)NC2(CN(C)C)CC2)C3(C)C)cc1]

or a pharmaceutically acceptable salt, solvate, hydrate, polymorph, co-crystal, tautomer, stereoisomer, isotopically labeled derivative, or prodrug thereof.

In certain embodiments, a provided compound (a compound described herein, a compound of the present disclosure) is a compound of Formula (I), or a pharmaceutically acceptable salt, solvate, hydrate, polymorph, co-crystal, tautomer, stereoisomer, isotopically labeled derivative, or prodrug thereof. In certain embodiments, a provided compound is a compound of Formula (I), or a pharmaceutically acceptable salt, solvate, hydrate, tautomer, or stereoisomer thereof. In certain embodiments, a provided compound is a compound of Formula (I), or a pharmaceutically acceptable salt, tautomer, or stereoisomer thereof. In certain embodiments, a provided compound is a compound of Formula (I), or a pharmaceutically acceptable salt thereof. In certain embodiments, a provided compound is a mixture of tautomers. In certain embodiments, a provided compound is a mixture (e.g., a racemic mixture) of enantiomers and/or diastereomers.

In certain embodiments, the molecular weight of a provide compound that is not in the form of a salt, solvate, hydrate, co-crystal, or prodrug is lower than 2,000, lower than 1,500, lower than 1,200, lower than 1,000, lower than 800, lower than 700, or lower than 600 g/mol. In certain embodiments, the molecular weight of a provided compound that is not in the form of a salt, solvate, hydrate, co-crystal, or prodrug is lower than 1000 g/mol. In certain embodiments, the molecular weight of a provide compound that is not in the form of a salt, solvate, hydrate, co-crystal, or prodrug is lower than 600 g/mol.

In certain embodiments, a provided compound inhibits the activity (e.g., aberrant activity (e.g., higher-than-normal activity, increased activity)) of a kinase. In certain embodiments, the kinase is a CDK (e.g., wild-type or mutant CDK). In certain embodiments, the kinase is is CDK1, CDK2, CDK3, CDK4, CDK5, CDK6, CDK7, CDK8, CDK9, CDK10, CDK11, CDK12, CDK13, CDK14, CDK15, CDK16, CDK17, CDK18, CDK19, or CDK20. In certain embodiments, the kinase is CDK7 (e.g., wild-type or mutant CDK7). In certain embodiments, the kinase is CDK2. In certain embodiments, the kinase is CDK9. In certain embodiments, the kinase is CDK12. In certain embodiments, the kinase is a human kinase. In certain embodiments, the kinase is a non-human mammalian kinase. In certain embodiments, the kinase is a wild type kinase. In certain embodiments, the kinase is a mutant kinase. In certain embodiments, a provided compound inhibits the activity of a kinase as measured in an assay described herein or known in the art. In certain embodiments, a provided compound inhibits the activity of the kinase at an $IC_{50}$ less than or equal to 30 μM, less than or equal to 10 μM, less than or equal to 3 μM, less than or equal to 1 μM, less than or equal to 0.3 μM, or less than or equal to 0.1 μM.

It has been reported that certain CDK7 inhibitors also inhibit the activity of CDK12 and/or CDK13 (Kwiatowski et al., *Nature,* 511, 616-620 (2014)). The compounds of the present disclosure may be selective for inhibiting the activity of a first kinase over a second kinase, wherein the first and second kinases are different from each other. In certain embodiments, the first kinase is a CDK. In certain embodiments, the first kinase is a CDK7. In certain embodiments, the second kinase is a kinase that is not a CDK (e.g., a kinase that is not CDK7). In certain embodiments, the second kinase is CDK2, CDK9, or CDK12. The selectivity of a compound or pharmaceutical composition of the present disclosure in inhibiting the activity of a first kinase over a second kinase may be measured by the quotient of the $IC_{50}$ value of the compound or pharmaceutical composition in inhibiting the activity of the second kinase over the $IC_{50}$ value of the compound or pharmaceutical composition in inhibiting the activity of the first kinase. The selectivity of a compound or pharmaceutical composition of the present disclosure in inhibiting the activity of a first kinase over a second kinase may also be measured by the quotient of the $K_d$ value of an adduct of the compound or pharmaceutical composition and the second kinase over the $K_d$ value of an adduct of the compound or pharmaceutical composition and the first kinase. In certain embodiments, a provided compound is selective for inhibiting the activity of the first kinase over the second kinase by at least 2-fold, at least 3-fold, at least 4-fold, at least 5-fold, at least 7-fold, at least 10-fold, at least 20-fold, at least 50-fold, at least 100-fold, at least 300-fold, or at least 1,000-fold (e.g., in an in vitro assay or an assay described herein). In certain embodiments, a provided compound is selective for inhibiting the activity of the first kinase over the second kinase by at most 3-fold, at most 4-fold, at most 5-fold, at most 7-fold, at most 10-fold, at most 20-fold, at most 50-fold, at most 100-fold, at most 300-fold, or at most 1,000-fold (e.g., in an in vitro assay or an assay described herein). The compounds of the present disclosure may be advantageous over non-selective or less selective kinase inhibitors in treating and/or preventing the diseases in the subjects in need thereof. The compounds of the present disclosure may be more selective for inhibiting the activity of a CDK (e.g., CDK7) over other kinases (e.g., kinases other than CDKs, kinases other than CDK7, CDKs other than CDK7) than other compounds (e.g., non-selective kinase inhibitors, less selective kinase inhibitors). In certain embodiments, a provided compound is more selective for inhibiting the activity of CDK7 over CDK2 (e.g., by at least 2-fold, at least 3-fold, at least 4-fold, at least 5-fold, at least 7-fold, at least 10-fold, at least 20-fold, at least 50-fold, at least 100-fold, at least 300-fold, or at least 1,000-fold). In certain embodiments, a provided compound is more selective for inhibiting the activity of CDK7 over CDK9 (e.g., by at least 2-fold, at least 3-fold, at least 4-fold, at least 5-fold, at least 7-fold, at least 10-fold, at least 20-fold, at least 50-fold, at least 100-fold, at least 300-fold, or at least 1,000-fold). In certain embodiments, a provided compound is more selective for inhibiting the activity of CDK7 over CDK12 (e.g., by at least 2-fold, at least 3-fold, at least 4-fold, at least 5-fold, at least 7-fold, at least 10-fold, at least 20-fold, at least 50-fold, at least 100-fold, at least 300-fold, or at least 1,000-fold). In certain embodiments, a provided compound reversibly (e.g., non-covalently) binds to a kinase. In certain embodiments, a provided compound irreversibly (e.g., covalently) binds to a kinase. Certain compounds of the present disclosure may be able to covalently modify a cysteine residue located outside of the canonical kinase domain (e.g., Cys312) of CDK7. Cys312 is exclusively found in CDK7. Without wishing to be bound by any particular theory, the ability of certain compounds disclosed here to covalently modify Cys312 of CDK7 may contribute to one or more of the above advantages (e.g., selectivity for inhibiting the activity of CDK7 over certain other kinases (e.g., CDKs other than CDK7)) of these compounds over certain other compounds. Irreversible binding of certain compounds of the present disclosure to CDK7 may result in prolonged disruption of transcription and the induction of apoptosis in certain malignant cells and/or premalignant cells. Genome-wide transcript analysis following inhibitor treatment delineates CDK7-responsive genes as important in the maintenance of the malignant or premalignant cell state, in particular MYC and MCL-1 genes. Selective inhibition of CDK7 may be a useful in treating or preventing proliferative diseases.

Compared to other compounds, the compounds of the present disclosure may also be more potent, more efficacious, and/or less toxic when used in treating and/or preventing a disease in a subject in need thereof. Compared to other compounds, the compounds of the present disclosure may also decrease the frequency of side effects, decrease the severity of side effects, increase subject compliance, and/or decrease resistance when used in treating and/or preventing a disease in a subject in need thereof. Moreover, the compounds of the present disclosure may be more soluble, more permeable, more microsomally stable, and/or more bioavailable, and/or may show improved pharmacokinetic properties compared to other compounds. The compounds of the present disclosure include carbocyclyl or heterocyclyl as Ring D. Without wishing to be bound by any particular theory, Ring D may contribute to one or more of the above advantages of the compounds of the present disclosure over certain other compounds.

In another aspect, the present disclosure provides methods of preparing a compound described herein. In certain embodiments, the method of preparing is a method described herein (e.g., a method described in Example 1).

Pharmaceutical Compositions, Kits, and Administration

In another aspect, the present disclosure provides pharmaceutical compositions comprising a compound of the present disclosure, and optionally a pharmaceutically acceptable excipient. In certain embodiments, the pharmaceutical composition of the present disclosure includes an effective amount of the compound of the present disclosure.

The pharmaceutical compositions of the present disclosure may be useful in treating and/or preventing diseases (e.g., proliferative diseases (e.g., cancer, benign neoplasm, inflammatory diseases, autoimmune diseases, pathological angiogenesis), cystic fibrosis) in a subject in need thereof. The compositions of the present disclosure may also be useful for inhibiting the activity of a protein kinase (e.g., CDK) in a subject, biological sample, tissue, or cell. The compositions of the present disclosure are useful for treating and/or preventing a disease associated with overexpression or aberrant activity of a cyclin-dependent kinase (CDK). The compositions of the present disclosure may also be useful for inducing apoptosis in a cell (e.g., malignant cell or premalignant cell).

In certain embodiments, the effective amount is a therapeutically effective amount (e.g., amount effective for treating a disease in a subject in need thereof). In certain embodiments, the effective amount is an amount effective for inhibiting the activity of a protein kinase (e.g., CDK (e.g., CDK7)) in a subject in need thereof. In certain embodiments, the effective amount is an amount effective for inhibiting the activity of a protein kinase (e.g., CDK (e.g., CDK7)) in a subject, biological sample, tissue, or cell. In certain embodiments, the effective amount is an amount effective for inducing apoptosis in a cell. In certain embodiments, the effective amount is a prophylactically effective amount (e.g., amount effective for preventing a disease in a subject in need thereof and/or for keeping a subject in need thereof in remission of a disease).

In certain embodiments, the effective amount is an amount effective for inhibiting the activity of a protein kinase (e.g., CDK (e.g., CDK7)) by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a protein kinase (e.g., CDK (e.g., CDK7)) by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a protein kinase (e.g., CDK (e.g., CDK7)) by a range between a percentage described in this paragraph and another percentage described in this paragraph, inclusive.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a dog. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice, transgenic pigs). In certain embodiments, the subject is a fish or reptile.

In certain embodiments, the biological sample, tissue, or cell (e.g., the biological sample, tissue, or cell being contacted with a compound or pharmaceutical composition described herein) is in vitro. In certain embodiments, the biological sample, tissue, or cell is in vivo or ex vivo. In certain embodiments, the cell is a malignant cell or premalignant cell. In certain embodiments, the biological sample is tissue from a tumor (e.g., malignant or benign tumor).

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject or cell. In certain embodiments, the duration between the first dose and last dose of the multiple doses is three months, six months, or one year. In certain embodiments, the duration between the first dose and last dose of the multiple doses is the lifetime of the subject or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is about 70 kg.

A compound or composition, as described herein, can be administered in combination with one or more additional pharmaceutical agents, which are different from the compound of the present disclosure. In certain embodiments, the additional pharmaceutical agents are additional therapeutically active agents, additional prophylactically active agents, or a combination thereof. The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of a kinase (e.g., CDK) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, cancer, inflammatory disease, autoimmune disease, genetic disease, hematological disease, neurological disease, painful condition, psychiatric disorder, or metabolic disorder) or premalignant condition. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include cytotoxic chemotherapeutic agents, epigenetic modifiers, glucocorticoids, immunotherapeutic agents, anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is abiraterone acetate (e.g., ZYTIGA), ABVD, ABVE, ABVE-PC, AC, AC-T, ADE, ado-trastuzumab emtansine (e.g., KADCYLA), afatinib dimaleate (e.g., GILOTRIF), aldesleukin (e.g., PROLEUKIN), alemtuzumab (e.g., CAMPATH), anastrozole (e.g., ARIMIDEX), arsenic trioxide (e.g., TRISENOX), asparaginase *Erwinia chrysanthemi* (e.g., ERWINAZE), axitinib (e.g., INLYTA), azacitidine (e.g., MYLOSAR, VIDAZA), BEACOPP, belinostat (e.g., BELEODAQ), bendamustine hydrochloride (e.g., TREANDA), BEP, bevacizumab (e.g., AVASTIN), bicalutamide (e.g., CASODEX), bleomycin (e.g., BLENOXANE), blinatumomab (e.g., BLINCYTO), bortezomib (e.g., VELCADE), bosutinib (e.g., BOSULIF), brentuximab vedotin (e.g., ADCETRIS), busulfan (e.g., BUSULFEX, MYLERAN), cabazitaxel (e.g., JEVTANA), cabozantinib-s-malate (e.g., COMETRIQ), CAF, capecitabine (e.g., XELODA), CAPOX, carboplatin (e.g., PARAPLAT, PARAPLATIN), carboplatin-taxol, carfilzomib (e.g., KYPROLIS), carmustine (e.g., BECENUM, BICNU, CARMUBRIS), carmustine implant (e.g., GLIADEL WAFER, GLIADEL), ceritinib (e.g., ZYKADIA), cetuximab (e.g., ERBITUX), chlorambucil (e.g., AMBOCHLORIN, AMBOCLORIN, LEUKERAN, LINFOLIZIN), chlorambucil-prednisone, CHOP, cisplatin (e.g., PLATINOL, PLATINOL-AQ), clofarabine (e.g., CLOFAREX, CLOLAR), CMF, COPP, COPP-ABV, crizotinib (e.g., XALKORI), CVP, cyclophosphamide (e.g., CLAFEN, CYTOXAN, NEOSAR), cytarabine (e.g., CYTOSAR-U, TARABINE PFS), dabrafenib (e.g., TAFINLAR), dacarbazine (e.g., DTIC-DOME), dactinomycin (e.g., COSMEGEN), dasatinib (e.g., SPRYCEL), daunorubicin hydrochloride (e.g., CERETBIDINE), decitabine (e.g., DACOGEN), degarelix, denileukin diftitox (e.g., ONTAK), denosumab (e.g., PROLIA, XGEVA), Dinutuximab (e.g., ETNITETXIN), docetaxel (e.g., TAXOTERE), doxorubicin hydrochloride (e.g., ADRIAMYCIN PFS, ADRIAMYCIN RDF), doxorubicin hydrochloride liposome (e.g., DOXIL, DOX-SL, EVACET, LIPODOX), enzalutamide (e.g., XTANDI), epirubicin hydrochloride (e.g., ELLENCE), EPOCH, erlotinib hydrochloride (e.g., TARCEVA), etoposide (e.g., TOPOSAR, VEPESID), etoposide phosphate (e.g., ETOPOPHOS), everolimus (e.g., AFINITOR DISPERZ, AFINITOR), exemestane (e.g., AROMASIN), FEC, fludarabine phosphate (e.g., FLUDARA), fluorouracil (e.g., ADRUCIL, EFUDEX, FLUOROPLEX), FOLFIRI, FOLFIRI-BEVACIZUMAB, FOLFIRI-CETUXIMAB, FOLFIRINOX, FOLFOX, FU-LV, fulvestrant (e.g., FASLODEX), gefitinib (e.g., IRESSA), gemcitabine hydrochloride (e.g., GEMZAR), gemcitabine-cisplatin, gemcitabine-oxaliplatin, goserelin acetate (e.g., ZOLADEX), Hyper-CVAD, ibritumomab tiuxetan (e.g., ZEVALIN), ibrutinib (e.g., IMBRUVICA), ICE, idelalisib (e.g., ZYDELIG), ifosfamide (e.g., CYFOS, IFEX, IFOSFAMIDUM), imatinib mesylate (e.g., GLEEVEC), imiquimod (e.g., ALDARA), ipilimumab (e.g., YERVOY), irinotecan hydrochloride (e.g., CAMPTOSAR), ixabepilone (e.g., IXEMPRA), lanreotide acetate (e.g., SOMATULINE DEPOT), lapatinib ditosylate (e.g., TYKERB), lenalidomide (e.g., REVLIMID), lenvatinib (e.g., LENVIMA), letrozole (e.g., FEMARA), leucovorin calcium (e.g., WELLCOVORIN), leuprolide acetate (e.g., LUPRON DEPOT, LUPRON DEPOT-3 MONTH, LUPRON DEPOT-4 MONTH, LUPRON DEPOT-PED, LUPRON, VIADUR), liposomal cytarabine (e.g., DEPOCYT), lomustine (e.g., CEENU), mechlorethamine hydrochloride (e.g., MUSTARGEN), megestrol acetate (e.g., MEGACE), mercaptopurine (e.g., PURINETHOL, PURIXAN), methotrexate (e.g., ABITREXATE, FOLEX PFS, FOLEX, METHOTREXATE LPF, MEXATE, MEXATE-AQ), mitomycin c (e.g., MITOZYTREX, MUTAMYCIN), mitoxantrone hydrochloride, MOPP, nelarabine (e.g., ARRANON), nilotinib (e.g., TASIGNA), nivolumab (e.g., OPDIVO), obinutuzumab (e.g., GAZYVA), OEPA, ofatumumab (e.g., ARZERRA), OFF, olaparib (e.g., LYNPARZA), omacetaxine mepesuccinate (e.g., SYNRIBO), OPPA, oxaliplatin (e.g., ELOXATIN), paclitaxel (e.g., TAXOL), paclitaxel albumin-stabilized nanoparticle formulation (e.g., ABRAXANE), PAD, palbociclib (e.g., IBRANCE), pamidronate disodium (e.g., AREDIA), panitumumab (e.g., VECTIBIX), panobinostat (e.g., FARYDAK), pazopanib hydrochloride (e.g., VOTRIENT), pegaspargase (e.g., ONCASPAR), peginterferon alfa-2b (e.g., PEG-INTRON), peginterferon alfa-2b (e.g., SYLATRON), pembrolizumab (e.g., KEYTRUDA), pemetrexed disodium (e.g., ALIMTA), pertuzumab (e.g., PERJETA), plerixafor (e.g., MOZOBIL), pomalidomide (e.g., POMALYST), ponatinib hydrochloride (e.g., ICLETSIG), pralatrexate (e.g., FOLOTYN), prednisone, procarbazine hydrochloride (e.g., MATULANE), radium 223 dichloride (e.g., XOFIGO), raloxifene hydrochloride (e.g., EVISTA, KEOXIFENE), ramucirumab (e.g., CYRAMZA), R-CHOP, recombinant HPV bivalent vaccine (e.g., CERVARIX), recombinant human papillomavirus (e.g., HPV) nonavalent vaccine (e.g., GARDASIL 9), recombinant human papillomavirus (e.g., HPV) quadrivalent vaccine (e.g., GARDASIL), recombinant interferon alfa-2b (e.g., INTRON A), regorafenib (e.g., STIVARGA), rituximab (e.g., RITUXAN), romidepsin (e.g., ISTODAX), ruxolitinib phosphate (e.g., JAKAFI), siltuximab (e.g., SYLVANT), sipuleucel-t (e.g., PROVENGE), sorafenib tosylate (e.g., NEXAVAR), STANFORD V, sunitinib malate (e.g., SUTENT), TAC, tamoxifen citrate (e.g., NOLVADEX, NOVALDEX), temozolomide (e.g., METHAZOLASTONE, TEMODAR), temsirolimus (e.g., TORISEL), thalidomide (e.g., SYNOVIR, THALOMID), thiotepa, topotecan hydrochloride (e.g., HYCAMTIN), toremifene (e.g., FARESTON), tositumomab and iodine I 131 tositumomab (e.g., BEXXAR), TPF, trametinib (e.g., MEKINIST), trastuzumab (e.g., HERCEPTIN), VAMP, vandetanib (e.g., CAPRELSA), VEIP, vemurafenib (e.g., ZELBORAF), vinblastine sulfate (e.g., VELBAN, VELSAR), vincristine sulfate (e.g., VINCASAR PFS), vincristine sulfate liposome (e.g., MARQIBO), vinorelbine tartrate (e.g., NAVELBINE), vismodegib (e.g., ERIVEDGE), vorinostat (e.g., ZOLINZA), XELIRI, XELOX, ziv-aflibercept (e.g., ZALTRAP), or zoledronic acid (e.g., ZOMETA). In certain embodiments, the additional pharmaceutical agent is ENMD-2076, PCI-32765, AC220, dovitinib lactate (e.g., TKI258, CHIR-258), BIBW 2992 (e.g., TOVOK™), SGX523, PF-04217903, PF-02341066, PF-299804, BMS-777607, ABT-869, MP470, BIBF 1120 (e.g., VARGATEF®), AP24534, JNJ-26483327, MGCD265, DCC-2036, BMS-690154, CEP-11981, tivozanib (e.g., AV-951), OSI-930, MM-121, XL-184, XL-647, and/or XL228), proteasome inhibitors (e.g., bortezomib (e.g., Velcade)), mTOR inhibitors (e.g., rapamycin, temsirolimus (e.g., CCI-779), everolimus (e.g., RAD-001), ridaforolimus, AP23573 (e.g., Ariad), AZD8055, BEZ235, BGT226, XL765, PF-4691502, GDC0980, SF1126, and OSI-027), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a cytotoxic chemotherapy (e.g., cytotoxic chemotherapeutic agent (e.g., gemcitabine, cytarabine, daunorubicin, doxorubicin, vincristine, 1-asparaginase, cyclophosphamide, or etoposide)). In certain embodiments, the additional pharmaceutical agent is an epigenetic modifier, such as azacitidine or romidepsin. In certain embodiments, the additional pharmaceutical agent is ruxolitinib, BBT594, CHZ868, CYT387, or BMS911543. In certain embodiments, the additional pharmaceutical agent is an inhibitor of a tyrosine kinase. In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino) cyclohexyl)amino)-[2,4'-bipyridin]-6-yl)amino)methyl) tetrahydro-2H-pyran-4-carbonitrile, JIB04, or cisplatin. In certain embodiments, the additional pharmaceutical agent is a binder or inhibitor of a kinase (e.g., CDK). In certain embodiments, the additional pharmaceutical agent is an antibody or a fragment thereof (e.g., monoclonal antibody). In certain embodiments, the additional pharmaceutical agent is a tyrosine kinase inhibitor. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-tram retinoic acids, and other agents that promote differentiation. In certain embodiments, the additional pharmaceutical agent is a glucocorticoid (e.g., cortisol, cortisone, prednisone, methylprednisolone, dexamethasone, betamethasone, triamcinolone, fludrocortisone acetate, or deoxycorticosterone acetate). In certain embodiments, the additional therapy is an immunotherapy (e.g., an immunotherapeutic monoclonal antibody). In certain embodiments, the additional pharmaceutical agent is an immunomodulator. In certain embodiments, the additional pharmaceutical agent is an immune checkpoint inhibitor. In certain embodiments, the additional pharmaceutical agent is a programmed cell death 1 protein (PD-1) inhibitor. In certain embodiments, the additional pharmaceutical agent is a programmed cell death 1 protein ligand 1 (PD-L1) inhibitor. In certain embodiments, the additional pharmaceutical agent is a cytotoxic T-lymphocyte-associated protein 4 (CTLA-4) inhibitor. In certain embodiments, the additional pharmaceutical agent is a T-cell immunoglobulin domain and mucin domain 3 (TIM3) inhibitor, lymphocyte activation gene-3 (LAG3) inhibitor, V-set domain-containing T-cell activation inhibitor 1 (VTCN1 or B7-H4) inhibitor, cluster of differentiation 276 (CD276 or B7-H3) inhibitor, B and T lymphocyte attenuator (BTLA) inhibitor, galectin-9 (GAL9) inhibitor, checkpoint kinase 1 (Chk1) inhibitor, adenosine A2A receptor (A2AR) inhibitor, indoleamine 2,3-dioxygenase (IDO) inhibitor, killer-cell immunoglobulin-like receptor (KIR) inhibitor, or V-domain Ig suppressor of T cell activation (VISTA) inhibitor. In certain embodiments, the PD-1 inhibitor is nivolumab, pidilizumab, pembrolizumab, MEDI-0680, REGN2810, or AMP-224. In certain embodiments, the PD-L1 inhibitor is atezolizumab, durvalumab, BMS-936559, avelumab, or CA-170. In certain embodiments, the CTLA-4 inhibitor is ipilimumab or tremelimumab. In certain embodiments, the additional pharmaceutical agent is an aromatase inhibitor. In certain embodiments, the additional pharmaceutical agent is an PI3K inhibitor. In certain embodiments, the additional pharmaceutical agent is an mTOR inhibitor. In certain embodiments, the additional pharmaceutical agent is an endocrine therapy. In certain embodiments, the compounds or pharmaceutical compositions are administered in combination with surgery, radiation therapy, and/or transplantation (e.g., stem cell transplantation, bone marrow transplantation). In certain embodiments, the compound or pharmaceutical composition disclosed herein is administered in combination with radiation therapy.

Also encompassed by the present disclosure are kits (e.g., pharmaceutical packs). In certain embodiments, the kit comprises a compound or pharmaceutical composition described herein, and instructions for using the compound or pharmaceutical composition. In certain embodiments, the kit comprises a first container, wherein the first container includes the compound or pharmaceutical composition. In some embodiments, the kit further comprises a second container. In certain embodiments, the second container includes an excipient (e.g., an excipient for dilution or suspension of the compound or pharmaceutical composition). In certain embodiments, the second container includes an additional pharmaceutical agent. In some embodiments, the kit further comprises a third container. In certain embodiments, the third container includes an additional pharmaceutical agent. In some embodiments, the compound or pharmaceutical composition included in the first container and the excipient or additional pharmaceutical agent included in the second container are combined to form one unit dosage form. In some embodiments, the compound or pharmaceutical composition included in the first container, the excipient included in the second container, and the additional pharmaceutical agent included in the third container are combined to form one unit dosage form. In certain embodiments, each of the first, second, and third containers is independently a vial, ampule, bottle, syringe, dispenser package, tube, or inhaler.

In certain embodiments, the instructions are for administering the compound or pharmaceutical composition to a subject (e.g., a subject in need of treatment or prevention of a disease described herein). In certain embodiments, the instructions are for contacting a biological sample, tissue, or cell with the compound or pharmaceutical composition. In certain embodiments, the instructions comprise information required by a regulatory agency, such as the U.S. Food and Drug Administration (FDA) or the European Agency for the Evaluation of Medicinal Products (EMA). In certain embodiments, the instructions comprise prescribing information.

Methods of Use and Uses

The present disclosure also provides methods of using the compounds and pharmaceutical compositions of the present disclosure. In another aspect, the present disclosure provides methods of inhibiting the activity of a kinase in a subject, the methods comprising administering to the subject an effective amount of a compound or pharmaceutical composition of the present disclosure.

In another aspect, the present disclosure provides methods of inhibiting the activity of a kinase in a biological sample or tissue, the methods comprising contacting the biological sample or tissue with an effective amount of a compound or pharmaceutical composition of the present disclosure.

In another aspect, the present disclosure provides methods of inhibiting the activity of a kinase in a cell, the methods comprising contacting the cell with an effective amount of a compound or pharmaceutical composition of the present disclosure.

In another aspect, the present disclosure provides methods of down-regulating the transcription of MYC or MCL-1 in a subject, the methods comprising administering to the subject an effective amount of a compound or pharmaceutical composition of the present disclosure.

In another aspect, the present disclosure provides methods of down-regulating the transcription of MYC or MCL-1 in a biological sample or tissue, the methods comprising contacting the biological sample or tissue with an effective amount of a compound or pharmaceutical composition of the present disclosure.

In another aspect, the present disclosure provides methods of down-regulating the transcription of MYC or MCL-1 in a cell, the methods comprising contacting the cell with an effective amount of a compound or pharmaceutical composition of the present disclosure.

Kinases are implicated in a range of diseases. In certain embodiments, the kinase is a CDK (e.g., CDK7). The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as CDKs and a diverse set of their cognate protein partners termed cyclins. CDKs are CDC2 (also known as CDK1) homologous serine-threonine kinase proteins that may be able to utilize ATP as a substrate in the phosphorylation of diverse polypeptides in a sequence-dependent context. Cyclins are a family of proteins characterized by a homology region, containing approximately 100 amino acids, termed the “cyclin box” which is used in binding to, and defining selectivity for, specific CDK partner proteins.

Modulation of the expression levels, degradation rates, protein levels, and activity levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the prerequisite biochemical criteria at a given cell cycle checkpoint, i.e., failure to form a required CDK/cyclin complex, can lead to cell cycle arrest and/or cellular apoptosis. Aberrant cellular proliferation can often be attributed to loss of correct cell cycle control. Inhibition of CDK enzymatic activity therefore provides a means by which abnormally dividing cells can have their division arrested and/or be killed. The diversity of CDKs, and CDK complexes, and their critical roles in mediating the cell cycle, provides a broad spectrum of potential therapeutic targets selected on the basis of a defined biochemical rationale.

CDK7, a member of the CDK family, was originally isolated as the catalytic subunit of the trimeric CDK-activating kinase (CAK) complex. This complex, consisting of CDK7, cyclin H, and MAT1, is responsible for activation of the mitotic promoting factor in vitro. The discovery that CDK7 was also a component of the basal transcription repair factor IIH (TFIIH) implicated a dual role for CDK7 in transcription as part of TFIIH and in the control of the cell cycle as the trimeric CAK complex. TFIIH is a multi-subunit protein complex identified as a factor required for RNA polymerase II (RNAP II)-catalyzed transcription, and subsequently this complex was found to play a key role in nucleotide excision repair. CDK7 is a component of at least three complexes, i.e., the trimeric CAK complex, the quaternary complex with the XPD (or ERCC2, a protein involved in transcription-coupled nucleotide excision repair), and the nine-subunit TFIIH complex. The two functions of CDK7 in CAK and CTD phosphorylation support critical facets of cellular proliferation, cell cycling, and transcription. Overexpression of CDK7 may inhibit apoptosis, promote transcription and cell proliferation, and/or disrupt DNA repair, and therefore, cause proliferative diseases.

A disease described herein may be associated with aberrant activity of a kinase (e.g., CDK (e.g., CDK7)). Aberrant activity of the kinase may be an elevated and/or an aberrant activity. Deregulation of cell cycle progression is a characteristic of a proliferative disease. Certain proliferative diseases have abnormalities in kinase activity, some of which are through elevated and/or aberrant kinase activation. Inhibition of the catalytic activity of CDK would be expected to inhibit cell cycle progression by blocking the phosphorylation of cell cycle CDK, and would additionally inhibit transcription of effectors of cell division. In certain embodiments, the kinase is not overexpressed, and the activity of the kinase is elevated and/or aberrant. In certain other embodiments, the kinase is overexpressed, and the activity of the kinase is elevated and/or aberrant. The compounds and pharmaceutical compositions of the present disclosure may inhibit the activity of CDK7 and be useful in treating and/or preventing proliferative diseases.

A disease described herein may also be associated with inhibition of apoptosis of a cell in a subject. Apoptosis is the process of programmed cell death. Inhibition of apoptosis may result in uncontrolled cell proliferation and, therefore, may cause proliferative diseases. The cell cycle CDKs (e.g., CDK1, 2, 4, and 6) are activated by phosphorylation by CDK7/cyclin H (also called CAK). Inhibition of CDK7 may therefore result in cell-cycle arrest at multiple points in the cell cycle due to failure to activate the cell cycle CDKs. CDK7 activates transcription by phosphorylating the CTD of RNAP II. Inhibition of CTD phosphorylation has been shown to inhibit transcription and reduce expression of short lived proteins, including those involved in apoptosis regulation. It is appreciated in the art that stalling of RNA polymerase may activate p53 (also known as protein 53 or tumor protein 53, a tumor suppressor protein that is encoded in humans by the TP53 gene), leading to apoptosis. Thus, inhibition of the activity of CDK7 are expected to cause cytotoxicity by inducing apoptosis. The compounds and pharmaceutical compositions of the present disclosure may induce apoptosis, and therefore, be useful in treating and/or preventing diseases (e.g., proliferative diseases, cystic fibrosis).

In another aspect, the present disclosure provides methods of treating a disease in a subject in need thereof, the method comprising administering to the subject in need thereof an effective amount of a compound or pharmaceutical composition of the present disclosure. In certain embodiments, the effective amount is effective in treating the disease. In certain embodiments, the effective amount is effective in treating the disease and inhibiting the activity of a kinase. In certain embodiments, the effective amount is effective in treating the disease and down-regulating the transcription of MYC or MCL-1.

In another aspect, the present disclosure provides methods of preventing a disease in a subject in need thereof, the method comprising administering to the subject in need thereof an effective amount of a compound or pharmaceutical composition of the present disclosure. In certain embodiments, the effective amount is effective in preventing the disease. In certain embodiments, the effective amount is effective in preventing the disease and inhibiting the activity of a kinase. In certain embodiments, the effective amount is effective in preventing the disease and down-regulating the transcription of MYC or MCL-1.

In another aspect, the present disclosure provides methods of inhibiting the growth of a cell, the method comprising contacting the cell with an effective amount of a compound or pharmaceutical composition of the present disclosure.

In another aspect, the present disclosure provides methods of inducing apoptosis of a cell, the method comprising contacting the cell with an effective amount of a compound or pharmaceutical composition of the present disclosure.

In certain embodiments, the subject is a mammal. In certain embodiments, the subject is a human. In certain embodiments, the subject is a non-human mammal.

In certain embodiments, the biological sample or tissue is bone marrow, lymph node, spleen, or blood. In certain embodiments, the biological sample or tissue is in vitro. In certain embodiments, the biological sample or tissue is ex vivo.

In certain embodiments, the cell is in vitro. In certain embodiments, the cell is ex vivo. In certain embodiments, the cell is in vivo. In certain embodiments, the cell is in a subject. In certain embodiments, the cell is in a biological sample or tissue. In certain embodiments, the cell is a malignant cell. In certain embodiments, the cell is a premalignant cell.

In certain embodiments, the disease (e.g., disease being treated or prevented using the compounds or pharmaceutical compositions of the present disclosure) is cancer. In certain embodiments, the disease is associated with aberrant activity (e.g., increased activity, undesired activity) of a kinase. In certain embodiments, the disease is associated with aberrant activity of a CDK (e.g., CDK7). In certain embodiments, the disease is associated with aberrant activity (e.g., overexpression of a kinase. In certain embodiments, the disease is associated with the overexpression of a CDK (e.g., CDK7). In certain embodiments, the disease is a proliferative disease. In certain embodiments, the disease is cancer. In certain embodiments, the disease is an adenocarcinoma, blastoma, carcinoma, hematological malignancy, myeloma, or sarcoma. In certain embodiments, the disease is a premalignant condition. In certain embodiments, the disease is a hematological malignancy. In certain embodiments, the disease is a hematological malignancy. In certain embodiments, the disease is leukemia. In certain embodiments, the disease is chronic lymphocytic leukemia (CLL). In certain embodiments, the disease is acute lymphoblastic leukemia (ALL). In certain embodiments, the disease is T-cell acute lymphoblastic leukemia (T-ALL). In certain embodiments, the disease is chronic myelogenous leukemia (CML). In certain embodiments, the disease is acute myelogenous leukemia (AML). In certain embodiments, the disease is acute monocytic leukemia (AMoL). In certain embodiments, the disease is lymphoma. In some embodiments, the disease is Burkitt's lymphoma. In certain embodiments, the disease is a Hodgkin's lymphoma. In certain embodiments, the disease is a non-Hodgkin's lymphoma. In certain embodiments, the disease is multiple myeloma. In certain embodiments, the disease is melanoma. In certain embodiments, the disease is adrenocortical cancer. In certain embodiments, the disease is colorectal cancer. In certain embodiments, the disease is breast cancer. In certain embodiments, the disease is triple-negative breast cancer (TNBC). In certain embodiments, the disease is esophageal cancer. In certain embodiments, the disease is gastric cancer. In certain embodiments, the disease is liver cancer. In certain embodiments, the disease is ovarian cancer. In certain embodiments, the disease is pancreatic cancer. In certain embodiments, the disease is prostate cancer. In certain embodiments, the disease is testicular cancer. In certain embodiments, the disease is a bone cancer. In certain embodiments, the disease is osteosarcoma. In certain embodiments, the disease is Ewing's sarcoma. In some embodiments, the disease is a brain cancer. In some embodiments, the disease is neuroblastoma. In some embodiments, the disease is a lung cancer. In some embodiments, the disease is small cell lung cancer (SCLC). In some embodiments, the disease is non-small cell lung cancer. In some embodiments, the disease is a benign neoplasm. In some embodiments, the disease is pathological angiogenesis. In certain embodiments, the disease is an inflammatory disease. In certain embodiments, the inflammatory disease is rheumatoid arthritis. In some embodiments, the disease is an autoinflammatory disease. In some embodiments, the disease is an autoimmune disease. In certain embodiments, the disease is cystic fibrosis.

In certain embodiments, the method further comprises administering to the subject an additional therapy. In certain embodiments, the additional therapy is an additional pharmaceutical agent. In certain embodiments, the additional therapy is an aromatase inhibitor, HDAC inhibitor, phosphatidylinositol-4,5-bisphosphate 3-kinase (PI3K) inhibitor, mammalian target of rapamycin (mTOR) inhibitor, endocrine therapy, cytotoxic chemotherapy, epigenetic modifier, glucocorticoid, immunotherapy, or radiation therapy. In certain embodiments, the additional therapy is a cytotoxic chemotherapy. In certain embodiments, the additional therapy is an immunotherapy. In certain embodiments, the additional therapy is radiation therapy.

The compounds or pharmaceutical compositions of the present disclosure and the additional therapy may show synergy in the methods and uses of the present disclosure.

In another aspect, provided herein are uses of the compounds or pharmaceutical compositions of the present disclosure in the manufacture of a medicament for use in a method (e.g., method of treating a disease in a subject in need thereof; method of preventing a disease in a subject in need thereof; method of inhibiting the activity of a kinase in a subject, biological sample, tissue, or cell; method of inhibiting the growth of a cell; method of inducing apoptosis of a cell; method of down-regulating the transcription of MYC or MCL-1 in a subject, biological sample, tissue, or cell) of the present disclosure.

In another aspect, provided herein are uses of the compounds or pharmaceutical compositions of the present disclosure in a method (e.g., method of treating a disease in a subject in need thereof; method of preventing a disease in a subject in need thereof; method of inhibiting the activity of a kinase in a subject, biological sample, tissue, or cell; method of inhibiting the growth of a cell; method of inducing apoptosis of a cell; method of down-regulating the transcription of MYC or MCL-1 in a subject, biological sample, tissue, or cell) of the present disclosure.

In another aspect, provided herein are the compounds or pharmaceutical compositions of the present disclosure for use in a method (e.g., method of treating a disease in a subject in need thereof; method of preventing a disease in a subject in need thereof; method of inhibiting the activity of a kinase in a subject, biological sample, tissue, or cell; method of inhibiting the growth of a cell; method of inducing apoptosis of a cell; method of down-regulating the transcription of MYC or MCL-1 in a subject, biological sample, tissue, or cell) of the present disclosure.

EXAMPLES

In order that the disclosure described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Synthesis of the Compounds

The compounds provided herein can be prepared from readily available starting materials using the following general methods and procedures. Reactions were monitored by thin layer chromatography (TLC) with 0.25 mm E. Merck pre-coated silica gel plates (60 $F_{254}$) and Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ $C_{18}$ column (4.6×50 mm, 5 μm particle size):solvent gradient=95% A at 0 min, 0% A at 5 min; solvent A=0.5% TFA in water; solvent B=methanol; flow rate=1.5 mL/min. Purification of reaction products was carried out by flash chromatography using CombiFlash® Rf with Teledyne Isco RediSep® Rf High Performance Gold or Silicycle SiliaSep™ High Performance columns (4 g, 12 g, 24 g, 40 g, 80 g, or 120 g) or by Waters preparative HPLC system with a $C_{18}$ column: solvent gradient=100% A at 0 min, 0% A at 15 min; solvent A=0.5% TFA in water; solvent B=methanol; flow rate=: 20 mL/min. The purity of all compounds was over 95% and was analyzed with Waters LCMS system. $^{1}$H NMR and $^{13}$C NMR spectra were obtained using a Varian Inova-600 or 400 MHz spectrometer. Chemical shifts are reported relative to chloroform (S=7.24) for $^{1}$H NMR or dimethyl sulfoxide (S=2.50) for $^{1}$H NMR and dimethyl sulfoxide (S=39.51) for $^{13}$C NMR. Data are reported as (br=broad, s=singlet, d=doublet, t=triplet, q=quartet, m=multiplet).

Example 1.1. (S)—N-(2-(dimethylamino)-1-(tetrahydro-2H-pyran-4-yl)ethyl)-6,6-dimethyl-3-((2-methylthieno[2,3-d]pyrimidin-4-yl)amino)-4,6-dihydropyrrolo[3,4-c]pyrazole-5(1H)-carboxamide (Compound 200)

The synthesis of Compound 200 follows Scheme 1. The synthesis of Compound 201 and Compound 208 follow a similar method.

Scheme 1.

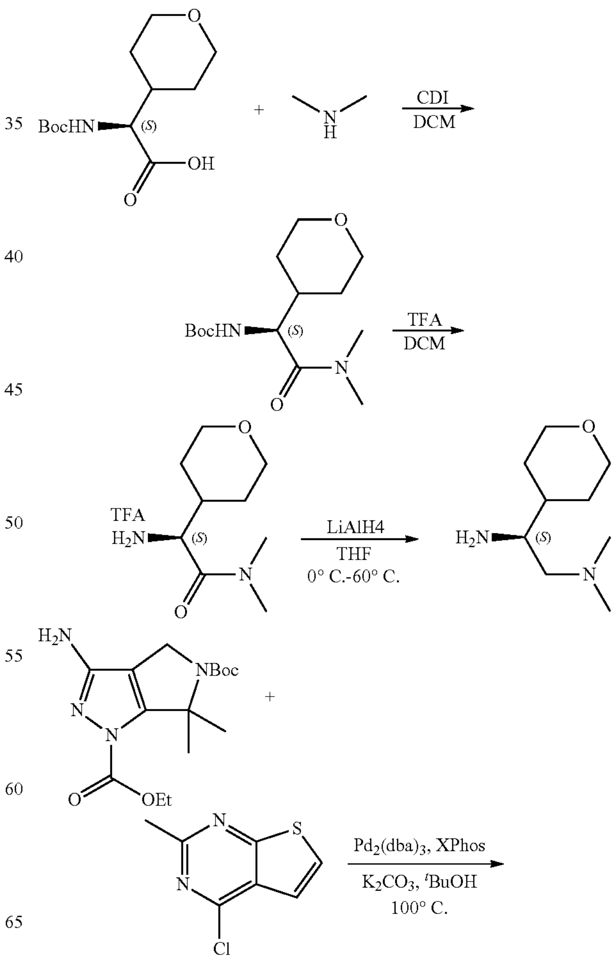

-continued

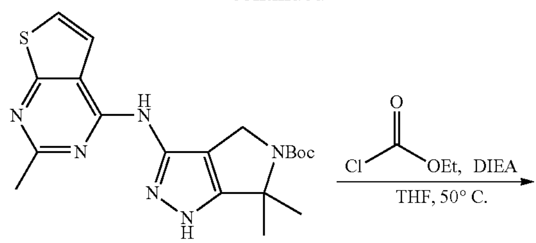

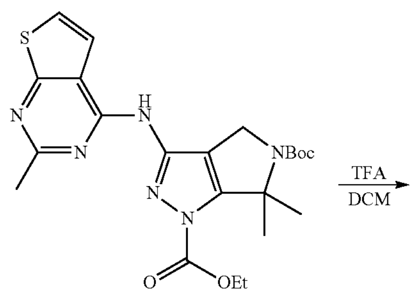

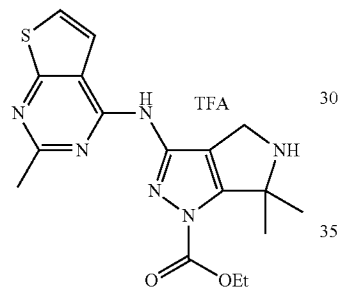

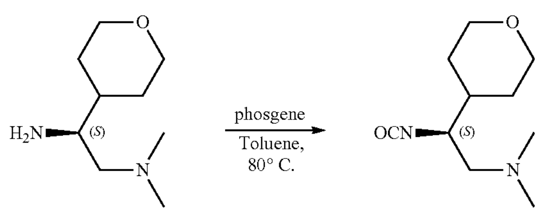

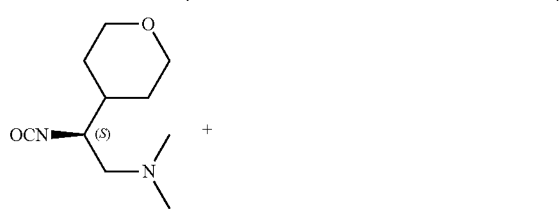

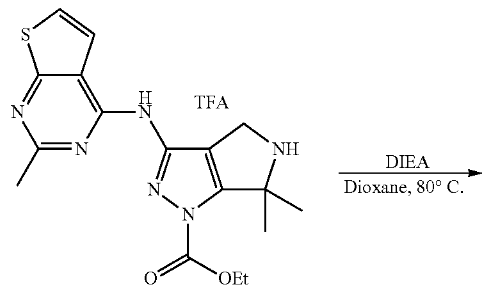

-continued

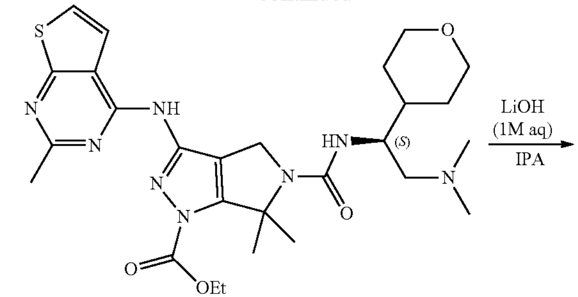

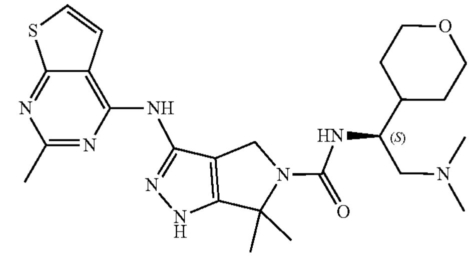

tert-butyl (S)-(2-(dimethylamino)-2-oxo-1-(tetrahydro-2H-pyran-4-yl)ethyl)carbamate

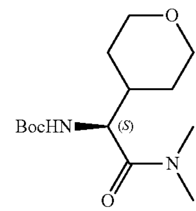

To a solution of (S)-2-((tert-butoxycarbonyl)amino)-2-(tetrahydro-2H-pyran-4-yl)acetic acid (3 g, 11.6 mmol) in DCM (50 mL) was added CDI (1.9 g, 11.6 mmol), and then the mixture was stirred at room temperature for 1 h, then dimethylamine (2 M in THF, 11.6 mL, 23.2 mmol) was added. The mixture was stirred at room temperature overnight, concentrated under reduced pressure, and purified by silica gel column chromatography (MeOH/DCM=0-5%) to give tert-butyl (S)-(2-(dimethylamino)-2-oxo-1-(tetrahydro-2H-pyran-4-yl)ethyl)carbamate as white solid. LCMS: 287 $[M+H]^+$.

(S)-2-amino-N,N-dimethyl-2-(tetrahydro-2H-pyran-4-yl)acetamide

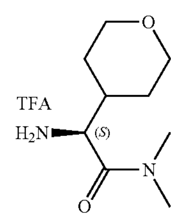

Tert-butyl (5)-(2-(dimethylamino)-2-oxo-1-(tetrahydro-2H-pyran-4-yl)ethyl)carbamate was dissolved in DCM (30 mL) and stirred at 0° C. for 5 min, and then TFA (10 mL) was added. The mixture was stirred at room temperature for 1 h and then concentrated under reduced pressure to give (S)-2-amino-N,N-dimethyl-2-(tetrahydro-2H-pyran-4-yl) acetamide, which was used to next step without any purification. LCMS: 187 [M+H]$^+$.

(S)—N$^1$,N$^1$-dimethyl-2-(tetrahydro-2H-pyran-4-yl) ethane-1,2-diamine

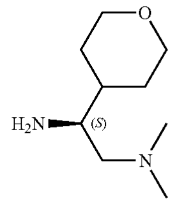

A solution of (S)-2-amino-N,N-dimethyl-2-(tetrahydro-2H-pyran-4-yl)acetamide (11.6 mmol) in dry THF (50 mL) was stirred at 0° C. for 10 min, and then $LiAlH_4$ (2.5 M in THF, 9.28 mL, 23.2 mmol) was added carefully under $N_2$ atmosphere. After addition, the mixture was stirred at 60° C. for 3 h and cooled down to room temperature. Cold water (882 μL) was added dropwise to the mixture at 0° C., and then NaOH solution (15% aq., 882 μL) was added carefully, then 3×882 μL water was added again. The mixture was warmed up to room temperature, and ethyl ether was added. The mixture was stirred for 10 min and filtered. The filtrate was concentrated under reduced pressure and purified by silica gel column chromatography (1.75 N $NH_3$ in MeOH/DCM=0-20%) to give (S)—N$^1$,N$^1$-dimethyl-2-(tetrahydro-2H-pyran-4-yl)ethane-1,2-diamine (1.6 g, 80% for 3 steps) as yellow liquid. LCMS: 173 [M+H]$^+$.

tert-butyl 6,6-dimethyl-3-((2-methylthieno[2,3-d] pyrimidin-4-yl)amino)-4,6-dihydropyrrolo[3,4-c] pyrazole-5(1H)-carboxylate

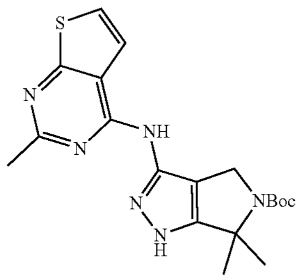

To a solution of 4-chloro-2-methylthieno[2,3-d]pyrimidine (221 mg, 1.2 mmol) and 5-(tert-butyl) 1-ethyl 3-amino-6,6-dimethyl-4,6-dihydropyrrolo[3,4-c]pyrazole-1,5-dicarboxylate (390 mg, 1.2 mmol) in $^t$BuOH (6 mL) were added $Pd_2(dba)_3$ (55 mg, 0.06 mmol), XPhos (57 mg, 0.12 mmol), and $K_2CO_3$ (497 mg, 3.6 mmol). The mixture was stirred at 100° C. for 4 h under $N_2$ protection, cooled down to room temperature and then filtered. The filtrate was concentrated under reduced pressure and then purified by silica gel column chromatography (EA/hexane=0-80%) to give tert-butyl 6,6-dimethyl-3-((2-methylthieno[2,3-d]pyrimidin-4-yl)amino)-4,6-dihydropyrrolo[3,4-c]pyrazole-5(1H)-carboxylate (445 mg, 92%). LCMS: 401 [M+H]$^+$.

Ethyl 6,6-dimethyl-3-((2-methylthieno[2,3-d]pyrimidin-4-yl)amino)-5,6-dihydropyrrolo[3,4-c]pyrazole-1 (4H)-carboxylate

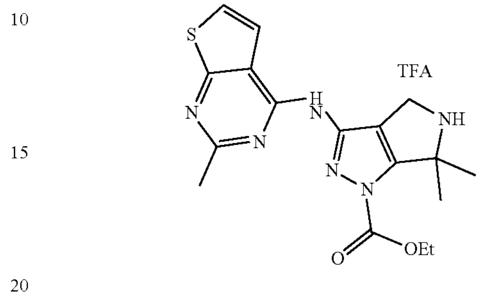

To a solution of ten-butyl 6,6-dimethyl-3-((2-methylthieno[2,3-d]pyrimidin-4-yl)amino)-4,6-dihydropyrrolo[3,4-c]pyrazole-5(1H)-carboxylate (445 mg, 1.1 mmol) and DIEA (363 μL, 2.2 mmol) in THF (10 mL) was added ethyl chloroformate (127 μL, 1.3 mmol) at 0° C. The mixture was stirred at 50° C. for 1 h, and then concentrated under reduced pressure, extracted with EA, and washed with water twice. The organic layer was then concentrated under reduced pressure. The residue was dissolved in TFA/DCM (v/v=1/3, 10 mL). The resulting mixture was stirred at room temperature for 1 h, concentrated under reduced pressure, and then purified by silica gel column chromatography (1.75 N $NH_3$ in MeOH/DCM=0-10%) to give ethyl 6,6-dimethyl-3-((2-methylthieno[2,3-d]pyrimidin-4-yl)amino)-5,6-dihydropyrrolo[3,4-c]pyrazole-1(4H)-carboxylate (202 mg, 45%) as TFA salt. FCMS: 373 [M+H]$^+$.

(S)—N-(2-(dimethylamino)-1-(tetrahydro-2H-pyran-4-yl)ethyl)-6,6-dimethyl-3-((2-methylthieno[2,3-d] pyrimidin-4-yl)amino)-4,6-dihydropyrrolo[3,4-c] pyrazole-5(1H)-carboxamide (Compound 200)

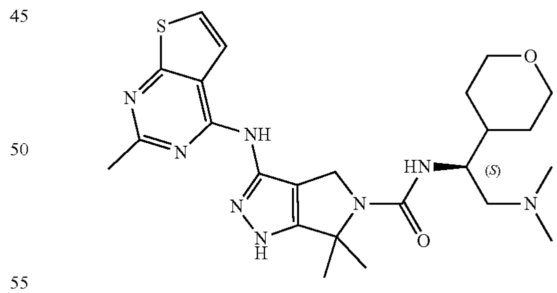

To a solution of (S)—N$^1$,N$^1$-dimethyl-2-(tetrahydro-2H-pyran-4-yl)ethane-1,2-diamine (45 mg, 0.26 mmol) in dry toluene (2 mL) was added phosgene (15% w.t. toluene, 0.2 mL). The mixture was stirred at 80° C. for 2 h and then concentrated under reduced pressure. The residue was dissolved in dioxane (3 mL), and then ethyl 6,6-dimethyl-3-((2-methylthieno[2,3-d]pyrimidin-4-yl)amino)-5,6-dihydropyrrolo[3,4-c]pyrazole-1(4H)-carboxylate (80 mg, 0.16 mmol) and DIEA (129 μL, 0.78 mmol) were added. The mixture was stirred at 80° C. for another 2 h. The mixture was concentrated under reduced pressure and then purified by silica gel column chromatography (1.75 N $NH_3$ in MeOH/DCM=0-15%) to give an intermediate (28 mg, 22%).

The intermediate was then dissolved in the mixture of isopropanol (IPA, 1 mL) and LiOH (1 M aq., 1 mL). The mixture was stirred at room temperature for 10 min, concentrated under reduced pressure, and purified by prep-HPFC (MeOH/water, 0.035% TFA) to give a TFA salt of Compound 200 (27.6 mg, 90%). FCMS: 499 $[M+H]^+$.

$^1$H NMR (500 MHz, DMSO-$d_6$) δ 10.57 (s, 1H), 9.11 (s, 1H), 7.86 (d, J=6.0 Hz, 1H), 7.61 (d, J=5.9 Hz, 1H), 5.88 (d, J=9.3 Hz, 1H), 4.58 (q, J=11.6 Hz, 2H), 4.01-3.95 (m, 1H), 3.90-3.81 (m, 2H), 3.24 (ddd, J=15.3, 8.5, 4.0 Hz, 4H), 2.83 (d, J=4.8 Hz, 3H), 2.79 (d, J=4.8 Hz, 3H), 2.61 (s, 3H), 1.70 (d, J=1.9 Hz, 6H), 1.65 (dt, J=11.0, 3.7 Hz, 1H), 1.56 (d, J=13.0 Hz, 2H), 1.27 (qt, J=12.2, 4.7 Hz, 2H).

Example 1.2. (S)—N-(2-(dimethylamino)-1-(tetrahydro-2H-pyran-4-yl)ethyl)-6,6-dimethyl-3-((2-methylthieno[3,2-d]pyrimidin-4-yl)amino)-4,6-dihydropyrrolo[3,4-c]pyrazole-5(1H)-carboxamide (Compound 201)

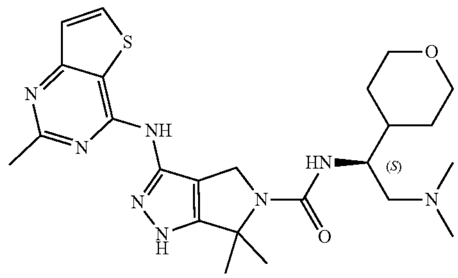

Compound 201 (42 mg, 22%) was obtained according to the synthetic route of Compound 200, except that 4-chloro-2-methylthieno[2,3-d]pyrimidine was changed to 4-chloro-2-methylthieno[3,2-d]pyrimidine. LCMS: 499 $[M+H]^+$.

$^1$H NMR (500 MHz, DMSO-$d_6$) δ 11.65 (s, 1H), 9.18 (s, 1H), 8.45 (d, J=5.5 Hz, 1H), 7.52 (d, J=5.4 Hz, 1H), 5.97 (d, J=9.3 Hz, 1H), 4.53 (d, J=7.3 Hz, 2H), 3.97 (s, 1H), 3.87 (dq, J=12.2, 4.5 Hz, 2H), 3.29-3.19 (m, 4H), 2.82 (d, J=4.8 Hz, 3H), 2.80 (d, J=4.8 Hz, 3H), 2.72 (s, 3H), 1.71 (d, J=3.1 Hz, 6H), 1.66 (dt, J=7.6, 3.9 Hz, 1H), 1.55 (d, J=13.1 Hz, 2H), 1.26 (dtd, J=17.8, 12.2, 6.1 Hz, 2H).

Example 1.3. (S)—N-(2-(dimethylamino)-1-(tetrahydro-2H-pyran-4-yl)ethyl)-6,6-dimethyl-3-((2-(trifluoromethyl)pyrimidin-4-yl)amino)-4,6-dihydropyrrolo[3,4-c]pyrazole-5(1H)-carboxamide (Compound 208)

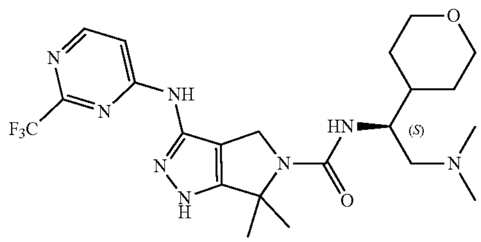

Compound 208 (43 mg, 20%) was obtained according to the synthetic route of Compound 200, except that 4-chloro-2-methylthieno[2,3-d]pyrimidine was changed to 4-chloro-2-(trifluoromethyl)pyrimidine. LCMS: 497 $[M+H]^+$. $^1$H NMR (500 MHz, DMSO-$d_6$) δ 12.53 (s, 1H), 10.57 (s, 1H), 8.42 (s, 1H), 7.01 (s, 1H), 4.49 (s, 2H), 3.94-3.73 (m, 4H), 3.24 (tdd, J=11.7, 4.8, 2.1 Hz, 3H), 2.36 (s, 6H), 1.66 (d, J=3.7 Hz, 7H), 1.54-1.44 (m, 2H), 1.28 (qdd, J=12.1, 7.1, 4.5 Hz, 2H).

Example 1.4. (S)-3-((6-acrylamidoisoquinolin-1-yl)amino)-N-(2-(dimethylamino)-1-(tetrahydro-2H-pyran-4-yl)ethyl)-6,6-dimethyl-4,6-dihydropyrrolo[3,4-c]pyrazole-5(1H)-carboxamide (Compound 202)

The synthesis of Compound 202 follows Scheme 2. The synthesis of Compound 203, Compound 204, Compound 206, and Compound 209 follow a similar method.

Scheme 2.

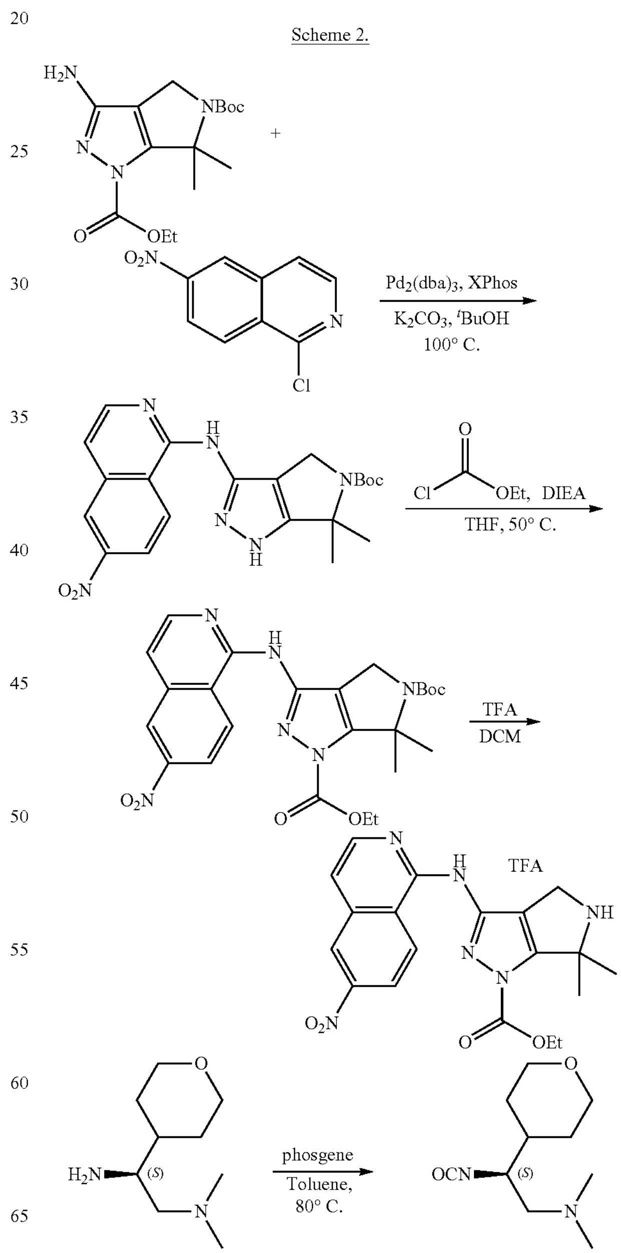

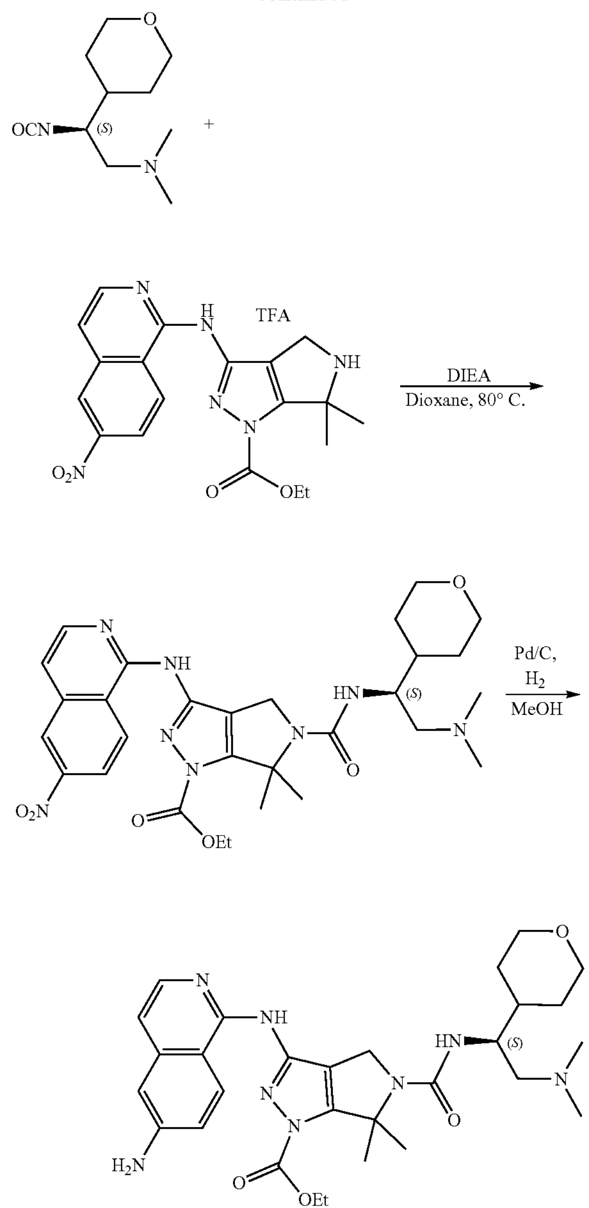

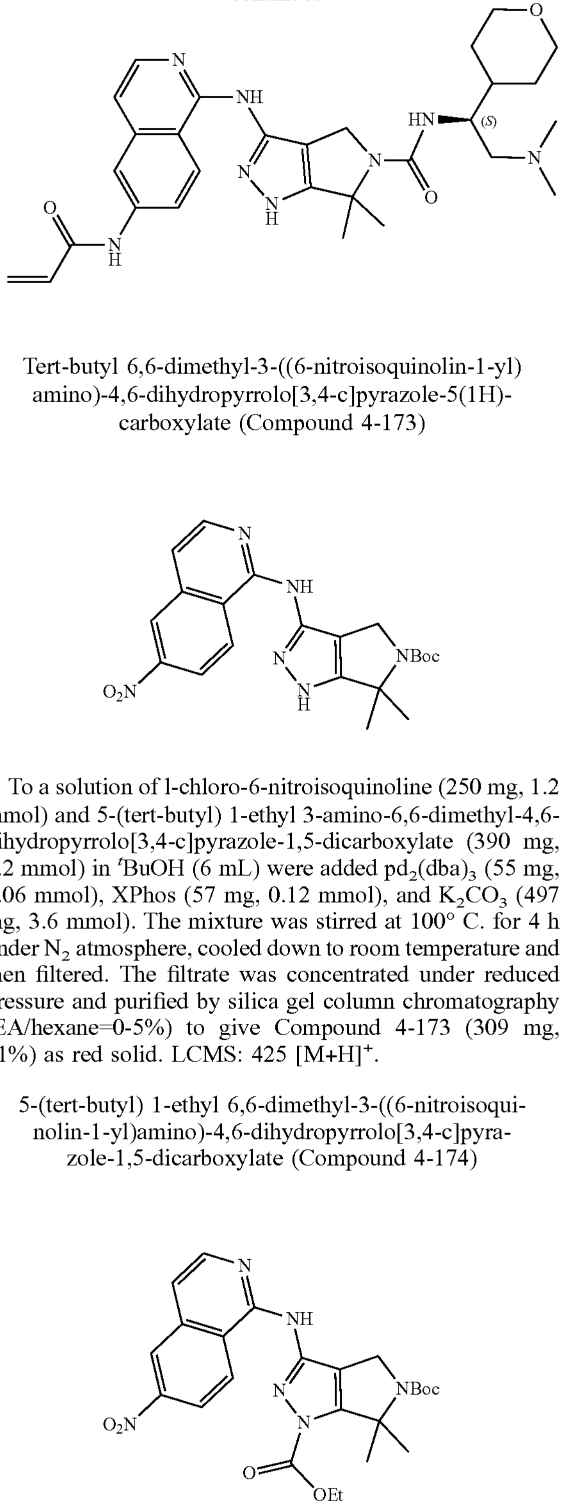

Tert-butyl 6,6-dimethyl-3-((6-nitroisoquinolin-1-yl) amino)-4,6-dihydropyrrolo[3,4-c]pyrazole-5(1H)-carboxylate (Compound 4-173)

To a solution of l-chloro-6-nitroisoquinoline (250 mg, 1.2 mmol) and 5-(tert-butyl) 1-ethyl 3-amino-6,6-dimethyl-4,6-dihydropyrrolo[3,4-c]pyrazole-1,5-dicarboxylate (390 mg, 1.2 mmol) in $^t$BuOH (6 mL) were added $pd_2(dba)_3$ (55 mg, 0.06 mmol), XPhos (57 mg, 0.12 mmol), and $K_2CO_3$ (497 mg, 3.6 mmol). The mixture was stirred at 100° C. for 4 h under $N_2$ atmosphere, cooled down to room temperature and then filtered. The filtrate was concentrated under reduced pressure and purified by silica gel column chromatography (EA/hexane=0-5%) to give Compound 4-173 (309 mg, 61%) as red solid. LCMS: 425 $[M+H]^+$.

5-(tert-butyl) 1-ethyl 6,6-dimethyl-3-((6-nitroisoquinolin-1-yl)amino)-4,6-dihydropyrrolo[3,4-c]pyrazole-1,5-dicarboxylate (Compound 4-174)

To a solution of Compound 4-173 (309 mg, 0.73 mmol) and DIEA (241 uL, 1.46 mmol) in THF (5 mL) was added ethyl chloroformate (70 uL, 1.3 mmol) at 0° C. The mixture was stirred at 50° C. for 1 h, concentrated, and extracted with EA. The organic layer was washed with water twice and concentrated under reduced pressure to give Compound 4-174, which was used to next step without any purification. LCMS: 497 $[M+H]^+$.

Ethyl 6,6-dimethyl-3-((6-nitroisoquinolin-1-yl)amino)-5,6-dihydropyrrolo[3,4-c]pyrazole-1(4H)-carboxylate TFA salt (Compound 4-175)

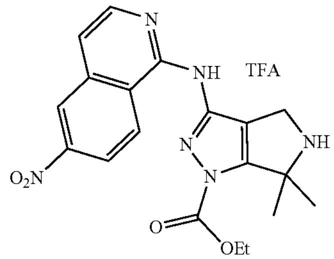 [SMILES: CCOC(=O)n1nc(Nc2nccc3cc([N+](=O)[O-])ccc23)c2c1C(C)(C)NC2]

Compound 4-174 (0.73 mmol) obtained from last step was dissolved in TFA/DCM (v/v=1/3, 8 mL). The mixture was stirred at room temperature for 1 h, concentrated under reduced pressure, and purified by prep-HPLC (MeOH/water, 0.035% TFA) to give Compound 4-175 (162 mg, 44% for 2 steps) as TFA salt. LCMS: 397 $[M+H]^+$.

Ethyl (S)-5-((2-(dimethylamino)-1-(tetrahydro-2H-pyran-4-yl)ethyl)carbamoyl)-6,6-dimethyl-3-((6-nitroisoquinolin-1-yl)amino)-5,6-dihydropyrrolo[3,4-c]pyrazole-1(4H)-carboxylate (Compound 4-179)

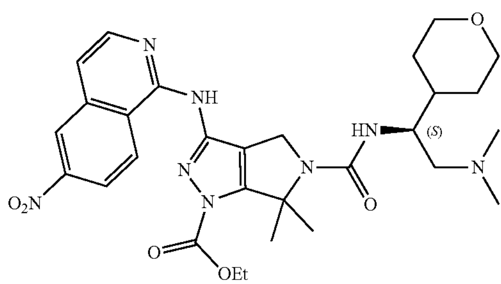

To a solution of (S)—$N^1$,$N^1$-dimethyl-2-(tetrahydro-2H-pyran-4-yl)ethane-1,2-diamine (45 mg, 0.26 mmol) in dry toluene (2 mL) was added phosgene (15% w.t. in toluene, 0.2 mL). The mixture was stirred at 80° C. for 2 h and concentrated under reduced pressure. The residue was dissolved in dioxane (3 mL), then Compound 4-175 (85 mg, 0.17 mmol) and DIEA (129 uL, 0.78 mmol) were added. The mixture was stirred at 80° C. for another 2 h, concentrated under reduced pressure, and then purified by silica gel column chromatography (MeOH/DCM=0-15%) to give Compound 4-179 (44 mg, 45%) as orange solid. LCMS: 595 $[M+H]^+$.

Ethyl (S)-3-((6-aminoisoquinolin-1-yl)amino)-5-((2-(dimethylamino)-1-(tetrahydro-2H-pyran-4-yl)ethyl)carbamoyl)-6,6-dimethyl-5,6-dihydropyrrolo[3,4-c]pyrazole-1(4H)-carboxylate (Compound 4-182)

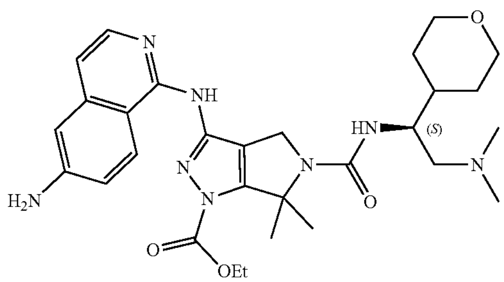

To a solution of Compound 4-179 (44 mg, 0.074 mmol) in MeOH (10 mL) was added Pd/C. The mixture was stirred at room temperature under $H_2$ atmosphere for 3 h and filtered. The filtrate was concentrated under reduced pressure to give Compound 4-182 (42 mg, 100%) as white solid. LCMS: 565 $[M+H]^+$.

(S)-3-(3-(4-acrylamidobenzamido)benzamido)-N-(2-(dimethylamino)-1-phenylethyl)-6,6-dimethyl-4,6-dihydropyrrolo[3,4-c]pyrazole-5(1H)-carboxamide (Compound 202)

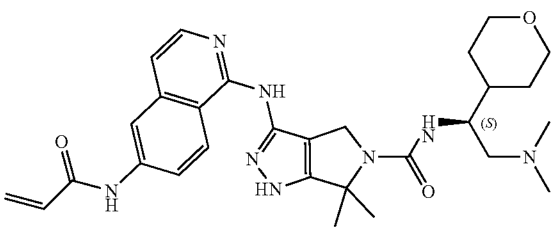

To a solution of Compound 4-182 (42 mg, 0.074 mmol) in acetonitrile (2 mL) was added acryloyl chloride (diluted in acetonitrile) dropwise at 0° C. until reaction was finished. The mixture was then extracted with excess EA and washed with water twice. The organic layer was then concentrated under reduced pressure and dissolved in the mixture of isopropanol (IPA, 1 mL) and LiOH (1M aq., 1 mL). The resulting mixture was stirred at room temperature for 10 min, concentrated under reduced pressure, and purified by prep-HPLC (MeOH/water, 0.035% TFA) to give a TFA salt of Compound 202 (10.1 mg, 21%). LCMS: 547 $[M+H]^+$. $^1H$ NMR (500 MHz, DMSO-$d_6$) δ 11.62 (s, 1H), 10.94 (s, 1H), 9.21 (s, 1H), 8.76 (d, J=9.1 Hz, 1H), 8.45 (d, J=2.1 Hz, 1H), 7.99 (dd, J=9.1, 2.2 Hz, 1H), 7.93 (d, J=6.9 Hz, 1H), 7.46 (d, J=6.9 Hz, 1H), 6.55 (dd, J=16.9, 10.2 Hz, 1H), 6.39 (dd, J=17.0, 1.8 Hz, 1H), 5.99-5.77 (m, 2H), 4.52 (dd, J=57.5, 11.6 Hz, 2H), 3.98 (d, J=9.3 Hz, 1H), 3.86 (d, J=10.3 Hz, 2H), 3.25 (dd, J=12.1, 5.6 Hz, 4H), 2.82 (t, J=5.1 Hz, 6H), 1.73 (s, 6H), 1.67 (d, J=7.0 Hz, 1H), 1.55 (d, J=13.0 Hz, 2H), 1.32-1.24 (m, 2H).

Example 1.5. (S)-3-((5-acrylamidoisoquinolin-1-yl)amino)-N-(2-(dimethylamino)-1-(tetrahydro-2H-pyran-4-yl)ethyl)-6,6-dimethyl-4,6-dihydropyrrolo[3,4-c]pyrazole-5(1H)-carboxamide (Compound 203)

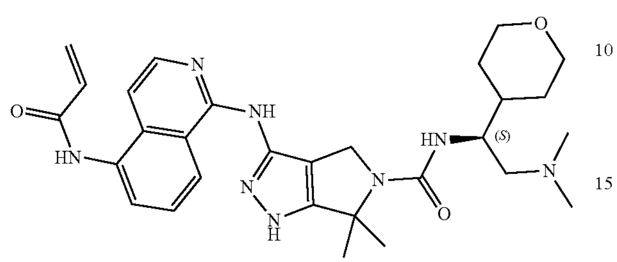

Compound 203 (4.5 mg, 14%) was obtained according to the synthetic route of Compound 202, except that 1-chloro-6-nitroisoquinoline was changed to 1-chloro-5-nitroisoquinoline. LCMS: 547 $[M+H]^+$. $^1H$ NMR (500 MHz, DMSO-$d_6$) δ 10.69 (s, 1H), 10.26 (s, 1H), 8.97 (s, 1H), 8.48 (d, J=8.4 Hz, 1H), 8.11 (d, J=7.7 Hz, 1H), 8.05 (d, J=6.4 Hz, 1H), 7.73 (t, J=8.0 Hz, 1H), 7.40 (s, 1H), 6.69 (dd, J=17.0, 10.2 Hz, 1H), 6.34 (dd, 7=17.0, 1.9 Hz, 1H), 5.93-5.81 (m, 2H), 4.59-4.42 (m, 2H), 3.98 (td, J=11.9, 11.3, 7.2 Hz, 1H), 3.87 (dd, J=10.8, 4.1 Hz, 2H), 3.24 (td, J=11.4, 10.6, 4.0 Hz, 4H), 2.81 (t, J=5.0 Hz, 6H), 1.71 (d, J=6.5 Hz, 3H), 1.66 (dd, J=7.7, 3.8 Hz, 1H), 1.55 (d, J=13.0 Hz, 2H), 1.26 (dt, J=12.3, 5.6 Hz, 2H).

Example 1.6. (S)-3-((5-acrylamidopyridin-2-yl)amino)-N-(2-(dimethylamino)-1-(tetrahydro-2H-pyran-4-yl)ethyl)-6,6-dimethyl-4,6-dihydropyrrolo[3,4-c]pyrazole-5(1H)-carboxamide (Compound 204)

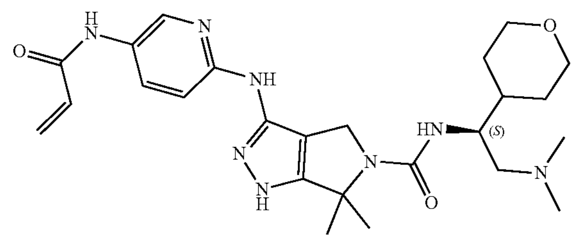

Compound 204 (1.6 mg, 7%) was obtained according to the synthetic route of Compound 202, except that 1-chloro-6-nitroisoquinoline was changed to 2-chloro-5-nitropyridine. LCMS: 497 $[M+H]^+$. $^1H$ NMR (500 MHz, DMSO-$d_6$) δ 10.29 (s, 1H), 10.00 (s, 1H), 9.01 (s, 1H), 8.61 (d, J=2.6 Hz, 1H), 7.92 (dd, J=9.1, 2.6 Hz, 1H), 7.00 (d, J=9.1 Hz, 1H), 6.43 (dd, J=17.0, 10.2 Hz, 1H), 6.26 (dd, J=17.0, 2.0 Hz, 1H), 5.89 (d, J=9.2 Hz, 1H), 5.78 (dd, J=10.1, 2.0 Hz, 1H), 4.51 (d, J=11.5 Hz, 1H), 4.38 (d, J=11.4 Hz, 1H), 3.97 (s, 1H), 3.88 (td, J=11.9, 4.0 Hz, 2H), 3.22 (d, J=13.7 Hz, 4H), 2.81 (dd, J=4.9, 2.1 Hz, 6H), 1.67 (d, J=7.6 Hz, 6H), 1.59-1.50 (m, 2H), 1.28-1.20 (m, 2H).

Example 1.7. (S)-3-((5-acrylamidopyrimidin-2-yl)amino)-N-(2-(dimethylamino)-1-(tetrahydro-2H-pyran-4-yl)ethyl)-6,6-dimethyl-4,6-dihydropyrrolo[3,4-c]pyrazole-5(1H)-carboxamide (Compound 206)

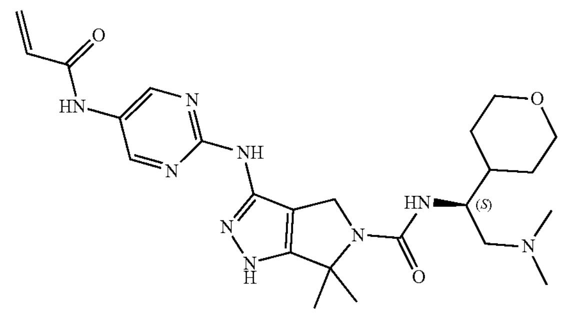

Compound 206 (2.2 mg, 5%) was obtained according to the synthesis route of Compound 202, except that 1-chloro-6-nitroisoquinoline changed to 2-chloro-5-nitropyrimidine. LCMS: 498 $[M+H]^+$. $^1H$ NMR (500 MHz, DMSO-$d_6$) δ 12.07 (s, 1H), 10.23 (s, 1H), 9.70 (s, 1H), 8.71 (s, 2H), 6.42 (dd, J=17.0, 10.1 Hz, 1H), 6.27 (dd, J=17.0, 1.9 Hz, 1H), 5.79 (dd, J=10.1, 2.0 Hz, 1H), 5.38 (s, 1H), 4.39 (d, J=18.7 Hz, 2H), 3.85 (ddd, J=16.8, 11.6, 4.3 Hz, 2H), 3.75 (p, J=7.1 Hz, 1H), 3.26-3.15 (m, 2H), 2.31 (d, J=7.5 Hz, 2H), 2.16 (s, 6H), 1.62 (s, 6H), 1.51 (t, J=14.8 Hz, 2H), 1.35-1.26 (m, 2H).

Example 1.8. (S)-3-((4-acrylamidophenyl)amino)-N-(2-(dimethylamino)-1-(tetrahydro-2H-pyran-4-yl)ethyl)-6,6-dimethyl-4,6-dihydropyrrolo[3,4-c]pyrazole-5(1H)-carboxamide (Compound 209)

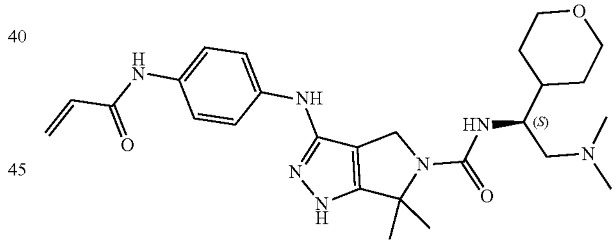

Compound 209 was (2.4 mg, 7%) obtained according to the synthesis route of Compound 202, except that 1-chloro-6-nitroisoquinoline was changed to 1-chloro-4-nitrobenzene. LCMS: 496 $[M+H]^+$. $^1H$ NMR (500 MHz, DMSO-$d_6$) δ 11.95 (s, 1H), 9.91 (s, 1H), 8.19 (s, 1H), 7.50 (d, J=8.5 Hz, 1H), 6.40 (dd, J=17.0, 10.1 Hz, 2H), 6.20 (dd, J=17.0, 2.1 Hz, 1H), 5.69 (dd, J=10.1, 2.1 Hz, 1H), 5.37 (s, 1H), 4.20 (s, 2H), 3.83 (d, J=13.0 Hz, 2H), 3.77-3.69 (m, 1H), 3.20 (d, J=9.6 Hz, 2H), 2.28 (d, J=7.3 Hz, 1H), 2.14 (s, 6H), 1.62 (s, 6H), 1.49 (t, J=16.8 Hz, 2H), 1.24 (s, 2H).

Example 1.9. (S)-3-(4-acrylamidobenzamido)-N-(2-(dimethylamino)-1-(tetrahydro-2H-pyran-4-yl)ethyl)-6,6-dimethyl-4,6-dihydropyrrolo[3,4-c]pyrazole-5(1H)-carboxamide (Compound 205)

The synthesis of Compound 205 follows Scheme 3. The synthesis of Compound 207, Compound 210, Compound 065 and Compound 079 follow a similar method.

Scheme 3.

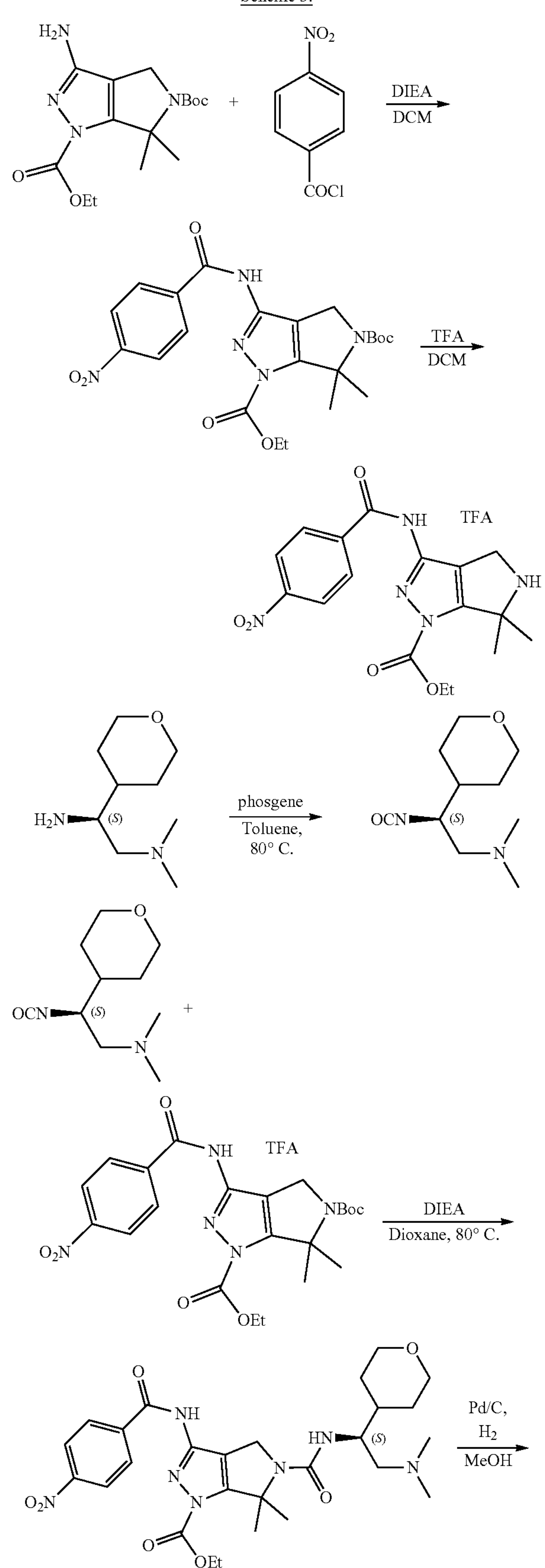

-continued

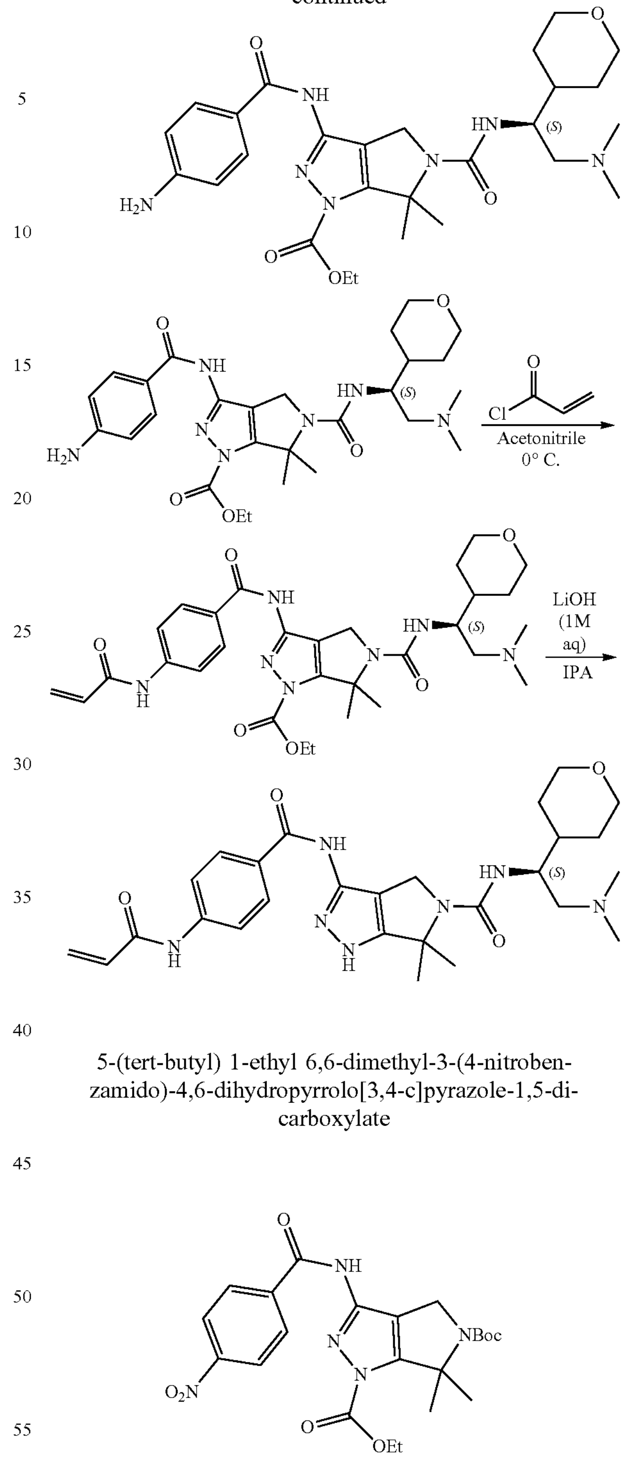

5-(tert-butyl) 1-ethyl 6,6-dimethyl-3-(4-nitrobenzamido)-4,6-dihydropyrrolo[3,4-c]pyrazole-1,5-dicarboxylate To a solution of 5-(tert-butyl) 1-ethyl 3-amino-6,6-dimethyl-4,6-dihydropyrrolo[3,4-c]pyrazole-1,5-dicarboxylate (1135 mg, 3.5 mmol) and 4-nitrobenzoyl chloride (775 mg, 4.2 mmol) in DCM (25 mL) was added DIEA (1.7 mL, 10.5 mmol), the mixture was stirred at room temperature for 4 h, and then concentrated under reduced pressure, purified by silica gel column chromatography (EA/hexane=0-35%) to give 5-(tert-butyl) 1-ethyl 6,6-dimethyl-3-(4-nitrobenzamido)-4,6-dihydropyrrolo[3,4-c]pyrazole-1,5-dicarboxylate (520 mg, 31%) as yellow solid. LCMS: 474 $[M+H]^+$.

Ethyl 6,6-dimethyl-3-(4-nitrobenzamido)-5,6-dihydropyrrolo[3,4-c]pyrazole-1(4H)-carboxylate

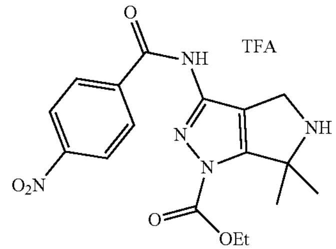 [SMILES: CCOC(=O)n1nc(NC(=O)c2ccc([N+](=O)[O-])cc2)c2c1C(C)(C)NC2]

The product from last step was dissolved in TFA/DCM (v/v=1/3, 4 mL), stirred at room temperature for 1 h, and then concentrated under reduced pressure, used to next step without any purification. LCMS: 374 $[M+H]^+$.

Ethyl (S)-5-((2-(dimethylamino)-1-(tetrahydro-2H-pyran-4-yl)ethyl)carbamoyl)-6,6-dimethyl-3-(4-nitrobenzamido)-5,6-dihydropyrrolo[3,4-c]pyrazole-1(4H)-carboxylate

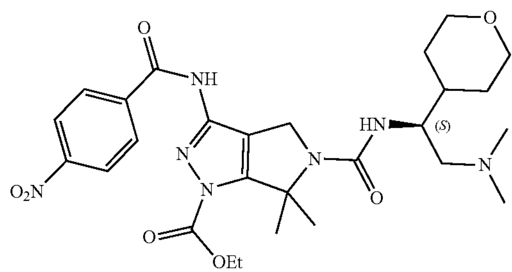

To a solution (S)—$N^1$,$N^1$-dimethyl-2-(tetrahydro-2H-pyran-4-yl)ethane-1,2-diamine (103 mg, 0.6 mmol) in dry toluene (2 mL) was added phosgene (15% w.t. in toluene, 0.4 mL), the mixture was stirred at 80° C. for 2 h. The mixture was then concentrated under reduced pressure, dissolved in dioxane (4 mL), and then ethyl 6,6-dimethyl-3-(4-nitrobenzamido)-5,6-dihydropyrrolo[3,4-c]pyrazole-1(4H)-carboxylate (263 mg, 0.54 mmol) and DIEA (297 uL, 1.8 mmol) were added, then the mixture was stirred at 80° C. for another 2 h. The mixture was concentrated under reduced pressure and then purified by silica gel column chromatography (MeOH/DCM=0-15%) to give ethyl (S)-5-((2-(dimethylamino)-1-(tetrahydro-2H-pyran-4-yl)ethyl)carbamoyl)-6,6-dimethyl-3-(4-nitrobenzamido)-5,6-dihydropyrrolo[3,4-c]pyrazole-1(4H)-carboxylate (130 mg, 42%). LCMS: 572 $[M+H]^+$.

Ethyl (S)-3-(4-aminobenzamido)-5-((2-(dimethylamino)-1-(tetrahydro-2H-pyran-4-yl)ethyl)carbamoyl)-6,6-dimethyl-5,6-dihydropyrrolo[3,4-c]pyrazole-1(4H)-carboxylate

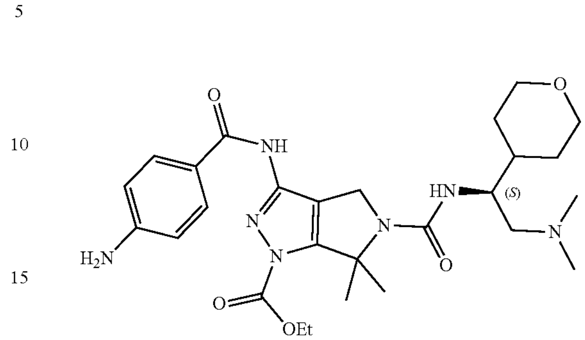

The product (130 mg, 0.23 mmol) from last step was dissolved in MeOH (10 mL), Pd/C was added, and then the mixture was stirred at room temperature under $H_2$ atmosphere for 3 h. Filtered, then the filtrate was concentrated under reduced pressure to give ethyl (S)-3-(4-aminobenzamido)-5-((2-(dimethylamino)-1-(tetrahydro-2H-pyran-4-yl)ethyl)carbamoyl)-6,6-dimethyl-5,6-dihydropyrrolo[3,4-c]pyrazole-1(4H)-carboxylate (125 mg, 100%). LCMS: 542 $[M+H]^+$.

(S)-3-(4-acrylamidobenzamido)-N-(2-(dimethylamino)-1-(tetrahydro-2H-pyran-4-yl)ethyl)-6,6-dimethyl-4,6-dihydropyrrolo[3,4-c]pyrazole-5(1H)carboxamide (Compound 205)

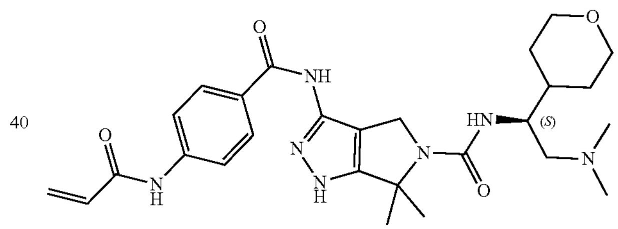

To a solution of ethyl (S)-3-(4-aminobenzamido)-5-((2-(dimethylamino)-1-(tetrahydro-2H-pyran-4-yl)ethyl)carbamoyl)-6,6-dimethyl-5,6-dihydropyrrolo[3,4-c]pyrazole-1(4H)-carboxylate (125 mg, 0.23 mmol) in acetonitrile (3 mL) was added acryloyl chloride (diluted in acetonitrile) dropwise at 0° C. until reaction finished. The mixture was then extracted with isopropanol/chloroform (v/v=1/3) and washed with water twice, the organic layer was then concentrated under reduced pressure, purified by silica gel column chromatography (MeOH/DCM=0-20%) to give ethyl (S)-3-(4-acrylamidobenzamido)-5-((2-(dimethylamino)-1-(tetrahydro-2H-pyran-4-yl)ethyl)carbamoyl)-6,6-dimethyl-5,6-dihydropyrrolo[3,4-c]pyrazole-1(4H)-carboxylate (17 mg, 12%). The intermediate was then dissolved in the mixture of isopropanol (IPA, 1 mL) and LiOH (1M aq., 1 mL), stirred at room temperature for 10 min, and then concentrated under reduced pressure, purified by silica gel column chromatography (1.75 N $NH_3$ in MeOH/DCM=0-30%) to give Compound 205 (12.3 mg, 80%). LCMS: 524 $[M+H]^+$. $^1$H NMR (500 MHz, DMSO-$d_6$) δ 10.81 (s, 1H), 10.44 (s, 1H), 8.79 (s, 1H), 8.01 (d, J=8.6 Hz, 2H), 7.79 (d, J=8.6 Hz, 2H), 6.48 (dd, J=17.0, 10.2 Hz, 1H), 6.31 (dd, J=17.0, 1.9 Hz, 1H), 6.00 (d, J=9.3 Hz, 1H), 5.82 (dd, J=10.1, 1.9 Hz, 1H), 4.66 (d, J=11.8 Hz, 1H), 4.48 (d, J=11.8 Hz, 1H), 3.98 (p, J=8.0 Hz, 1H), 3.87 (td, J=10.9, 4.0 Hz, 2H), 3.27-3.20 (m, 4H), 2.79 (dd, J=10.5, 4.8 Hz, 6H), 1.66 (d, J=11.2 Hz, 6H), 1.57-1.47 (m, 2H), 1.23 (qt, J=12.7, 6.4 Hz, 2H).

Example 1.10. 3-(4-acrylamidobenzamido)-6,6-dimethyl-N-(2-methyl-1,2,3,4-tetrahydroisoquinolin-4-yl)-4,6-dihydropyrrolo[3,4-c]pyrazole-5(1H)-carboxamide (Compound 207)

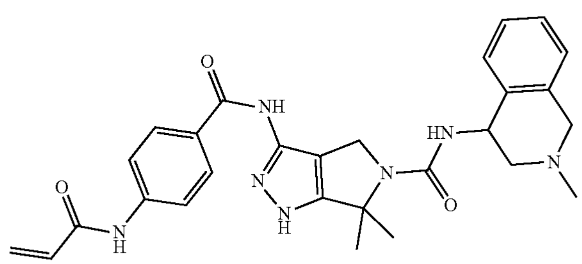 [SMILES: C=CC(=O)Nc1ccc(C(=O)Nc2n[nH]c3c2CN(C(=O)NC2CN(C)Cc4ccccc42)C3(C)C)cc1]

Compound 207 (10 mg, 45%) was obtained according to the synthesis route of Compound 205, except that (S)—N$^1$/N$^1$-dimethyl-2-(tetrahydro-2H-pyran-4-yl)ethane-1,2-diamine was changed to 2-methyl-1,2,3,4-tetrahydroisoquinolin-4-amine. LCMS: 514 [M+H]$^+$.

$^1$H NMR (500 MHz, DMSO-d$_6$) δ 12.43 (s, 1H), 10.75 (s, 1H), 10.40 (s, 1H), 7.97 (d, J=8.4 Hz, 2H), 7.75 (d, J=8.2 Hz, 2H), 7.35 (d, J=7.4 Hz, 1H), 7.19 (tt, J=8.0, 6.4 Hz, 2H), 7.07 (d, J=7.3 Hz, 1H), 6.46 (dd, J=16.9, 10.1 Hz, 1H), 6.30 (dd, J=17.0, 1.9 Hz, 2H), 5.81 (dd, J=10.1, 1.9 Hz, 1H), 5.05 (q, J=8.3 Hz, 1H), 4.49 (q, J=11.8 Hz, 2H), 3.65 (d, J=15.0 Hz, 1H), 3.41 (d, J=15.4 Hz, 1H), 3.18 (d, J=5.0 Hz, 1H), 2.86 (dd, J=11.2, 5.5 Hz, 1H), 2.51 (t, J=2.0 Hz, 3H), 2.37 (s, 3H), 1.71 (d, J=20.9 Hz, 6H).

Example 1.11. (S)-3-(4-acrylamidobenzamido)-6,6-dimethyl-N-(1-methylpiperidin-3-yl)-4,6-dihydropyrrolo[3,4-c]pyrazole-5(1H)-carboxamide (Compound 210)

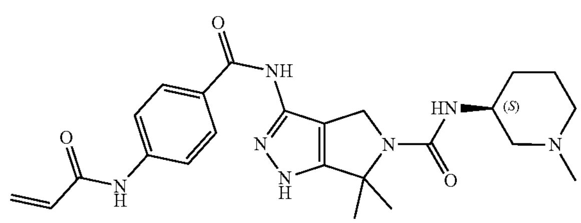

Compound 210 (7.5 mg, 14%) was obtained according to the synthesis route of Compound 205, except that (S)—N$^1$,N$^1$-dimethyl-2-(tetrahydro-2/7-pyran-4-yl)ethane-1,2-diamine was changed to (S)-1-methylpiperidin-3-amine. LCMS: 466 [M+H]$^+$. $^1$H NMR (500 MHz, DMSO-d$_6$) δ 12.44 (s, 1H), 10.79 (s, 1H), 10.43 (s, 1H), 9.54 (s, 1H), 8.01 (d, J=8.4 Hz, 2H), 7.78 (d, J=8.4 Hz, 2H), 6.48 (dd, J=17.0, 10.1 Hz, 1H), 6.31 (dd, J=16.9, 1.9 Hz, 1H), 5.82 (dd, J=10.0, 2.0 Hz, 1H), 4.49 (s, 2H), 3.87 (s, 1H), 3.31 (s, 2H), 2.76 (s, 3H), 1.92-1.74 (m, 2H), 1.69-1.60 (m, 7H), 1.50 (s, 1H).

Example 1.12. 3-(4-acrylamidobenzamido)-N-(1-((dimethylamino)methyl)cyclopropyl)-6,6-dimethyl-4,6-dihydropyrrolo[3,4-c]pyrazole-5(1H)carboxamide (065)

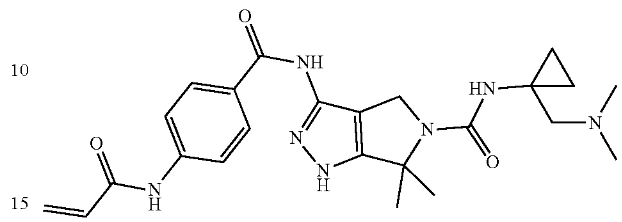

Compound 065 (6.3 mg, 22%) was obtained according to synthesis route of Compound 205, except that (S)—N$^1$,N$^1$-dimethyl-2-(tetrahydro-2/7-pyran-4-yl)ethane-1,2-diamine was changed to 1-[(dimethylamino)methyl]cyclopropan-1-amine. LCMS: 466 [M+H]$^+$. $^1$H NMR (500 MHz, DMSO-d$_6$) δ 12.41 (s, 1H), 10.74 (s, 1H), 10.44 (s, 1H), 8.00 (d, J=8.5 Hz, 2H), 7.78 (d, J=8.4 Hz, 2H), 6.48 (dd, J=17.0, 10.1 Hz, 1H), 6.31 (dd, J=17.0, 1.9 Hz, 2H), 5.82 (dd, J=10.1, 1.9 Hz, 1H), 4.41 (s, 2H), 2.69-2.57 (m, 2H), 2.39 (s, 6H), 1.65 (s, 6H), 0.76 (s, 2H), 0.59 (s, 2H).

Example 1.13. 3-(4-acrylamidobenzamido)-N-(2-(dimethylamino)-1-(tetrahydrofuran-3-yl)ethyl)-6,6-dimethyl-4,6-dihydropyrrolo[3,4-c]pyrazole-5(1H)-carboxamide (079)

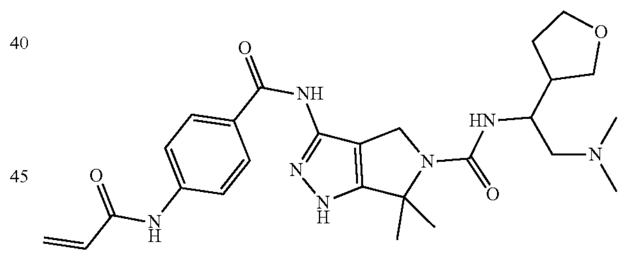

Compound 079 (3 mg, 18%) was obtained according to synthesis route of Compound 205, except that (S)—N$^1$,N$^1$-dimethyl-2-(tetrahydro-2H-pyran-4-yl)ethane-1,2-diamine was changed to N$^1$,N$^1$-dimethyl-2-(tetrahydrofuran-3-yl)ethane-1,2-diamine. LCMS: 510 [M+H]$^+$.

Example 2. Biological Assays of the Compounds

Example 2.1. Inhibition of Kinase Activity

Compounds of the disclosure were assayed using Invitrogen CDK7 assay against a variety of kinases. Exemplary results are presented as $IC_{50}$ values (see Table 1 and Table 2). The co-factors used for each kinase in the assays were as follows: CDK7: cyclin H and MNAT1; CDK2: cyclin A; CDK9: cyclin T1.

TABLE 1
IC$_{50}$ values of exemplary compounds against select kinases.
| Compound No. | Compound Formula | IC$_{50}$ against CDK2 (nM) | IC$_{50}$ against CDK7 (nM) | IC$_{50}$ against CDK9 (nM) |
|---|---|---|---|---|
| 200 | 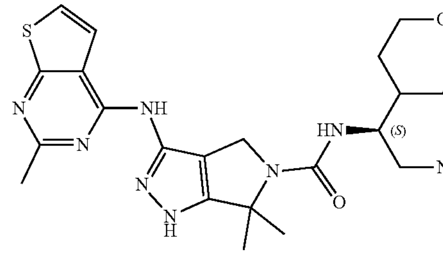 | >10000 | 18.5 | >10000 |
| 201 | 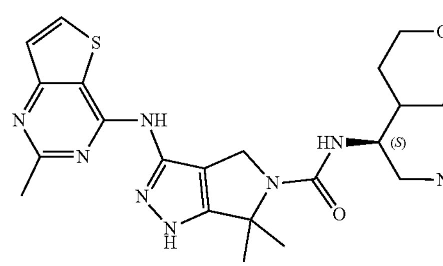 | >10000 | 39.1 | >10000 |
| 202 | 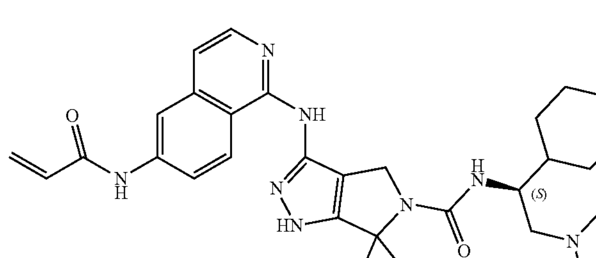 | >1110 | 69 | >10000 |
| 203 | 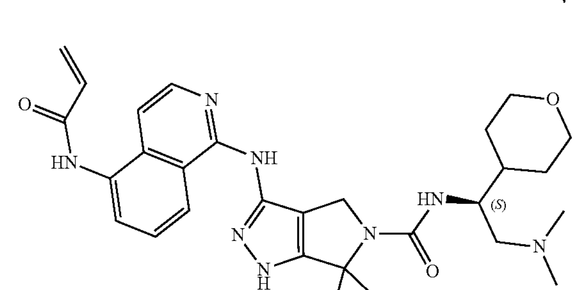 | >10000 | 214 | >10000 |
| 204 | 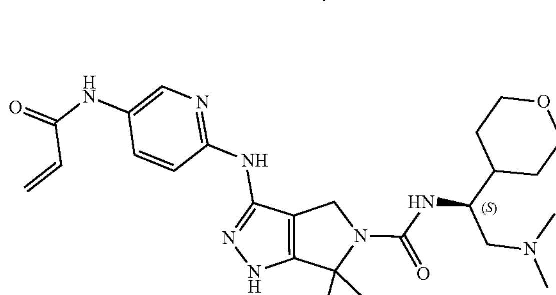 | >10000 | 407 | >10000 |

TABLE 1-continued
| IC$_{50}$ values of exemplary compounds against select kinases. | | | | |
|---|---|---|---|---|
| Compound No. | Compound Formula | IC$_{50}$ against CDK2 (nM) | IC$_{50}$ against CDK7 (nM) | IC$_{50}$ against CDK9 (nM) |
| 205 | 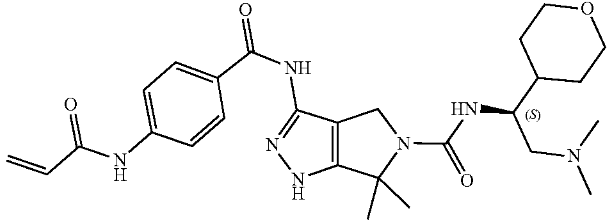 | >370 | 12.8 | 4010 |
TABLE 2
| IC$_{50}$ values of additional exemplary compounds against select kinases. | | | | |
|---|---|---|---|---|
| Compound No. | Compound Formula | IC$_{50}$ against CDK2 (nM) | IC$_{50}$ against CDK7 (nM) | IC$_{50}$ against CDK9 (nM) |
| 206 | 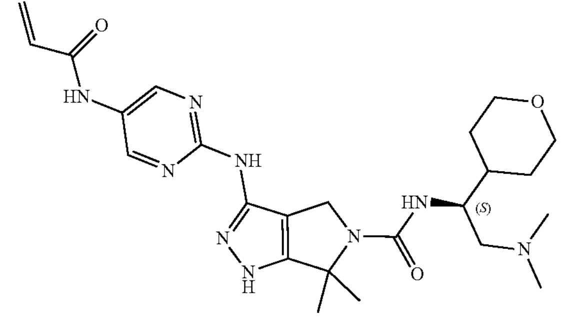 | >10000 | 732 | >10000 |
| 207 | 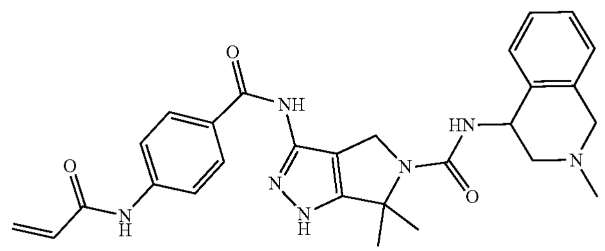 [SMILES: C=CC(=O)Nc1ccc(C(=O)Nc2n[nH]c3c2CN(C(=O)NC2CN(C)Cc4ccccc42)C3(C)C)cc1] | 3410 | 15.4 | >10000 |
| 208 | 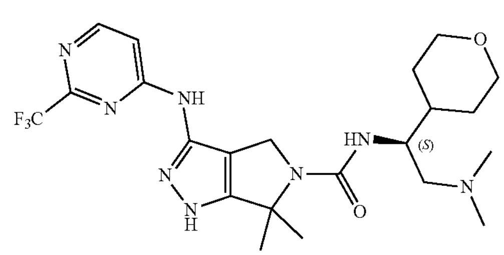 | 4520 | 10.8 | >10000 |

TABLE 2-continued

| IC$_{50}$ values of additional exemplary compounds against select kinases. | | | | |
|---|---|---|---|---|
| Compound No. | Compound Formula | IC$_{50}$ against CDK2 (nM) | IC$_{50}$ against CDK7 (nM) | IC$_{50}$ against CDK9 (nM) |
| 209 | | >10000 | 3310 | >10000 |
| 210 | | 161 | 48.4 | 1740 |
| 065 | | >10000 | 61.1 | >10000 |
| 079 | | >10000 | 190 | 1060 |

Example 2.2. Pull Down of CDK12/13 and CDK7 Complexes

Briefly, Jurkat T-cells (acute lymphoblastic leukemia) were treated with test compounds (at 1 μM to 2.5 μM) or DMSO for 6 hours. Cellular lysates were made from each treatment condition and clarified lysates were incubated with either DMSO or 1 μM biotinylated THZ1 (bio-THZ1), a concentration that binds CDK7-cyclin H, CDK12-cyclin K, and CDK13-cyclin K complexes. Subsequent addition of streptavidin-coated beads permits the immunopreciptation (or pull down) of the indicated protein complexes. Following washing of beads with lysis buffer, the immunoprecipitated proteins were eluted from the beads by boiling in SDS buffer. Western blotting of precipitated proteins with cyclin K was used to identify precipitated CDK12-cyclin K or CDK13-cyclin K complexes; while western blotting with cyclin H was used to identify precipitated CDK7-cyclin H complexes. Active test compounds are expected to bind CDK7, thus pre-treatment with active compounds is expected to block subsequent binding and immunoprecipitation of CDK7-cylin H complexes with bio-THZ1. Note: THZ1 binds CDK7, CDK12, and CDK13 and blocks pull down of all these complexes.

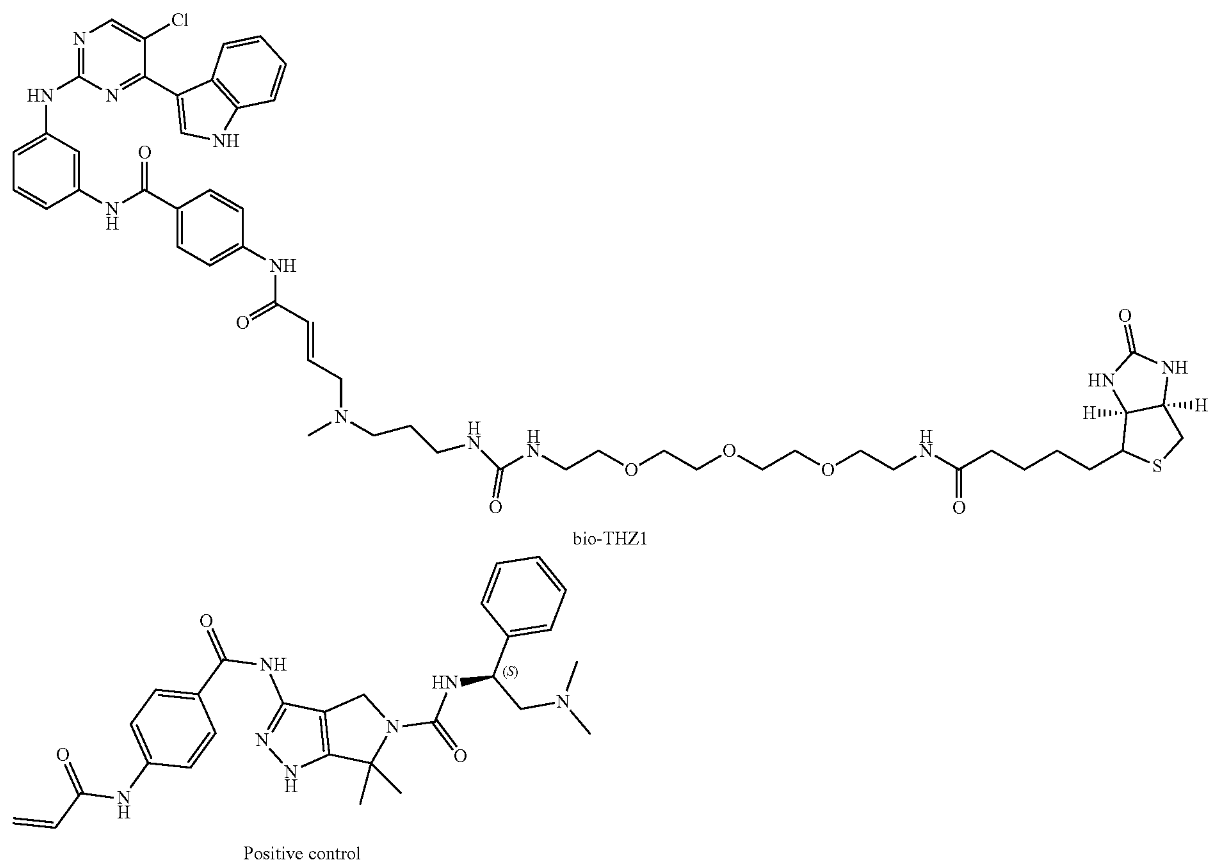

bio-THZ1

Positive control

Figure 6:
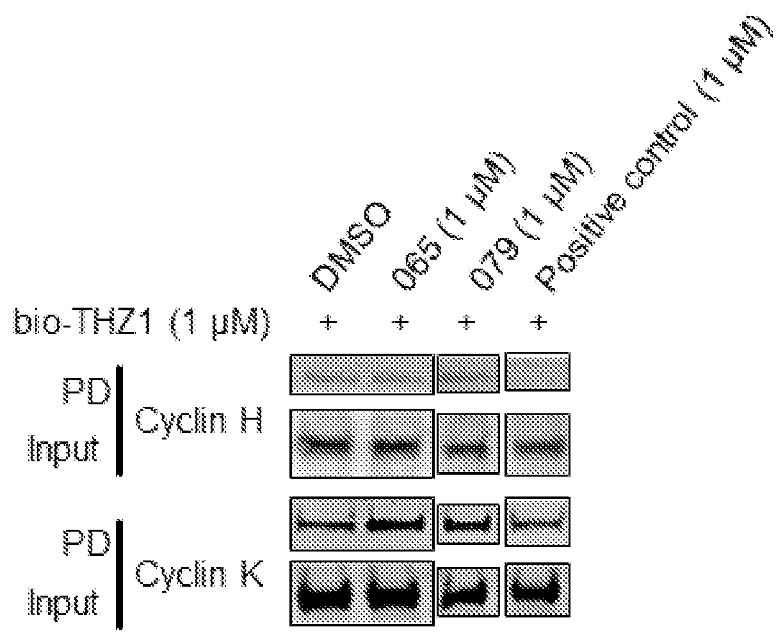
FIG. 6 shows exemplary results of a pull down assay of compounds 065 and 079 at 1 μM. Experimental details are described elsewhere. Western blotting with cyclin H identifies CDK7-cyclin H complexes (CDK7), while western blotting with cyclin K identifies CDK12-cyclin K and CDK13-cyclin K complexes.

Exemplary results are shown in FIGS. 1 to 5. Additional exemplary results are shown in FIG. 6.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising," "including," and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of Formula (I):

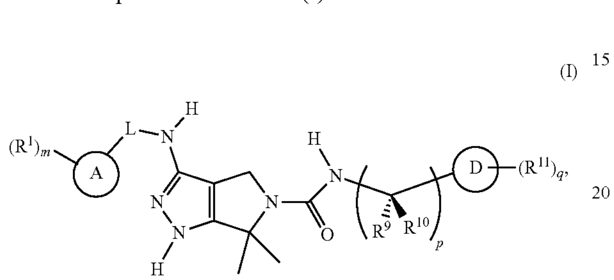

or a pharmaceutically acceptable salt, solvate, hydrate, tautomer, stereoisomer, or isotopically labeled derivative thereof, wherein:

Ring A is aryl, or heteroaryl;

$R^1$ is of the formula —NHC(O)CH═$CH_2$ or $L^3$;

wherein:

$L^3$ is a substituted or unsubstituted $C_{1-4}$ hydrocarbon chain;

m is 0 or 1;

L is a single bond or —C(═O)—;

one of $R^9$ and $R^{10}$ is hydrogen and the other is —($CH_2$)N $(CH_3)_2$;

p is 0 or 1 such that when p=0, then D=piperidinyl, 1,2,3,4-tetrahydroisoquinolinyl, or

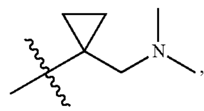 [SMILES: *C1(CN(C)C)CC1]

and when p=1, then D=tetrahydropyranyl or tetrahydrofuryl;

$R^{11}$ is substituted or unsubstituted alkyl; and q is 0 or 1.

2. The compound of claim 1, or a pharmaceutically acceptable salt, solvate, hydrate, tautomer, stereoisomer, or isotopically labeled derivative thereof, wherein the compound is of the formula:

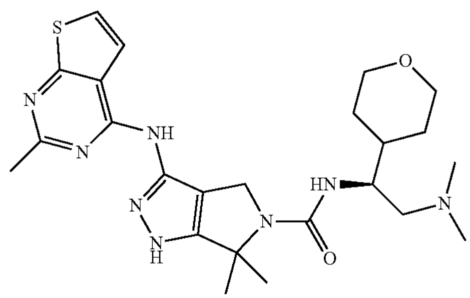

-continued

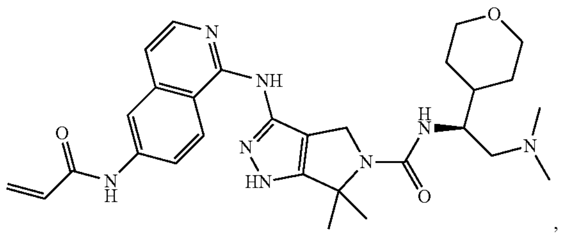

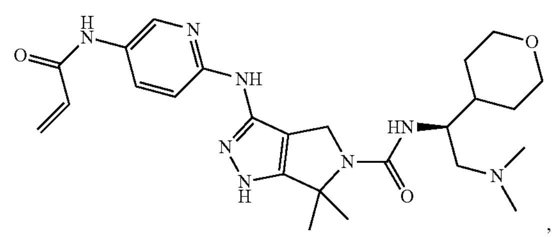

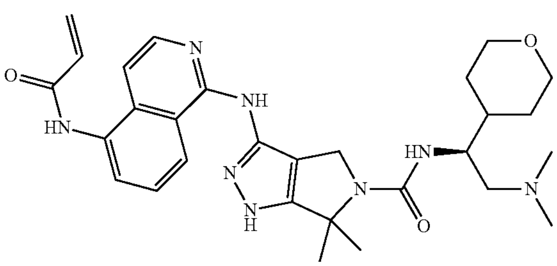

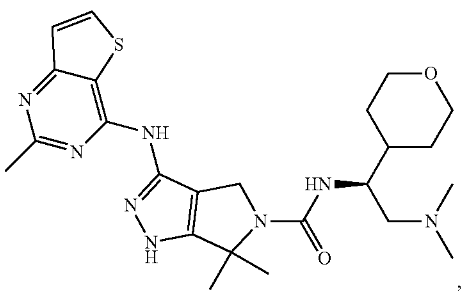

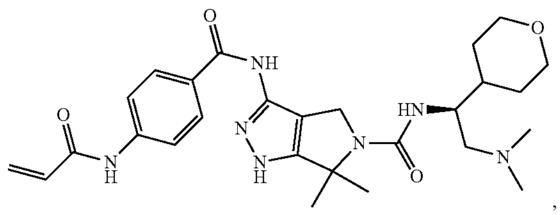

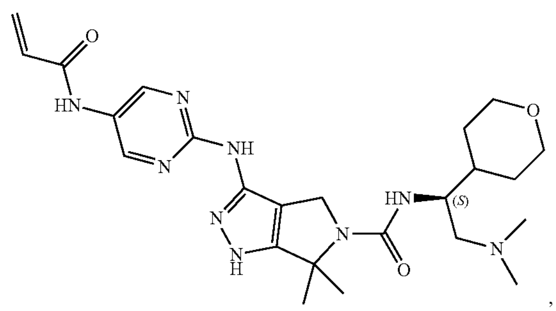

-continued

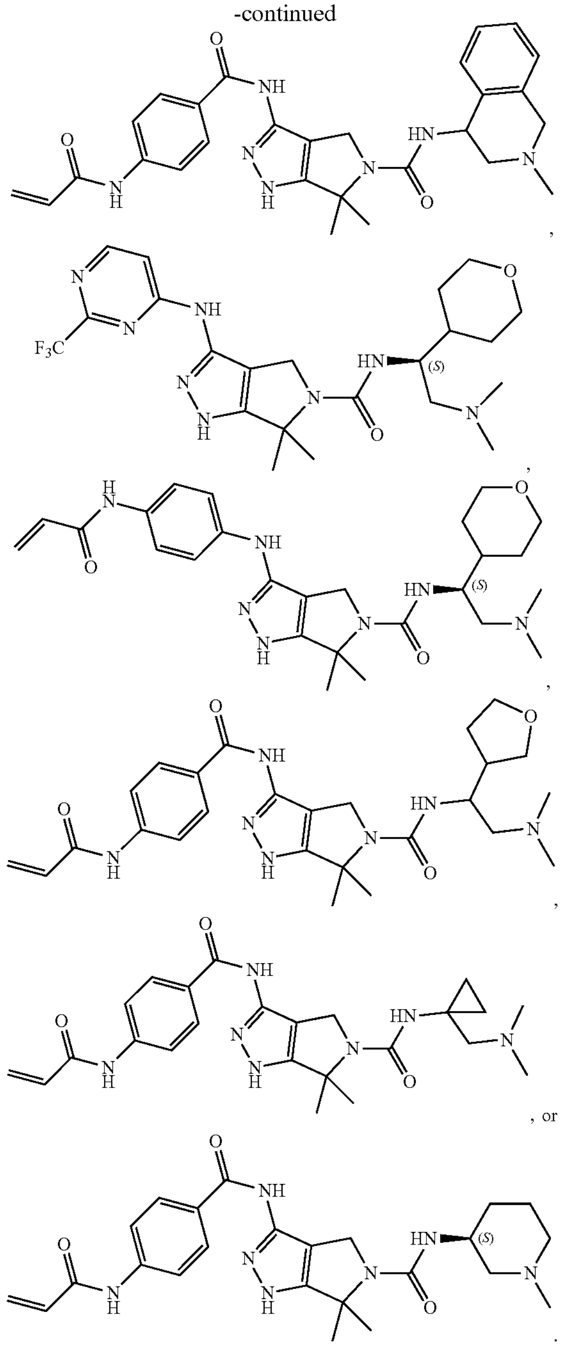

3. The compound of claim 1, or a pharmaceutically acceptable salt, tautomer, or stereoisomer thereof.

4. A compound of claim 1, or a pharmaceutically acceptable salt, solvate, hydrate, tautomer, stereoisomer, or isotopically labeled derivative thereof, wherein A is aryl.

5. A compound of claim 4, or a pharmaceutically acceptable salt, solvate, hydrate, tautomer, stereoisomer, or isotopically labeled derivative thereof, wherein A is phenyl.

6. A compound of claim 1, or a pharmaceutically acceptable salt, solvate, hydrate, tautomer, stereoisomer, or isotopically labeled derivative thereof, wherein A is heteroaryl.

7. A compound of claim 6, or a pharmaceutically acceptable salt, solvate, hydrate, tautomer, stereoisomer, or isotopically labeled derivative thereof, wherein A is selected from thieno[2,3-d]pyrimidinyl, thieno[3,2-d]pyrimidinyl, isoquinolinyl, pyridinyl, and pyrimidinyl.

8. A compound of claim 1, or a pharmaceutically acceptable salt, solvate, hydrate, tautomer, stereoisomer, or isotopically labeled derivative thereof, wherein $R^1$ is —NHC(O)CH═$CH_2$.

9. A compound of claim 1, or a pharmaceutically acceptable salt, solvate, hydrate, tautomer, stereoisomer, or isotopically labeled derivative thereof, wherein p=0 and D=piperidinyl, 1,2,3,4-tetrahydroisoquinolinyl, or

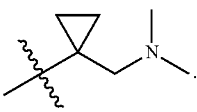 [SMILES: *C1(CN(C)C)CC1]

10. A compound of claim 9, or a pharmaceutically acceptable salt, solvate, hydrate, tautomer, stereoisomer, or isotopically labeled derivative thereof, wherein q=1 and $R^{11}$ is methyl.

11. A compound of claim 1, or a pharmaceutically acceptable salt, solvate, hydrate, tautomer, stereoisomer, or isotopically labeled derivative thereof, wherein p=1 and D=tetrahydropyranyl or tetrahydrofuryl.

12. A compound of claim 11, or a pharmaceutically acceptable salt, solvate, hydrate, tautomer, stereoisomer, or isotopically labeled derivative thereof, wherein q=0.

13. A pharmaceutical composition comprising:
a compound of claim 1, or a pharmaceutically acceptable salt, solvate, hydrate, tautomer, stereoisomer, or isotopically labeled derivative thereof; and
a pharmaceutically acceptable excipient.

14. A kit comprising:
a compound of claim 1, or a pharmaceutically acceptable salt, solvate, hydrate, tautomer, stereoisomer, or isotopically labeled derivative thereof; and
instructions for using the compound, or a pharmaceutically acceptable salt, solvate, hydrate, tautomer, stereoisomer, or isotopically labeled derivative thereof.

15. A method of inhibiting the activity of cyclin-dependent kinase 7 (CDK7) in a subject, biological sample, tissue, or cell, the method comprising administering to the subject or contacting the biological sample, tissue, or cell with an effective amount of a compound of claim 1, or a pharmaceutically acceptable salt, solvate, hydrate, tautomer, stereoisomer, or isotopically labeled derivative thereof.

* * * * *

UNITED STATES PATENT AND TRADEMARK OFFICE

CERTIFICATE OF CORRECTION

PATENT NO. : 12,281,126 B2
APPLICATION NO. : 17/418353
DATED : April 22, 2025
INVENTOR(S) : Nathanael S. Gray et al.

It is certified that error appears in the above-identified patent and that said Letters Patent is hereby corrected as shown below:

In the Claims

Claim 1, Column 153, Line 15 to Line 24, delete:

"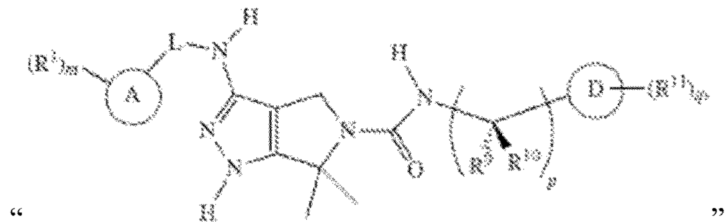"

And insert:

--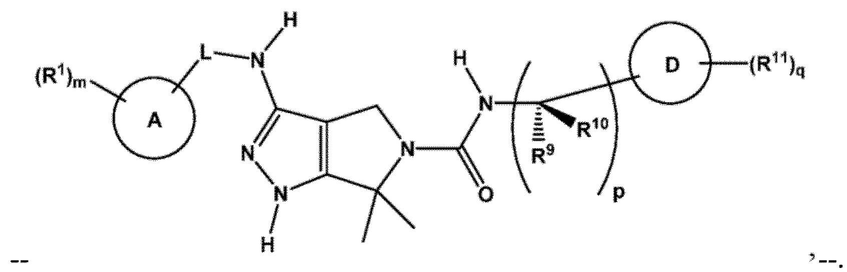

'--.

Signed and Sealed this
Tenth Day of June, 2025

Coke Morgan Stewart
*Acting Director of the United States Patent and Trademark Office*